US011725185B2

(12) United States Patent
Xian et al.

(10) Patent No.: US 11,725,185 B2
(45) Date of Patent: Aug. 15, 2023

(54) STEM CELL CULTURE SYSTEMS FOR COLUMNAR EPITHELIAL STEM CELLS, AND USES RELATED THERETO

(71) Applicants: University of Houston System, Houston, TX (US); Tract Pharmaceuticals, Inc., West Hartford, CT (US)

(72) Inventors: Wa Xian, Sugar Land, TX (US); Frank McKeon, Sugar Land, TX (US); Matthew P. Vincent, Amesbury, MA (US)

(73) Assignee: University of Houston System, Houston, TX (US)

( * ) Notice: Subject to any disclaimer, the term of this patent is extended or adjusted under 35 U.S.C. 154(b) by 382 days.

(21) Appl. No.: 16/958,074

(22) PCT Filed: Dec. 28, 2018

(86) PCT No.: PCT/US2018/067858
§ 371 (c)(1),
(2) Date: Jun. 25, 2020

(87) PCT Pub. No.: WO2019/133810
PCT Pub. Date: Jul. 4, 2019

(65) Prior Publication Data
US 2021/0062145 A1     Mar. 4, 2021

Related U.S. Application Data

(60) Provisional application No. 62/724,937, filed on Aug. 30, 2018, provisional application No. 62/611,176, filed on Dec. 28, 2017.

(51) Int. Cl.
*C12N 5/074* (2010.01)

(52) U.S. Cl.
CPC ........ *C12N 5/0607* (2013.01); *C12N 2500/38* (2013.01); *C12N 2501/105* (2013.01);
(Continued)

(58) Field of Classification Search
None
See application file for complete search history.

(56) References Cited

U.S. PATENT DOCUMENTS

2015/0273055 A1   10/2015   Smith et al.

FOREIGN PATENT DOCUMENTS

| JP | 2016-513469 | 5/2016 |
|----|-------------|--------|
| WO | WO 2017/043604 | 3/2007 |

(Continued)

OTHER PUBLICATIONS

Wang, Xia; et al; "Cloning and variation of ground state intestinal stem cells" Nature, 522, 173-178, 2015 (Year: 2015).*
(Continued)

*Primary Examiner* — David W Berke-Schlessel
(74) *Attorney, Agent, or Firm* — Parker Highlander PLLC

(57) ABSTRACT

The present invention relates to a culture media system that is useful for the isolation and epigenetically stable propagation of normal stem cells in culture which are derived from columnar epithelial tissues and cancer stem cells from epithelial cancers. In certain embodiments, the culture system is a feeder-free system.

10 Claims, 11 Drawing Sheets
Specification includes a Sequence Listing.

MUC2+ Goblet Cells

CHGA+ Endocrine Cells

DEFA6+ Paneth Cells

Villin+ Enterocytes

(52) U.S. Cl.
CPC .... *C12N 2501/135* (2013.01); *C12N 2501/15* (2013.01); *C12N 2501/155* (2013.01); *C12N 2501/165* (2013.01); *C12N 2501/33* (2013.01); *C12N 2501/415* (2013.01); *C12N 2501/603* (2013.01); *C12N 2501/727* (2013.01)

(56) References Cited

FOREIGN PATENT DOCUMENTS

| WO | WO 2014/152321 | 9/2014 |
|---|---|---|
| WO | WO 2016/079146 | 5/2016 |
| WO | WO 2017/170849 | 10/2017 |

OTHER PUBLICATIONS

Holmberg et al., "Culturing human intestinal stem cells for regenerative applications in the treatment of inflammatory bowel disease," *EMBO Molecular Medicine*, 9(5):558-570, 2017.

Hong et al., "Concise review: the potential use of intestinal stem cells to treat patients with intestinal failure," *Stem Cells Translational Medicine*, 6(2):666-676, 2017.

Leost et al., "Paullones are potent inhibitors of glycogen synthase kinase-3beta and cyclin-dependent kinase 5/p25," *Eur. J. Biochem.*, 267(19):5983-5994, 2000.

Liao et al., "Glycogen synthase kinase-3beta activity is required for androgen-stimulated gene expression in prostate cancer," *Endocrinology*, 145(6):2941-2949, 2004.

Liu et al., "A small-molecule agonist of the Wnt signaling pathway," *Angew Chem. Int. Ed. Engl.*, 44(13):1987-1990, 2005.

Meijer et al., "GSK-3-selective inhibitors derived from Tyrian purple indirubins," *Chem. Biol.*, 10(12):1255-1266, 2003.

Meijer et al., "Pharmacological inhibitors of glycogen synthase kinase 3," *Trends in Pharmacological Sciences*, 25(9):471-480, 2004.

Office Action issued in European Application No. 18836792.4, dated Feb. 17, 2022.

PCT International Preliminary Report on Patentability issued in International Application No. PCT/US2018/067858, dated Jun. 30, 2020.

PCT International Search Report and Written Opinion issued in International Application No. PCT/US2018/067858, dated Mar. 8, 2019.

Planutis et al., "Regulation of norrin receptor frizzled-4 by Wnt2 in colon-derived cells," *BMC Cell Biol.*, 8:12, 2007.

Theunissen et al., "Systematic identification of culture conditions for induction and maintenance of naïve human pluripotency," *Cell Stem Cell*, 15(4):471-487, 2014.

Wang et al., "Cloning and variation of ground state intestinal stem cells," *Nature*, 522(7555):173-178, 2015.

Japanese Office Action for JP Appl. No. 2020-555734 dated Dec. 14, 2022 with English translation, 9 pages.

\* cited by examiner

Fig. 3B
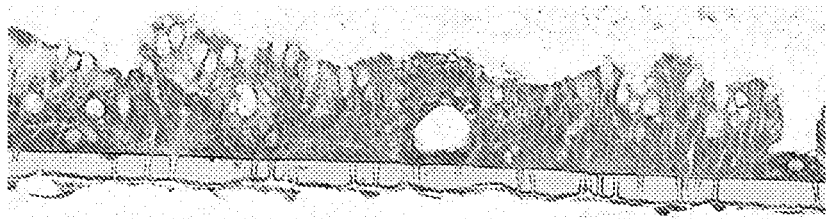
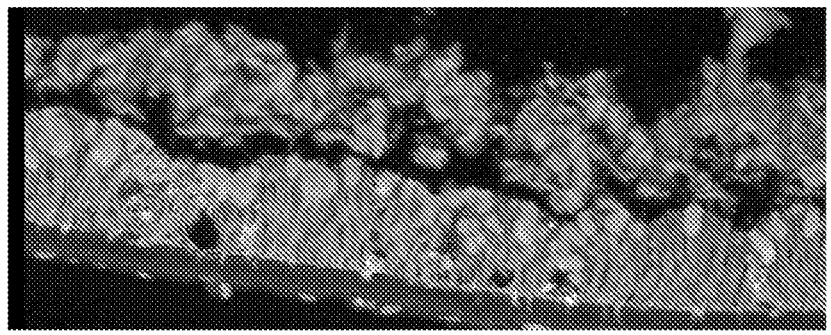
MUC2+
Goblet Cells
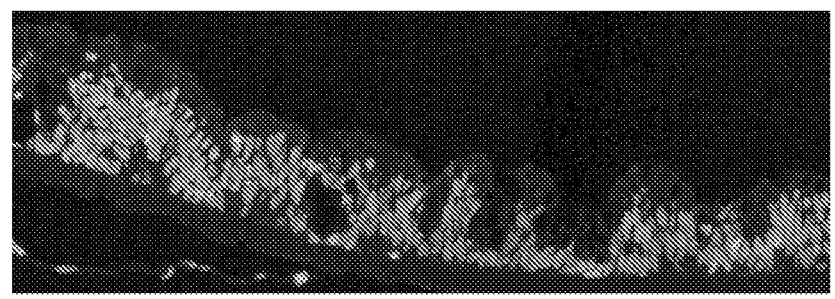
CHGA+
Endocrine Cells
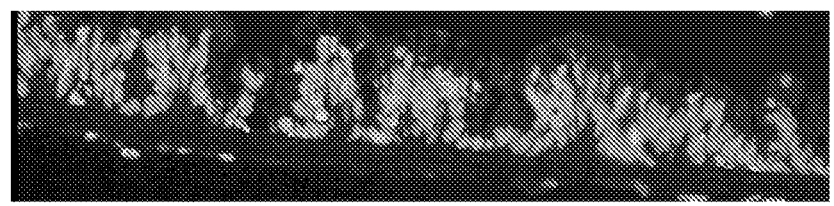
DEFA6+
Paneth Cells
Villin+
Enterocytes Fig. 5C
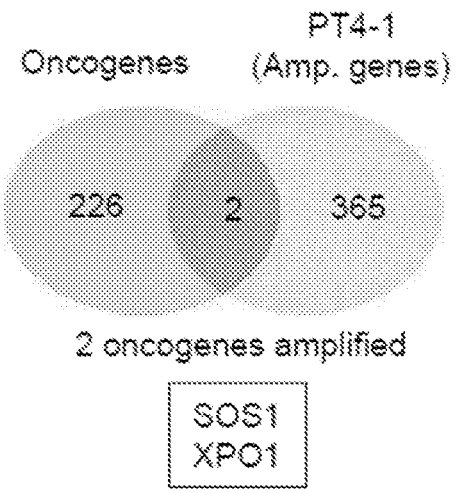
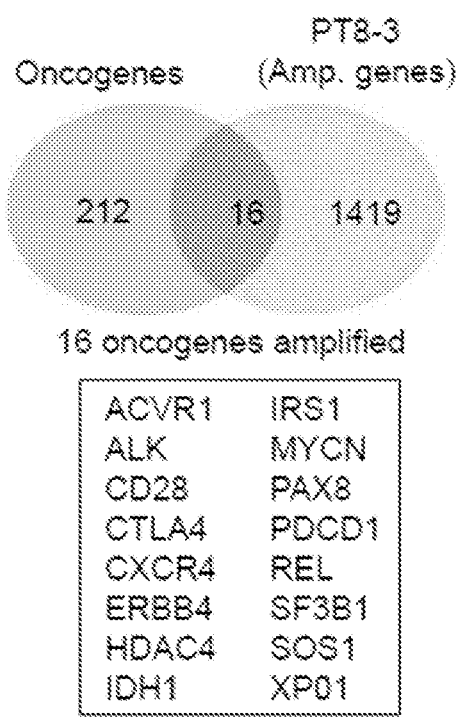

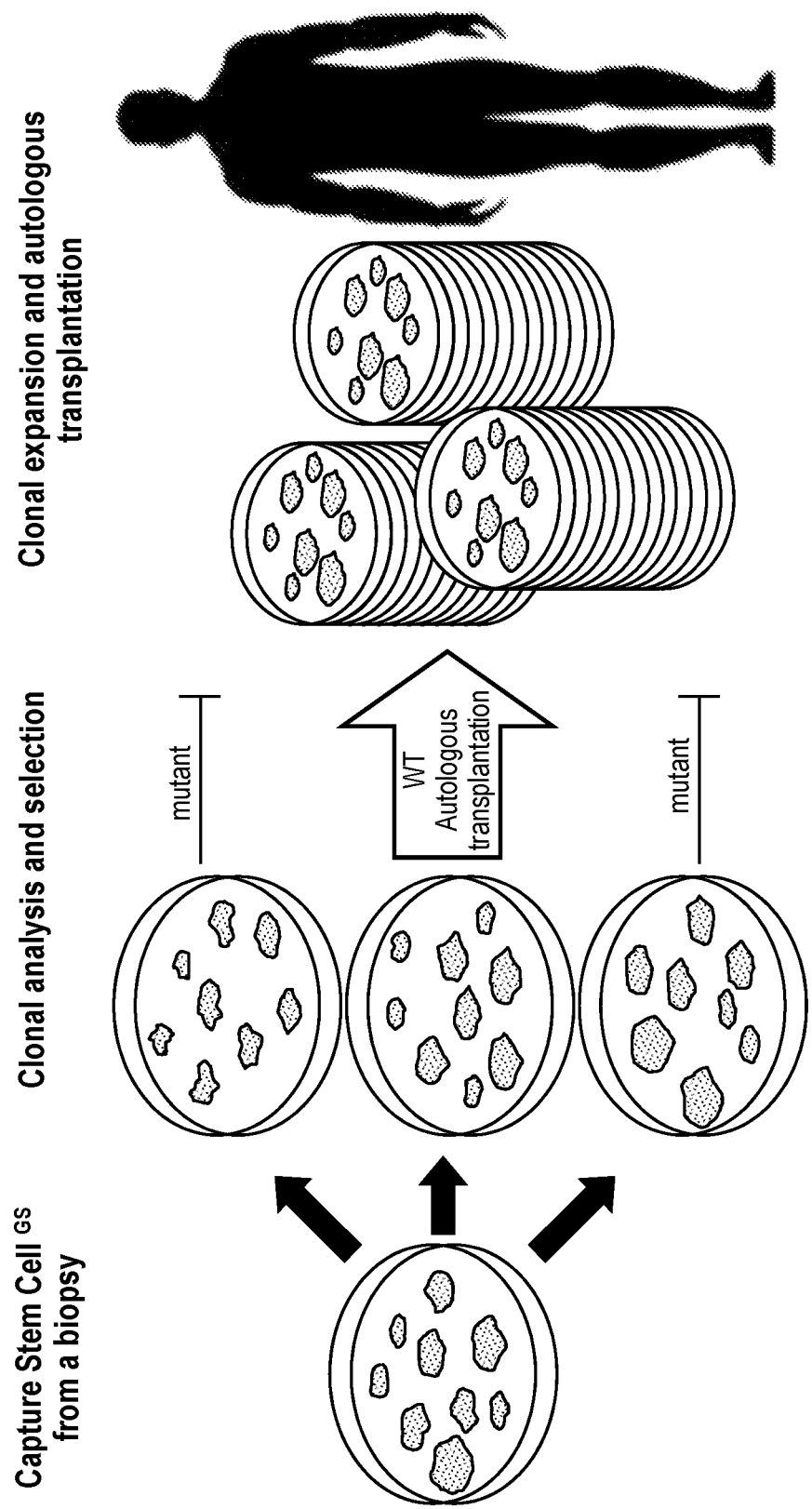

SEQUENCE LISTING

<160> NUMBER OF SEQ ID NOS: 36

<210> SEQ ID NO 1
<211> LENGTH: 232

```
<212> TYPE: PRT
<213> ORGANISM: Homo sapiens

<400> SEQUENCE: 1

Met Glu Arg Cys Pro Ser Leu Gly Val Thr Leu Tyr Ala Leu Val Val
1               5                   10                  15

Val Leu Gly Leu Arg Ala Thr Pro Ala Gly Gly Gln His Tyr Leu His
            20                  25                  30

Ile Arg Pro Ala Pro Ser Asp Asn Leu Pro Leu Val Asp Leu Ile Glu
        35                  40                  45

His Pro Asp Pro Ile Phe Asp Pro Lys Glu Lys Asp Leu Asn Glu Thr
    50                  55                  60

Leu Leu Arg Ser Leu Leu Gly Gly His Tyr Asp Pro Gly Phe Met Ala
65                  70                  75                  80

Thr Ser Pro Pro Glu Asp Arg Pro Gly Gly Gly Gly Ala Ala Gly
                85                  90                  95

Gly Ala Glu Asp Leu Ala Glu Leu Asp Gln Leu Leu Arg Gln Arg Pro
            100                 105                 110

Ser Gly Ala Met Pro Ser Glu Ile Lys Gly Leu Glu Phe Ser Glu Gly
            115                 120                 125

Leu Ala Gln Gly Lys Lys Gln Arg Leu Ser Lys Lys Leu Arg Arg Lys
130                 135                 140

Leu Gln Met Trp Leu Trp Ser Gln Thr Phe Cys Pro Val Leu Tyr Ala
145                 150                 155                 160

Trp Asn Asp Leu Gly Ser Arg Phe Trp Pro Arg Tyr Val Lys Val Gly
                165                 170                 175

Ser Cys Phe Ser Lys Arg Ser Cys Ser Val Pro Glu Gly Met Val Cys
            180                 185                 190

Lys Pro Ser Lys Ser Val His Leu Thr Val Leu Arg Trp Arg Cys Gln
            195                 200                 205

Arg Arg Gly Gly Gln Arg Cys Gly Trp Ile Pro Ile Gln Tyr Pro Ile
210                 215                 220

Ile Ser Glu Cys Lys Cys Ser Cys
225                 230

<210> SEQ ID NO 2
<211> LENGTH: 955
<212> TYPE: PRT
<213> ORGANISM: Homo sapiens

<400> SEQUENCE: 2

Met Pro Ser Leu Pro Ala Pro Ala Pro Leu Leu Leu Leu Gly Leu
1               5                   10                  15

Leu Leu Leu Gly Ser Arg Pro Ala Arg Gly Ala Gly Pro Glu Pro Pro
            20                  25                  30

Val Leu Pro Ile Arg Ser Glu Lys Glu Pro Leu Pro Val Arg Gly Ala
        35                  40                  45

Ala Gly Cys Thr Phe Gly Gly Lys Val Tyr Ala Leu Asp Glu Thr Trp
    50                  55                  60

His Pro Asp Leu Gly Glu Pro Phe Gly Val Met Arg Cys Val Leu Cys
65                  70                  75                  80

Ala Cys Glu Ala Pro Gln Trp Gly Arg Arg Thr Arg Gly Pro Gly Arg
                85                  90                  95

Val Ser Cys Lys Asn Ile Lys Pro Glu Cys Pro Thr Pro Ala Cys Gly
            100                 105                 110
```

```
Gln Pro Arg Gln Leu Pro Gly His Cys Cys Gln Thr Cys Pro Gln Glu
            115                 120                 125

Arg Ser Ser Ser Glu Arg Gln Pro Ser Gly Leu Ser Phe Glu Tyr Pro
130                 135                 140

Arg Asp Pro Glu His Arg Ser Tyr Ser Asp Arg Gly Glu Pro Gly Ala
145                 150                 155                 160

Glu Glu Arg Ala Arg Gly Asp Gly His Thr Asp Phe Val Ala Leu Leu
                165                 170                 175

Thr Gly Pro Arg Ser Gln Ala Val Arg Ala Arg Val Ser Leu Leu
                180                 185                 190

Arg Ser Ser Leu Arg Phe Ser Ile Ser Tyr Arg Leu Asp Arg Pro
                195                 200                 205

Thr Arg Ile Arg Phe Ser Asp Ser Asn Gly Ser Val Leu Phe Glu His
    210                 215                 220

Pro Ala Ala Pro Thr Gln Asp Gly Leu Val Cys Gly Val Trp Arg Ala
225                 230                 235                 240

Val Pro Arg Leu Ser Leu Arg Leu Leu Arg Ala Glu Gln Leu His Val
                245                 250                 255

Ala Leu Val Thr Leu Thr His Pro Ser Gly Glu Val Trp Gly Pro Leu
                260                 265                 270

Ile Arg His Arg Ala Leu Ala Ala Glu Thr Phe Ser Ala Ile Leu Thr
    275                 280                 285

Leu Glu Gly Pro Pro Gln Gln Gly Val Gly Gly Ile Thr Leu Leu Thr
    290                 295                 300

Leu Ser Asp Thr Glu Asp Ser Leu His Phe Leu Leu Phe Arg Gly
305                 310                 315                 320

Leu Leu Glu Pro Arg Ser Gly Gly Leu Thr Gln Val Pro Leu Arg Leu
                325                 330                 335

Gln Ile Leu His Gln Gly Gln Leu Leu Arg Glu Leu Gln Ala Asn Val
            340                 345                 350

Ser Ala Gln Glu Pro Gly Phe Ala Glu Val Leu Pro Asn Leu Thr Val
            355                 360                 365

Gln Glu Met Asp Trp Leu Val Leu Gly Glu Leu Gln Met Ala Leu Glu
    370                 375                 380

Trp Ala Gly Arg Pro Gly Leu Arg Ile Ser Gly His Ile Ala Ala Arg
385                 390                 395                 400

Lys Ser Cys Asp Val Leu Gln Ser Val Leu Cys Gly Ala Asp Ala Leu
                405                 410                 415

Ile Pro Val Gln Thr Gly Ala Ala Gly Ser Ala Ser Leu Thr Leu Leu
                420                 425                 430

Gly Asn Gly Ser Leu Ile Tyr Gln Val Gln Val Val Gly Thr Ser Ser
            435                 440                 445

Glu Val Val Ala Met Thr Leu Glu Thr Lys Pro Gln Arg Arg Asp Gln
450                 455                 460

Arg Thr Val Leu Cys His Met Ala Gly Leu Gln Pro Gly Gly His Thr
465                 470                 475                 480

Ala Val Gly Ile Cys Pro Gly Leu Gly Ala Arg Gly Ala His Met Leu
                485                 490                 495

Leu Gln Asn Glu Leu Phe Leu Asn Val Gly Thr Lys Asp Phe Pro Asp
            500                 505                 510

Gly Glu Leu Arg Gly His Val Ala Ala Leu Pro Tyr Cys Gly His Ser
            515                 520                 525

Ala Arg His Asp Thr Leu Pro Val Pro Leu Ala Gly Ala Leu Val Leu
```

```
            530                 535                 540
Pro Pro Val Lys Ser Gln Ala Ala Gly His Ala Trp Leu Ser Leu Asp
545                 550                 555                 560

Thr His Cys His Leu His Tyr Glu Val Leu Leu Ala Gly Leu Gly Gly
                    565                 570                 575

Ser Glu Gln Gly Thr Val Thr Ala His Leu Leu Gly Pro Pro Gly Thr
                580                 585                 590

Pro Gly Pro Arg Arg Leu Leu Lys Gly Phe Tyr Gly Ser Glu Ala Gln
            595                 600                 605

Gly Val Val Lys Asp Leu Glu Pro Glu Leu Leu Arg His Leu Ala Lys
            610                 615                 620

Gly Met Ala Ser Leu Leu Ile Thr Thr Lys Gly Ser Pro Arg Gly Glu
625                 630                 635                 640

Leu Arg Gly Gln Val His Ile Ala Asn Gln Cys Glu Val Gly Gly Leu
                    645                 650                 655

Arg Leu Glu Ala Ala Gly Ala Glu Gly Val Arg Ala Leu Gly Ala Pro
                660                 665                 670

Asp Thr Ala Ser Ala Ala Pro Val Val Pro Gly Leu Pro Ala Leu
                675                 680                 685

Ala Pro Ala Lys Pro Gly Gly Pro Gly Arg Pro Arg Asp Pro Asn Thr
            690                 695                 700

Cys Phe Phe Glu Gly Gln Gln Arg Pro His Gly Ala Arg Trp Ala Pro
705                 710                 715                 720

Asn Tyr Asp Pro Leu Cys Ser Leu Cys Thr Cys Gln Arg Arg Thr Val
                    725                 730                 735

Ile Cys Asp Pro Val Val Cys Pro Pro Ser Cys Pro His Pro Val
                740                 745                 750

Gln Ala Pro Asp Gln Cys Cys Pro Val Cys Pro Glu Lys Gln Asp Val
                755                 760                 765

Arg Asp Leu Pro Gly Leu Pro Arg Ser Arg Asp Pro Gly Glu Gly Cys
            770                 775                 780

Tyr Phe Asp Gly Asp Arg Ser Trp Arg Ala Ala Gly Thr Arg Trp His
785                 790                 795                 800

Pro Val Val Pro Pro Phe Gly Leu Ile Lys Cys Ala Val Cys Thr Cys
                    805                 810                 815

Lys Gly Gly Thr Gly Glu Val His Cys Glu Lys Val Gln Cys Pro Arg
                820                 825                 830

Leu Ala Cys Ala Gln Pro Val Arg Val Asn Pro Thr Asp Cys Cys Lys
                835                 840                 845

Gln Cys Pro Val Gly Ser Gly Ala His Pro Gln Leu Gly Asp Pro Met
850                 855                 860

Gln Ala Asp Gly Pro Arg Gly Cys Arg Phe Ala Gly Gln Trp Phe Pro
865                 870                 875                 880

Glu Ser Gln Ser Trp His Pro Ser Val Pro Pro Phe Gly Glu Met Ser
                    885                 890                 895

Cys Ile Thr Cys Arg Cys Gly Ala Gly Val Pro His Cys Glu Arg Asp
                900                 905                 910

Asp Cys Ser Leu Pro Leu Ser Cys Gly Ser Gly Lys Glu Ser Arg Cys
                915                 920                 925

Cys Ser Arg Cys Thr Ala His Arg Arg Pro Ala Pro Glu Thr Arg Thr
            930                 935                 940

Asp Pro Glu Leu Glu Lys Glu Ala Glu Gly Ser
945                 950                 955
```

<210> SEQ ID NO 3
<211> LENGTH: 344
<212> TYPE: PRT
<213> ORGANISM: Homo sapiens

<400> SEQUENCE: 3

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
290                 295                 300

Gly Val Leu Leu Glu Val Lys His Ser Gly Ser Cys Asn Ser Ile Ser
305                 310                 315                 320

Glu Asp Thr Glu Glu Glu Glu Asp Glu Asp Gln Asp Tyr Ser Phe
                325                 330                 335

Pro Ile Ser Ser Ile Leu Glu Trp
            340

<210> SEQ ID NO 4
<211> LENGTH: 180
<212> TYPE: PRT

<213> ORGANISM: Homo sapiens

<400> SEQUENCE: 4

Met Leu Arg Val Leu Val Gly Ala Val Leu Pro Ala Met Leu Leu Ala
1               5                   10                  15

Ala Pro Pro Ile Asn Lys Leu Ala Leu Phe Pro Asp Lys Ser Ala
            20                  25                  30

Trp Cys Glu Ala Lys Asn Ile Thr Gln Ile Val Gly His Ser Gly Cys
        35                  40                  45

Glu Ala Lys Ser Ile Gln Asn Arg Ala Cys Leu Gly Gln Cys Phe Ser
    50                  55                  60

Tyr Ser Val Pro Asn Thr Phe Pro Gln Ser Thr Glu Ser Leu Val His
65                  70                  75                  80

Cys Asp Ser Cys Met Pro Ala Gln Ser Met Trp Glu Ile Val Thr Leu
                85                  90                  95

Glu Cys Pro Gly His Glu Glu Val Pro Arg Val Asp Lys Leu Val Glu
            100                 105                 110

Lys Ile Leu His Cys Ser Cys Gln Ala Cys Gly Lys Glu Pro Ser His
        115                 120                 125

Glu Gly Leu Ser Val Tyr Val Gln Gly Glu Asp Gly Pro Gly Ser Gln
    130                 135                 140

Pro Gly Thr His Pro His Pro His Pro His Pro Gly Gly Gln
145                 150                 155                 160

Thr Pro Glu Pro Glu Asp Pro Pro Gly Ala Pro His Thr Glu Glu Glu
                165                 170                 175

Gly Ala Glu Asp
            180

<210> SEQ ID NO 5
<211> LENGTH: 267
<212> TYPE: PRT
<213> ORGANISM: Homo sapiens

<400> SEQUENCE: 5

Met His Leu Leu Leu Phe Gln Leu Val Leu Leu Pro Leu Gly Lys
1               5                   10                  15

Thr Thr Arg His Gln Asp Gly Arg Gln Asn Gln Ser Ser Leu Ser Pro
            20                  25                  30

Val Leu Leu Pro Arg Asn Gln Arg Glu Leu Pro Thr Gly Asn His Glu
        35                  40                  45

Glu Ala Glu Glu Lys Pro Asp Leu Phe Val Ala Val Pro His Leu Val
    50                  55                  60

Ala Thr Ser Pro Ala Gly Glu Gly Gln Arg Gln Arg Glu Lys Met Leu
65                  70                  75                  80

Ser Arg Phe Gly Arg Phe Trp Lys Lys Pro Glu Arg Glu Met His Pro
                85                  90                  95

Ser Arg Asp Ser Asp Ser Glu Pro Phe Pro Pro Gly Thr Gln Ser Leu
            100                 105                 110

Ile Gln Pro Ile Asp Gly Met Lys Met Glu Lys Ser Pro Leu Arg Glu
        115                 120                 125

Glu Ala Lys Lys Phe Trp His His Phe Met Phe Arg Lys Thr Pro Ala
    130                 135                 140

Ser Gln Gly Val Ile Leu Pro Ile Lys Ser His Glu Val His Trp Glu
145                 150                 155                 160

Thr Cys Arg Thr Val Pro Phe Ser Gln Thr Ile Thr His Glu Gly Cys

```
                       165                 170                 175
Glu Lys Val Val Gln Asn Asn Leu Cys Phe Gly Lys Cys Gly Ser
                180                 185                 190

Val His Phe Pro Gly Ala Ala Gln His Ser His Thr Ser Cys Ser His
            195                 200                 205

Cys Leu Pro Ala Lys Phe Thr Thr Met His Leu Pro Leu Asn Cys Thr
        210                 215                 220

Glu Leu Ser Ser Val Ile Lys Val Val Met Leu Val Glu Glu Cys Gln
225                 230                 235                 240

Cys Lys Val Lys Thr Glu His Glu Asp Gly His Ile Leu His Ala Gly
                245                 250                 255

Ser Gln Asp Ser Phe Ile Pro Gly Val Ser Ala
                260                 265

<210> SEQ ID NO 6
<211> LENGTH: 184
<212> TYPE: PRT
<213> ORGANISM: Homo sapiens

<400> SEQUENCE: 6

Met Ser Arg Thr Ala Tyr Thr Val Gly Ala Leu Leu Leu Leu Leu Gly
1               5                   10                  15

Thr Leu Leu Pro Ala Ala Glu Gly Lys Lys Gly Ser Gln Gly Ala
            20                  25                  30

Ile Pro Pro Pro Asp Lys Ala Gln His Asn Asp Ser Glu Gln Thr Gln
        35                  40                  45

Ser Pro Gln Gln Pro Gly Ser Arg Asn Arg Gly Arg Gly Gln Gly Arg
    50                  55                  60

Gly Thr Ala Met Pro Gly Glu Glu Val Leu Glu Ser Ser Gln Glu Ala
65                  70                  75                  80

Leu His Val Thr Glu Arg Lys Tyr Leu Lys Arg Asp Trp Cys Lys Thr
                85                  90                  95

Gln Pro Leu Lys Gln Thr Ile His Glu Glu Gly Cys Asn Ser Arg Thr
            100                 105                 110

Ile Ile Asn Arg Phe Cys Tyr Gly Gln Cys Asn Ser Phe Tyr Ile Pro
        115                 120                 125

Arg His Ile Arg Lys Glu Glu Gly Ser Phe Gln Ser Cys Ser Phe Cys
    130                 135                 140

Lys Pro Lys Lys Phe Thr Thr Met Met Val Thr Leu Asn Cys Pro Glu
145                 150                 155                 160

Leu Gln Pro Pro Thr Lys Lys Arg Val Thr Arg Val Lys Gln Cys
                165                 170                 175

Arg Cys Ile Ser Ile Asp Leu Asp
            180

<210> SEQ ID NO 7
<211> LENGTH: 213
<212> TYPE: PRT
<213> ORGANISM: Homo sapiens

<400> SEQUENCE: 7

Met Gln Leu Pro Leu Ala Leu Cys Leu Val Cys Leu Leu Val His Thr
1               5                   10                  15

Ala Phe Arg Val Val Glu Gly Gln Gly Trp Gln Ala Phe Lys Asn Asp
            20                  25                  30

Ala Thr Glu Ile Ile Pro Glu Leu Gly Glu Tyr Pro Glu Pro Pro Pro
```

```
                35                  40                  45
Glu Leu Glu Asn Asn Lys Thr Met Asn Arg Ala Glu Asn Gly Gly Arg
 50                  55                  60

Pro Pro His His Pro Phe Glu Thr Lys Asp Val Ser Glu Tyr Ser Cys
 65                  70                  75                  80

Arg Glu Leu His Phe Thr Arg Tyr Val Thr Asp Gly Pro Cys Arg Ser
                 85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Gly Lys Trp Trp Arg Pro Ser
        115                 120                 125

Gly Pro Asp Phe Arg Cys Ile Pro Asp Arg Tyr Arg Ala Gln Arg Val
    130                 135                 140

Gln Leu Leu Cys Pro Gly Gly Glu Ala Pro Arg Ala Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Thr Glu Ala Ala Arg Pro Gln Lys Gly
            180                 185                 190

Arg Lys Pro Arg Pro Arg Ala Arg Ser Ala Lys Ala Asn Gln Ala Glu
        195                 200                 205

Leu Glu Asn Ala Tyr
    210

<210> SEQ ID NO 8
<211> LENGTH: 70
<212> TYPE: PRT
<213> ORGANISM: Homo sapiens

<400> SEQUENCE: 8

Met Lys Ala Thr Ile Ile Leu Leu Leu Ala Gln Val Ser Trp Ala
 1               5                  10                  15

Gly Pro Phe Gln Gln Arg Gly Leu Phe Asp Phe Met Leu Glu Asp Glu
                20                  25                  30

Ala Ser Gly Ile Gly Pro Glu Val Pro Asp Asp Arg Asp Phe Glu Pro
            35                  40                  45

Ser Leu Gly Pro Val Cys Pro Phe Arg Cys Gln Cys His Leu Arg Val
        50                  55                  60

Val Gln Cys Ser Asp Leu
 65                  70

<210> SEQ ID NO 9
<211> LENGTH: 1474
<212> TYPE: PRT
<213> ORGANISM: Homo sapiens

<400> SEQUENCE: 9

Met Gly Lys Asn Lys Leu Leu His Pro Ser Leu Val Leu Leu Leu
 1               5                  10                  15

Val Leu Leu Pro Thr Asp Ala Ser Val Ser Gly Lys Pro Gln Tyr Met
                20                  25                  30

Val Leu Val Pro Ser Leu Leu His Thr Glu Thr Thr Glu Lys Gly Cys
            35                  40                  45

Val Leu Leu Ser Tyr Leu Asn Glu Thr Val Thr Val Ser Ala Ser Leu
        50                  55                  60

Glu Ser Val Arg Gly Asn Arg Ser Leu Phe Thr Asp Leu Glu Ala Glu
```

```
                65                  70                  75                  80
Asn Asp Val Leu His Cys Val Ala Phe Ala Val Pro Lys Ser Ser Ser
                    85                  90                  95
Asn Glu Glu Val Met Phe Leu Thr Val Gln Val Lys Gly Pro Thr Gln
                    100                 105                 110
Glu Phe Lys Lys Arg Thr Thr Val Met Val Lys Asn Glu Asp Ser Leu
                    115                 120                 125
Val Phe Val Gln Thr Asp Lys Ser Ile Tyr Lys Pro Gly Gln Thr Val
                    130                 135                 140
Lys Phe Arg Val Val Ser Met Asp Glu Asn Phe His Pro Leu Asn Glu
145                 150                 155                 160
Leu Ile Pro Leu Val Tyr Ile Gln Asp Pro Lys Gly Asn Arg Ile Ala
                    165                 170                 175
Gln Trp Gln Ser Phe Gln Leu Glu Gly Gly Leu Lys Gln Phe Ser Phe
                    180                 185                 190
Pro Leu Ser Ser Glu Pro Phe Gln Gly Ser Tyr Lys Val Val Val Gln
                    195                 200                 205
Lys Lys Ser Gly Gly Arg Thr Glu His Pro Phe Thr Val Glu Glu Phe
                    210                 215                 220
Val Leu Pro Lys Phe Glu Val Gln Val Thr Val Pro Lys Ile Ile Thr
225                 230                 235                 240
Ile Leu Glu Glu Glu Met Asn Val Ser Val Cys Gly Leu Tyr Thr Tyr
                    245                 250                 255
Gly Lys Pro Val Pro Gly His Val Thr Val Ser Ile Cys Arg Lys Tyr
                    260                 265                 270
Ser Asp Ala Ser Asp Cys His Gly Glu Asp Ser Gln Ala Phe Cys Glu
                    275                 280                 285
Lys Phe Ser Gly Gln Leu Asn Ser His Gly Cys Phe Tyr Gln Gln Val
                    290                 295                 300
Lys Thr Lys Val Phe Gln Leu Lys Arg Lys Glu Tyr Glu Met Lys Leu
305                 310                 315                 320
His Thr Glu Ala Gln Ile Gln Glu Glu Gly Thr Val Val Glu Leu Thr
                    325                 330                 335
Gly Arg Gln Ser Ser Glu Ile Thr Arg Thr Ile Thr Lys Leu Ser Phe
                    340                 345                 350
Val Lys Val Asp Ser His Phe Arg Gln Gly Ile Pro Phe Phe Gly Gln
                    355                 360                 365
Val Arg Leu Val Asp Gly Lys Gly Val Pro Ile Pro Asn Lys Val Ile
                    370                 375                 380
Phe Ile Arg Gly Asn Glu Ala Asn Tyr Tyr Ser Asn Ala Thr Thr Asp
385                 390                 395                 400
Glu His Gly Leu Val Gln Phe Ser Ile Asn Thr Thr Asn Val Met Gly
                    405                 410                 415
Thr Ser Leu Thr Val Arg Val Asn Tyr Lys Asp Arg Ser Pro Cys Tyr
                    420                 425                 430
Gly Tyr Gln Trp Val Ser Glu Glu His Glu Glu Ala His His Thr Ala
                    435                 440                 445
Tyr Leu Val Phe Ser Pro Ser Lys Ser Phe Val His Leu Glu Pro Met
                    450                 455                 460
Ser His Glu Leu Pro Cys Gly His Thr Gln Thr Val Gln Ala His Tyr
465                 470                 475                 480
Ile Leu Asn Gly Gly Thr Leu Leu Gly Leu Lys Lys Leu Ser Phe Tyr
                    485                 490                 495
```

```
Tyr Leu Ile Met Ala Lys Gly Ile Val Arg Thr Gly Thr His Gly
            500                 505                 510
Leu Leu Val Lys Gln Glu Asp Met Lys Gly His Phe Ser Ile Ser Ile
            515                 520                 525
Pro Val Lys Ser Asp Ile Ala Pro Val Ala Arg Leu Leu Ile Tyr Ala
            530                 535                 540
Val Leu Pro Thr Gly Asp Val Ile Gly Asp Ser Ala Lys Tyr Asp Val
545                 550                 555                 560
Glu Asn Cys Leu Ala Asn Lys Val Asp Leu Ser Phe Ser Pro Ser Gln
                565                 570                 575
Ser Leu Pro Ala Ser His Ala His Leu Arg Val Thr Ala Ala Pro Gln
            580                 585                 590
Ser Val Cys Ala Leu Arg Ala Val Asp Gln Ser Val Leu Leu Met Lys
            595                 600                 605
Pro Asp Ala Glu Leu Ser Ala Ser Ser Val Tyr Asn Leu Leu Pro Glu
            610                 615                 620
Lys Asp Leu Thr Gly Phe Pro Gly Pro Leu Asn Asp Gln Asp Asp Glu
625                 630                 635                 640
Asp Cys Ile Asn Arg His Asn Val Tyr Ile Asn Gly Ile Thr Tyr Thr
                645                 650                 655
Pro Val Ser Ser Thr Asn Glu Lys Asp Met Tyr Ser Phe Leu Glu Asp
            660                 665                 670
Met Gly Leu Lys Ala Phe Thr Asn Ser Lys Ile Arg Lys Pro Lys Met
            675                 680                 685
Cys Pro Gln Leu Gln Gln Tyr Glu Met His Gly Pro Glu Gly Leu Arg
            690                 695                 700
Val Gly Phe Tyr Glu Ser Asp Val Met Gly Arg Gly His Ala Arg Leu
705                 710                 715                 720
Val His Val Glu Glu Pro His Thr Glu Thr Val Arg Lys Tyr Phe Pro
                725                 730                 735
Glu Thr Trp Ile Trp Asp Leu Val Val Val Asn Ser Ala Gly Val Ala
            740                 745                 750
Glu Val Gly Val Thr Val Pro Asp Thr Ile Thr Glu Trp Lys Ala Gly
            755                 760                 765
Ala Phe Cys Leu Ser Glu Asp Ala Gly Leu Gly Ile Ser Ser Thr Ala
            770                 775                 780
Ser Leu Arg Ala Phe Gln Pro Phe Phe Val Glu Leu Thr Met Pro Tyr
785                 790                 795                 800
Ser Val Ile Arg Gly Glu Ala Phe Thr Leu Lys Ala Thr Val Leu Asn
                805                 810                 815
Tyr Leu Pro Lys Cys Ile Arg Val Ser Val Gln Leu Glu Ala Ser Pro
            820                 825                 830
Ala Phe Leu Ala Val Pro Val Glu Lys Glu Gln Ala Pro His Cys Ile
            835                 840                 845
Cys Ala Asn Gly Arg Gln Thr Val Ser Trp Ala Val Thr Pro Lys Ser
            850                 855                 860
Leu Gly Asn Val Asn Phe Thr Val Ser Ala Glu Ala Leu Glu Ser Gln
865                 870                 875                 880
Glu Leu Cys Gly Thr Glu Val Pro Ser Val Pro Glu His Gly Arg Lys
                885                 890                 895
Asp Thr Val Ile Lys Pro Leu Leu Val Glu Pro Glu Gly Leu Glu Lys
            900                 905                 910
```

```
Glu Thr Thr Phe Asn Ser Leu Leu Cys Pro Ser Gly Glu Val Ser
            915                 920                 925

Glu Glu Leu Ser Leu Lys Leu Pro Pro Asn Val Val Glu Glu Ser Ala
    930                 935                 940

Arg Ala Ser Val Ser Val Leu Gly Asp Ile Leu Gly Ser Ala Met Gln
945                 950                 955                 960

Asn Thr Gln Asn Leu Leu Gln Met Pro Tyr Gly Cys Gly Glu Gln Asn
                965                 970                 975

Met Val Leu Phe Ala Pro Asn Ile Tyr Val Leu Asp Tyr Leu Asn Glu
            980                 985                 990

Thr Gln Gln Leu Thr Pro Glu Ile Lys Ser Lys Ala Ile Gly Tyr Leu
        995                 1000                1005

Asn Thr Gly Tyr Gln Arg Gln Leu Asn Tyr Lys His Tyr Asp Gly
    1010                1015                1020

Ser Tyr Ser Thr Phe Gly Glu Arg Tyr Gly Arg Asn Gln Gly Asn
    1025                1030                1035

Thr Trp Leu Thr Ala Phe Val Leu Lys Thr Phe Ala Gln Ala Arg
    1040                1045                1050

Ala Tyr Ile Phe Ile Asp Glu Ala His Ile Thr Gln Ala Leu Ile
    1055                1060                1065

Trp Leu Ser Gln Arg Gln Lys Asp Asn Gly Cys Phe Arg Ser Ser
    1070                1075                1080

Gly Ser Leu Leu Asn Asn Ala Ile Lys Gly Gly Val Glu Asp Glu
    1085                1090                1095

Val Thr Leu Ser Ala Tyr Ile Thr Ile Ala Leu Leu Glu Ile Pro
    1100                1105                1110

Leu Thr Val Thr His Pro Val Val Arg Asn Ala Leu Phe Cys Leu
    1115                1120                1125

Glu Ser Ala Trp Lys Thr Ala Gln Glu Gly Asp His Gly Ser His
    1130                1135                1140

Val Tyr Thr Lys Ala Leu Leu Ala Tyr Ala Phe Ala Leu Ala Gly
    1145                1150                1155

Asn Gln Asp Lys Arg Lys Glu Val Leu Lys Ser Leu Asn Glu Glu
    1160                1165                1170

Ala Val Lys Lys Asp Asn Ser Val His Trp Glu Arg Pro Gln Lys
    1175                1180                1185

Pro Lys Ala Pro Val Gly His Phe Tyr Glu Pro Gln Ala Pro Ser
    1190                1195                1200

Ala Glu Val Glu Met Thr Ser Tyr Val Leu Leu Ala Tyr Leu Thr
    1205                1210                1215

Ala Gln Pro Ala Pro Thr Ser Glu Asp Leu Thr Ser Ala Thr Asn
    1220                1225                1230

Ile Val Lys Trp Ile Thr Lys Gln Gln Asn Ala Gln Gly Gly Phe
    1235                1240                1245

Ser Ser Thr Gln Asp Thr Val Val Ala Leu His Ala Leu Ser Lys
    1250                1255                1260

Tyr Gly Ala Ala Thr Phe Thr Arg Thr Gly Lys Ala Ala Gln Val
    1265                1270                1275

Thr Ile Gln Ser Ser Gly Thr Phe Ser Ser Lys Phe Gln Val Asp
    1280                1285                1290

Asn Asn Asn Arg Leu Leu Leu Gln Gln Val Ser Leu Pro Glu Leu
    1295                1300                1305

Pro Gly Glu Tyr Ser Met Lys Val Thr Gly Glu Gly Cys Val Tyr
```

-continued

```
                1310                1315                1320

Leu Gln Thr Ser Leu Lys Tyr Asn Ile Leu Pro Glu Lys Glu Glu
    1325                1330                1335

Phe Pro Phe Ala Leu Gly Val Gln Thr Leu Pro Gln Thr Cys Asp
1340                1345                1350

Glu Pro Lys Ala His Thr Ser Phe Gln Ile Ser Leu Ser Val Ser
        1355                1360                1365

Tyr Thr Gly Ser Arg Ser Ala Ser Asn Met Ala Ile Val Asp Val
1370                1375                1380

Lys Met Val Ser Gly Phe Ile Pro Leu Lys Pro Thr Val Lys Met
    1385                1390                1395

Leu Glu Arg Ser Asn His Val Ser Arg Thr Glu Val Ser Ser Asn
1400                1405                1410

His Val Leu Ile Tyr Leu Asp Lys Val Ser Asn Gln Thr Leu Ser
    1415                1420                1425

Leu Phe Phe Thr Val Leu Gln Asp Val Pro Val Arg Asp Leu Lys
    1430                1435                1440

Pro Ala Ile Val Lys Val Tyr Asp Tyr Tyr Glu Thr Asp Glu Phe
    1445                1450                1455

Ala Ile Ala Glu Tyr Asn Ala Pro Cys Ser Lys Asp Leu Gly Asn
    1460                1465                1470

Ala

<210> SEQ ID NO 10
<211> LENGTH: 263
<212> TYPE: PRT
<213> ORGANISM: Homo sapiens

<400> SEQUENCE: 10

Met Arg Leu Gly Leu Cys Val Val Ala Leu Val Leu Ser Trp Thr His
1               5                   10                  15

Leu Thr Ile Ser Ser Arg Gly Ile Lys Gly Lys Arg Gln Arg Ile
            20                  25                  30

Ser Ala Glu Gly Ser Gln Ala Cys Ala Lys Gly Cys Glu Leu Cys Ser
        35                  40                  45

Glu Val Asn Gly Cys Leu Lys Cys Ser Pro Lys Leu Phe Ile Leu Leu
    50                  55                  60

Glu Arg Asn Asp Ile Arg Gln Val Gly Val Cys Leu Pro Ser Cys Pro
65                  70                  75                  80

Pro Gly Tyr Phe Asp Ala Arg Asn Pro Asp Met Asn Lys Cys Ile Lys
                85                  90                  95

Cys Lys Ile Glu His Cys Glu Ala Cys Phe Ser His Asn Phe Cys Thr
            100                 105                 110

Lys Cys Lys Glu Gly Leu Tyr Leu His Lys Gly Arg Cys Tyr Pro Ala
        115                 120                 125

Cys Pro Glu Gly Ser Ser Ala Ala Asn Gly Thr Met Glu Cys Ser Ser
    130                 135                 140

Pro Ala Gln Cys Glu Met Ser Glu Trp Ser Pro Trp Gly Pro Cys Ser
145                 150                 155                 160

Lys Lys Gln Gln Leu Cys Gly Phe Arg Arg Gly Ser Glu Glu Arg Thr
                165                 170                 175

Arg Arg Val Leu His Ala Pro Val Gly Asp His Ala Ala Cys Ser Asp
            180                 185                 190

Thr Lys Glu Thr Arg Arg Cys Thr Val Arg Arg Val Pro Cys Pro Glu
```

```
            195                 200                 205
Gly Gln Lys Arg Lys Gly Gly Gln Gly Arg Arg Glu Asn Ala Asn
210                 215                 220

Arg Asn Leu Ala Arg Lys Glu Ser Lys Glu Ala Gly Ala Gly Ser Arg
225                 230                 235                 240

Arg Arg Lys Gly Gln Gln Gln Gln Gln Gly Thr Val Gly Pro
                245                 250                 255

Leu Thr Ser Ala Gly Pro Ala
            260

<210> SEQ ID NO 11
<211> LENGTH: 243
<212> TYPE: PRT
<213> ORGANISM: Homo sapiens

<400> SEQUENCE: 11

Met Gln Phe Arg Leu Phe Ser Phe Ala Leu Ile Ile Leu Asn Cys Met
1               5                   10                  15

Asp Tyr Ser His Cys Gln Gly Asn Arg Trp Arg Ser Lys Arg Ala
                20                  25                  30

Ser Tyr Val Ser Asn Pro Ile Cys Lys Gly Cys Leu Ser Cys Ser Lys
            35                  40                  45

Asp Asn Gly Cys Ser Arg Cys Gln Gln Lys Leu Phe Phe Phe Leu Arg
50                  55                  60

Arg Glu Gly Met Arg Gln Tyr Gly Glu Cys Leu His Ser Cys Pro Ser
65                  70                  75                  80

Gly Tyr Tyr Gly His Arg Ala Pro Asp Met Asn Arg Cys Ala Arg Cys
                85                  90                  95

Arg Ile Glu Asn Cys Asp Ser Cys Phe Ser Lys Asp Phe Cys Thr Lys
            100                 105                 110

Cys Lys Val Gly Phe Tyr Leu His Arg Gly Arg Cys Phe Asp Glu Cys
        115                 120                 125

Pro Asp Gly Phe Ala Pro Leu Glu Glu Thr Met Glu Cys Val Glu Gly
130                 135                 140

Cys Glu Val Gly His Trp Ser Glu Trp Gly Thr Cys Ser Arg Asn Asn
145                 150                 155                 160

Arg Thr Cys Gly Phe Lys Trp Gly Leu Glu Thr Arg Thr Arg Gln Ile
                165                 170                 175

Val Lys Lys Pro Val Lys Asp Thr Ile Leu Cys Pro Thr Ile Ala Glu
            180                 185                 190

Ser Arg Arg Cys Lys Met Thr Met Arg His Cys Pro Gly Gly Lys Arg
        195                 200                 205

Thr Pro Lys Ala Lys Glu Lys Arg Asn Lys Lys Lys Arg Lys Leu
210                 215                 220

Ile Glu Arg Ala Gln Glu Gln His Ser Val Phe Leu Ala Thr Asp Arg
225                 230                 235                 240

Ala Asn Gln

<210> SEQ ID NO 12
<211> LENGTH: 272
<212> TYPE: PRT
<213> ORGANISM: Homo sapiens

<400> SEQUENCE: 12

Met His Leu Arg Leu Ile Ser Trp Leu Phe Ile Ile Leu Asn Phe Met
1               5                   10                  15
```

Glu Tyr Ile Gly Ser Gln Asn Ala Ser Arg Gly Arg Gln Arg Arg
            20                  25                  30

Met His Pro Asn Val Ser Gln Gly Cys Gln Gly Gly Cys Ala Thr Cys
            35                  40                  45

Ser Asp Tyr Asn Gly Cys Leu Ser Cys Lys Pro Arg Leu Phe Phe Ala
50                  55                  60

Leu Glu Arg Ile Gly Met Lys Gln Ile Gly Val Cys Leu Ser Ser Cys
65                  70                  75                  80

Pro Ser Gly Tyr Tyr Gly Thr Arg Tyr Pro Asp Ile Asn Lys Cys Thr
                85                  90                  95

Lys Cys Lys Ala Asp Cys Asp Thr Cys Phe Asn Lys Asn Phe Cys Thr
            100                 105                 110

Lys Cys Lys Ser Gly Phe Tyr Leu His Leu Gly Lys Cys Leu Asp Asn
            115                 120                 125

Cys Pro Glu Gly Leu Glu Ala Asn Asn His Thr Met Glu Cys Val Ser
130                 135                 140

Ile Val His Cys Glu Val Ser Glu Trp Asn Pro Trp Ser Pro Cys Thr
145                 150                 155                 160

Lys Lys Gly Lys Thr Cys Gly Phe Lys Arg Gly Thr Glu Thr Arg Val
                165                 170                 175

Arg Glu Ile Ile Gln His Pro Ser Ala Lys Gly Asn Leu Cys Pro Pro
            180                 185                 190

Thr Asn Glu Thr Arg Lys Cys Thr Val Gln Arg Lys Lys Cys Gln Lys
            195                 200                 205

Gly Glu Arg Gly Lys Lys Gly Arg Glu Arg Lys Arg Lys Lys Pro Asn
            210                 215                 220

Lys Gly Glu Ser Lys Glu Ala Ile Pro Asp Ser Lys Ser Leu Glu Ser
225                 230                 235                 240

Ser Lys Glu Ile Pro Glu Gln Arg Glu Asn Lys Gln Gln Gln Lys Lys
                245                 250                 255

Arg Lys Val Gln Asp Lys Gln Lys Ser Val Ser Val Ser Thr Val His
            260                 265                 270

<210> SEQ ID NO 13
<211> LENGTH: 234
<212> TYPE: PRT
<213> ORGANISM: Homo sapiens

<400> SEQUENCE: 13

Met Arg Ala Pro Leu Cys Leu Leu Leu Leu Val Ala His Ala Val Asp
1               5                   10                  15

Met Leu Ala Leu Asn Arg Arg Lys Lys Gln Val Gly Thr Gly Leu Gly
            20                  25                  30

Gly Asn Cys Thr Gly Cys Ile Ile Cys Ser Glu Glu Asn Gly Cys Ser
            35                  40                  45

Thr Cys Gln Gln Arg Leu Phe Leu Phe Ile Arg Arg Glu Gly Ile Arg
            50                  55                  60

Gln Tyr Gly Lys Cys Leu His Asp Cys Pro Pro Gly Tyr Phe Gly Ile
65                  70                  75                  80

Arg Gly Gln Glu Val Asn Arg Cys Lys Lys Cys Gly Ala Thr Cys Glu
                85                  90                  95

Ser Cys Phe Ser Gln Asp Phe Cys Ile Arg Cys Lys Arg Gln Phe Tyr
            100                 105                 110

Leu Tyr Lys Gly Lys Cys Leu Pro Thr Cys Pro Pro Gly Thr Leu Ala

```
            115                 120                 125
His Gln Asn Thr Arg Glu Cys Gln Gly Glu Cys Glu Leu Gly Pro Trp
    130                 135                 140

Gly Gly Trp Ser Pro Cys Thr His Asn Gly Lys Thr Cys Gly Ser Ala
145                 150                 155                 160

Trp Gly Leu Glu Ser Arg Val Arg Glu Ala Gly Arg Ala Gly His Glu
                165                 170                 175

Glu Ala Ala Thr Cys Gln Val Leu Ser Glu Ser Arg Lys Cys Pro Ile
            180                 185                 190

Gln Arg Pro Cys Pro Gly Glu Arg Ser Pro Gly Gln Lys Lys Gly Arg
        195                 200                 205

Lys Asp Arg Arg Pro Arg Lys Asp Arg Lys Leu Asp Arg Arg Leu Asp
    210                 215                 220

Val Arg Pro Arg Gln Pro Gly Leu Gln Pro
225                 230

<210> SEQ ID NO 14
<211> LENGTH: 172
<212> TYPE: PRT
<213> ORGANISM: Homo sapiens

<400> SEQUENCE: 14

Met Arg Ala Pro Leu Cys Leu Leu Leu Val Ala His Ala Val Asp
1               5                   10                  15

Met Leu Ala Leu Asn Arg Arg Lys Lys Gln Val Gly Thr Gly Leu Gly
            20                  25                  30

Gly Asn Cys Thr Gly Cys Ile Ile Cys Ser Glu Glu Asn Gly Cys Ser
        35                  40                  45

Thr Cys Gln Gln Arg Leu Phe Leu Phe Ile Arg Arg Glu Gly Ile Arg
    50                  55                  60

Gln Tyr Gly Lys Cys Leu His Asp Cys Pro Pro Gly Tyr Phe Gly Ile
65                  70                  75                  80

Arg Gly Gln Glu Val Asn Arg Cys Lys Lys Cys Gly Ala Thr Cys Glu
                85                  90                  95

Ser Cys Phe Ser Gln Asp Phe Cys Ile Arg Cys Lys Arg Gln Phe Tyr
            100                 105                 110

Leu Tyr Lys Gly Lys Cys Leu Pro Thr Cys Pro Pro Gly Thr Leu Ala
        115                 120                 125

His Gln Asn Thr Arg Glu Cys Gln Glu Arg Ser Pro Gly Gln Lys Lys
    130                 135                 140

Gly Arg Lys Asp Arg Arg Pro Arg Lys Asp Arg Lys Leu Asp Arg Arg
145                 150                 155                 160

Leu Asp Val Arg Pro Arg Gln Pro Gly Leu Gln Pro
                165                 170

<210> SEQ ID NO 15
<211> LENGTH: 133
<212> TYPE: PRT
<213> ORGANISM: Homo sapiens

<400> SEQUENCE: 15

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
```

```
                35                  40                  45
Ser His Pro Leu Tyr Lys Cys Ser Ser Lys Met Val Leu Leu Ala Arg
 50                  55                  60

Cys Glu Gly His Cys Ser Gln Ala Ser Arg Ser Glu Pro Leu Val Ser
 65                  70                  75                  80

Phe Ser Thr Val Leu Lys Gln Pro Phe Arg Ser Ser Cys His Cys Cys
                 85                  90                  95

Arg Pro Gln Thr Ser Lys Leu Lys Ala Leu Arg Leu Arg Cys Ser Gly
                100                 105                 110

Gly Met Arg Leu Thr Ala Thr Tyr Arg Tyr Ile Leu Ser Cys His Cys
                115                 120                 125

Glu Glu Cys Asn Ser
                130

<210> SEQ ID NO 16
<211> LENGTH: 352
<212> TYPE: PRT
<213> ORGANISM: Homo sapiens

<400> SEQUENCE: 16

Met Ala Pro Leu Gly Tyr Phe Leu Leu Leu Cys Ser Leu Lys Gln Ala
  1               5                  10                  15

Leu Gly Ser Tyr Pro Ile Trp Trp Ser Leu Ala Val Gly Pro Gln Tyr
                 20                  25                  30

Ser Ser Leu Gly Ser Gln Pro Ile Leu Cys Ala Ser Ile Pro Gly Leu
                 35                  40                  45

Val Pro Lys Gln Leu Arg Phe Cys Arg Asn Tyr Val Glu Ile Met Pro
 50                  55                  60

Ser Val Ala Glu Gly Ile Lys Ile Gly Ile Gln Glu Cys Gln His Gln
 65                  70                  75                  80

Phe Arg Gly Arg Arg Trp Asn Cys Thr Thr Val His Asp Ser Leu Ala
                 85                  90                  95

Ile Phe Gly Pro Val Leu Asp Lys Ala Thr Arg Glu Ser Ala Phe Val
                100                 105                 110

His Ala Ile Ala Ser Ala Gly Val Ala Phe Ala Val Thr Arg Ser Cys
                115                 120                 125

Ala Glu Gly Thr Ala Ala Ile Cys Gly Cys Ser Ser Arg His Gln Gly
                130                 135                 140

Ser Pro Gly Lys Gly Trp Lys Trp Gly Gly Cys Ser Glu Asp Ile Glu
145                 150                 155                 160

Phe Gly Gly Met Val Ser Arg Glu Phe Ala Asp Ala Arg Glu Asn Arg
                165                 170                 175

Pro Asp Ala Arg Ser Ala Met Asn Arg His Asn Asn Glu Ala Gly Arg
                180                 185                 190

Gln Ala Ile Ala Ser His Met His Leu Lys Cys Lys Cys His Gly Leu
                195                 200                 205

Ser Gly Ser Cys Glu Val Lys Thr Cys Trp Trp Ser Gln Pro Asp Phe
                210                 215                 220

Arg Ala Ile Gly Asp Phe Leu Lys Asp Lys Tyr Asp Ser Ala Ser Glu
225                 230                 235                 240

Met Val Val Glu Lys His Arg Glu Ser Arg Gly Trp Val Glu Thr Leu
                245                 250                 255

Arg Pro Arg Tyr Thr Tyr Phe Lys Val Pro Thr Glu Arg Asp Leu Val
                260                 265                 270
```

```
Tyr Tyr Glu Ala Ser Pro Asn Phe Cys Glu Pro Asn Pro Glu Thr Gly
            275                 280                 285

Ser Phe Gly Thr Arg Asp Arg Thr Cys Asn Val Ser Ser His Gly Ile
    290                 295                 300

Asp Gly Cys Asp Leu Leu Cys Cys Gly Arg Gly His Asn Ala Arg Ala
305                 310                 315                 320

Glu Arg Arg Arg Glu Lys Cys Arg Cys Val Phe His Trp Cys Cys Tyr
                325                 330                 335

Val Ser Cys Gln Glu Cys Thr Arg Val Tyr Asp Val His Thr Cys Lys
                340                 345                 350
```

<210> SEQ ID NO 17
<211> LENGTH: 338
<212> TYPE: PRT
<213> ORGANISM: Homo sapiens

<400> SEQUENCE: 17

```
Ala Val Gly Ser Pro Leu Val Met Asp Pro Thr Ser Ile Cys Arg Lys
1               5                   10                  15

Ala Arg Arg Leu Ala Gly Arg Gln Ala Glu Leu Cys Gln Ala Glu Pro
                20                  25                  30

Glu Val Val Ala Glu Leu Ala Arg Gly Ala Arg Leu Gly Val Arg Glu
            35                  40                  45

Cys Gln Phe Gln Phe Arg Phe Arg Arg Trp Asn Cys Ser Ser His Ser
    50                  55                  60

Lys Ala Phe Gly Arg Ile Leu Gln Gln Asp Ile Arg Glu Thr Ala Phe
65                  70                  75                  80

Val Phe Ala Ile Thr Ala Ala Gly Ala Ser His Ala Val Thr Gln Ala
                85                  90                  95

Cys Ser Met Gly Glu Leu Leu Gln Cys Gly Cys Gln Ala Pro Arg Gly
                100                 105                 110

Arg Ala Pro Pro Arg Pro Ser Gly Leu Pro Gly Thr Pro Gly Pro Pro
            115                 120                 125

Gly Pro Ala Gly Ser Pro Glu Gly Ser Ala Ala Trp Glu Trp Gly Gly
    130                 135                 140

Cys Gly Asp Asp Val Asp Phe Gly Asp Glu Lys Ser Arg Leu Phe Met
145                 150                 155                 160

Asp Ala Arg His Lys Arg Gly Arg Gly Asp Ile Arg Ala Leu Val Gln
                165                 170                 175

Leu His Asn Asn Glu Ala Gly Arg Leu Ala Val Arg Ser His Thr Arg
            180                 185                 190

Thr Glu Cys Lys Cys His Gly Leu Ser Gly Ser Cys Ala Leu Arg Thr
    195                 200                 205

Cys Trp Gln Lys Leu Pro Pro Phe Arg Glu Val Gly Ala Arg Leu Leu
210                 215                 220

Glu Arg Phe His Gly Ala Ser Arg Val Met Gly Thr Asn Asp Gly Lys
225                 230                 235                 240

Ala Leu Leu Pro Ala Val Arg Thr Leu Lys Pro Pro Gly Arg Ala Asp
                245                 250                 255

Leu Leu Tyr Ala Ala Asp Ser Pro Asp Phe Cys Ala Pro Asn Arg Arg
            260                 265                 270

Thr Gly Ser Pro Gly Thr Arg Gly Arg Ala Cys Asn Ser Ser Ala Pro
    275                 280                 285

Asp Leu Ser Gly Cys Asp Leu Leu Cys Cys Gly Arg Gly His Arg Gln
290                 295                 300
```

```
Glu Ser Val Gln Leu Glu Glu Asn Cys Leu Cys Arg Phe His Trp Cys
305                 310                 315                 320

Cys Val Val Gln Cys His Arg Cys Arg Val Arg Lys Glu Leu Ser Leu
                325                 330                 335

Cys Leu

<210> SEQ ID NO 18
<211> LENGTH: 288
<212> TYPE: PRT
<213> ORGANISM: Homo sapiens

<400> SEQUENCE: 18

Met Val Gly Val Gly Gly Asp Val Glu Asp Val Thr Pro Arg Pro
1               5                   10                  15

Gly Gly Cys Gln Ile Ser Gly Arg Gly Ala Arg Gly Cys Asn Gly Ile
                20                  25                  30

Pro Gly Ala Ala Ala Trp Glu Ala Ala Leu Pro Arg Arg Arg Pro Arg
            35                  40                  45

Arg His Pro Ser Val Asn Pro Arg Ser Arg Ala Ala Gly Ser Pro Arg
        50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Gly Arg
                85                  90                  95

Gly Arg Gly Arg Ala Pro Glu Arg Val Gly Gly Arg Gly Arg Gly Arg
                100                 105                 110

Gly Thr Ala Ala Pro Arg Ala Ala Pro Ala Ala Arg Gly Ser Arg Pro
            115                 120                 125

Gly Pro Ala Gly Thr Met Ala Ala Gly Ser Ile Thr Thr Leu Pro Ala
130                 135                 140

Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
                180                 185                 190

Ile Lys Leu Gln Leu Gln Ala Glu Glu Arg Gly Val Val Ser Ile Lys
            195                 200                 205

Gly Val Cys Ala Asn Arg Tyr Leu Ala Met Lys Glu Asp Gly Arg Leu
210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
            260                 265                 270

Gly Pro Gly Gln Lys Ala Ile Leu Phe Leu Pro Met Ser Ala Lys Ser
275                 280                 285

<210> SEQ ID NO 19
<211> LENGTH: 194
<212> TYPE: PRT
<213> ORGANISM: Homo sapiens

<400> SEQUENCE: 19
```

```
Met His Lys Trp Ile Leu Thr Trp Ile Leu Pro Thr Leu Leu Tyr Arg
1               5                   10                  15

Ser Cys Phe His Ile Ile Cys Leu Val Gly Thr Ile Ser Leu Ala Cys
                20                  25                  30

Asn Asp Met Thr Pro Glu Gln Met Ala Thr Asn Val Asn Cys Ser Ser
            35                  40                  45

Pro Glu Arg His Thr Arg Ser Tyr Asp Tyr Met Glu Gly Gly Asp Ile
        50                  55                  60

Arg Val Arg Arg Leu Phe Cys Arg Thr Gln Trp Tyr Leu Arg Ile Asp
65                  70                  75                  80

Lys Arg Gly Lys Val Lys Gly Thr Gln Glu Met Lys Asn Asn Tyr Asn
                85                  90                  95

Ile Met Glu Ile Arg Thr Val Ala Val Gly Ile Val Ala Ile Lys Gly
            100                 105                 110

Val Glu Ser Glu Phe Tyr Leu Ala Met Asn Lys Glu Gly Lys Leu Tyr
        115                 120                 125

Ala Lys Lys Glu Cys Asn Glu Asp Cys Asn Phe Lys Glu Leu Ile Leu
    130                 135                 140

Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
                165                 170                 175

Lys Lys Thr Lys Lys Glu Gln Lys Thr Ala His Phe Leu Pro Met Ala
            180                 185                 190

Ile Thr

<210> SEQ ID NO 20
<211> LENGTH: 208
<212> TYPE: PRT
<213> ORGANISM: Homo sapiens

<400> SEQUENCE: 20

Met Trp Lys Trp Ile Leu Thr His Cys Ala Ser Ala Phe Pro His Leu
1               5                   10                  15

Pro Gly Cys Cys Cys Cys Phe Leu Leu Phe Leu Val Ser Ser
                20                  25                  30

Val Pro Val Thr Cys Gln Ala Leu Gly Gln Val Met Val Ser Pro Glu
            35                  40                  45

Ala Thr Asn Ser Ser Ser Ser Phe Ser Ser Pro Ser Ser Ala Gly
    50                  55                  60

Arg His Val Arg Ser Tyr Asn His Leu Gln Gly Asp Val Arg Trp Arg
65                  70                  75                  80

Lys Leu Phe Ser Phe Thr Lys Tyr Phe Leu Lys Ile Glu Lys Asn Gly
                85                  90                  95

Lys Val Ser Gly Thr Lys Lys Glu Asn Cys Pro Tyr Ser Ile Leu Glu
            100                 105                 110

Ile Thr Ser Val Glu Ile Gly Val Val Ala Val Lys Ala Ile Asn Ser
        115                 120                 125

Asn Tyr Tyr Leu Ala Met Asn Lys Lys Gly Lys Leu Tyr Gly Ser Lys
    130                 135                 140

Glu Phe Asn Asn Asp Cys Lys Leu Lys Glu Arg Ile Glu Glu Asn Gly
145                 150                 155                 160

Tyr Asn Thr Tyr Ala Ser Phe Asn Trp Gln His Asn Gly Arg Gln Met
                165                 170                 175
```

```
Tyr Val Ala Leu Asn Gly Lys Gly Ala Pro Arg Arg Gly Gln Lys Thr
            180                 185                 190

Arg Arg Lys Asn Thr Ser Ala His Phe Leu Pro Met Val Val His Ser
        195                 200                 205
```

<210> SEQ ID NO 21
<211> LENGTH: 1207
<212> TYPE: PRT
<213> ORGANISM: Homo sapiens

<400> SEQUENCE: 21

```
Met Leu Leu Thr Leu Ile Ile Leu Leu Pro Val Val Ser Lys Phe Ser
1               5                   10                  15

Phe Val Ser Leu Ser Ala Pro Gln His Trp Ser Cys Pro Glu Gly Thr
            20                  25                  30

Leu Ala Gly Asn Gly Asn Ser Thr Cys Val Gly Pro Ala Pro Phe Leu
        35                  40                  45

Ile Phe Ser His Gly Asn Ser Ile Phe Arg Ile Asp Thr Glu Gly Thr
50                  55                  60

Asn Tyr Glu Gln Leu Val Val Asp Ala Gly Val Ser Val Ile Met Asp
65                  70                  75                  80

Phe His Tyr Asn Glu Lys Arg Ile Tyr Trp Val Asp Leu Glu Arg Gln
                85                  90                  95

Leu Leu Gln Arg Val Phe Leu Asn Gly Ser Arg Gln Glu Arg Val Cys
            100                 105                 110

Asn Ile Glu Lys Asn Val Ser Gly Met Ala Ile Asn Trp Ile Asn Glu
        115                 120                 125

Glu Val Ile Trp Ser Asn Gln Gln Glu Gly Ile Ile Thr Val Thr Asp
130                 135                 140

Met Lys Gly Asn Asn Ser His Ile Leu Leu Ser Ala Leu Lys Tyr Pro
145                 150                 155                 160

Ala Asn Val Ala Val Asp Pro Val Glu Arg Phe Ile Phe Trp Ser Ser
                165                 170                 175

Glu Val Ala Gly Ser Leu Tyr Arg Ala Asp Leu Asp Gly Val Gly Val
            180                 185                 190

Lys Ala Leu Leu Glu Thr Ser Glu Lys Ile Thr Ala Val Ser Leu Asp
        195                 200                 205

Val Leu Asp Lys Arg Leu Phe Trp Ile Gln Tyr Asn Arg Glu Gly Ser
210                 215                 220

Asn Ser Leu Ile Cys Ser Cys Asp Tyr Asp Gly Gly Ser Val His Ile
225                 230                 235                 240

Ser Lys His Pro Thr Gln His Asn Leu Phe Ala Met Ser Leu Phe Gly
                245                 250                 255

Asp Arg Ile Phe Tyr Ser Thr Trp Lys Met Lys Thr Ile Trp Ile Ala
            260                 265                 270

Asn Lys His Thr Gly Lys Asp Met Val Arg Ile Asn Leu His Ser Ser
        275                 280                 285

Phe Val Pro Leu Gly Glu Leu Lys Val Val His Pro Leu Ala Gln Pro
290                 295                 300

Lys Ala Glu Asp Asp Thr Trp Glu Pro Glu Gln Lys Leu Cys Lys Leu
305                 310                 315                 320

Arg Lys Gly Asn Cys Ser Ser Thr Val Cys Gly Gln Asp Leu Gln Ser
                325                 330                 335

His Leu Cys Met Cys Ala Glu Gly Tyr Ala Leu Ser Arg Asp Arg Lys
            340                 345                 350
```

```
Tyr Cys Glu Asp Val Asn Glu Cys Ala Phe Trp Asn His Gly Cys Thr
        355                 360                 365
Leu Gly Cys Lys Asn Thr Pro Gly Ser Tyr Tyr Cys Thr Cys Pro Val
    370                 375                 380
Gly Phe Val Leu Leu Pro Asp Gly Lys Arg Cys His Gln Leu Val Ser
385                 390                 395                 400
Cys Pro Arg Asn Val Ser Glu Cys Ser His Asp Cys Val Leu Thr Ser
                405                 410                 415
Glu Gly Pro Leu Cys Phe Cys Pro Glu Gly Ser Val Leu Glu Arg Asp
                420                 425                 430
Gly Lys Thr Cys Ser Gly Cys Ser Ser Pro Asp Asn Gly Gly Cys Ser
            435                 440                 445
Gln Leu Cys Val Pro Leu Ser Pro Val Ser Trp Glu Cys Asp Cys Phe
    450                 455                 460
Pro Gly Tyr Asp Leu Gln Leu Asp Glu Lys Ser Cys Ala Ala Ser Gly
465                 470                 475                 480
Pro Gln Pro Phe Leu Leu Phe Ala Asn Ser Gln Asp Ile Arg His Met
                485                 490                 495
His Phe Asp Gly Thr Asp Tyr Gly Thr Leu Leu Ser Gln Gln Met Gly
                500                 505                 510
Met Val Tyr Ala Leu Asp His Asp Pro Val Glu Asn Lys Ile Tyr Phe
            515                 520                 525
Ala His Thr Ala Leu Lys Trp Ile Glu Arg Ala Asn Met Asp Gly Ser
        530                 535                 540
Gln Arg Glu Arg Leu Ile Glu Glu Gly Val Asp Val Pro Glu Gly Leu
545                 550                 555                 560
Ala Val Asp Trp Ile Gly Arg Arg Phe Tyr Trp Thr Asp Arg Gly Lys
                565                 570                 575
Ser Leu Ile Gly Arg Ser Asp Leu Asn Gly Lys Arg Ser Lys Ile Ile
                580                 585                 590
Thr Lys Glu Asn Ile Ser Gln Pro Arg Gly Ile Ala Val His Pro Met
            595                 600                 605
Ala Lys Arg Leu Phe Trp Thr Asp Thr Gly Ile Asn Pro Arg Ile Glu
        610                 615                 620
Ser Ser Ser Leu Gln Gly Leu Gly Arg Leu Val Ile Ala Ser Ser Asp
625                 630                 635                 640
Leu Ile Trp Pro Ser Gly Ile Thr Ile Asp Phe Leu Thr Asp Lys Leu
                645                 650                 655
Tyr Trp Cys Asp Ala Lys Gln Ser Val Ile Glu Met Ala Asn Leu Asp
                660                 665                 670
Gly Ser Lys Arg Arg Arg Leu Thr Gln Asn Asp Val Gly His Pro Phe
            675                 680                 685
Ala Val Ala Val Phe Glu Asp Tyr Val Trp Phe Ser Asp Trp Ala Met
        690                 695                 700
Pro Ser Val Met Arg Val Asn Lys Arg Thr Gly Lys Asp Arg Val Arg
705                 710                 715                 720
Leu Gln Gly Ser Met Leu Lys Pro Ser Ser Leu Val Val Val His Pro
                725                 730                 735
Leu Ala Lys Pro Gly Ala Asp Pro Cys Leu Tyr Gln Asn Gly Gly Cys
            740                 745                 750
Glu His Ile Cys Lys Lys Arg Leu Gly Thr Ala Trp Cys Ser Cys Arg
        755                 760                 765
```

```
Glu Gly Phe Met Lys Ala Ser Asp Gly Lys Thr Cys Leu Ala Leu Asp
770                 775                 780

Gly His Gln Leu Leu Ala Gly Glu Val Asp Leu Lys Asn Gln Val
785                 790                 795                 800

Thr Pro Leu Asp Ile Leu Ser Lys Thr Arg Val Ser Glu Asp Asn Ile
                805                 810                 815

Thr Glu Ser Gln His Met Leu Val Ala Glu Ile Met Val Ser Asp Gln
                820                 825                 830

Asp Asp Cys Ala Pro Val Gly Cys Ser Met Tyr Ala Arg Cys Ile Ser
                835                 840                 845

Glu Gly Glu Asp Ala Thr Cys Gln Cys Leu Lys Gly Phe Ala Gly Asp
850                 855                 860

Gly Lys Leu Cys Ser Asp Ile Asp Glu Cys Glu Met Gly Val Pro Val
865                 870                 875                 880

Cys Pro Pro Ala Ser Ser Lys Cys Ile Asn Thr Glu Gly Gly Tyr Val
                885                 890                 895

Cys Arg Cys Ser Glu Gly Tyr Gln Gly Asp Gly Ile His Cys Leu Asp
                900                 905                 910

Ile Asp Glu Cys Gln Leu Gly Glu His Ser Cys Gly Glu Asn Ala Ser
                915                 920                 925

Cys Thr Asn Thr Glu Gly Gly Tyr Thr Cys Met Cys Ala Gly Arg Leu
930                 935                 940

Ser Glu Pro Gly Leu Ile Cys Pro Asp Ser Thr Pro Pro His Leu
945                 950                 955                 960

Arg Glu Asp Asp His His Tyr Ser Val Arg Asn Ser Asp Ser Glu Cys
                965                 970                 975

Pro Leu Ser His Asp Gly Tyr Cys Leu His Asp Gly Val Cys Met Tyr
                980                 985                 990

Ile Glu Ala Leu Asp Lys Tyr Ala Cys Asn Cys Val Val Gly Tyr Ile
                995                 1000                1005

Gly Glu Arg Cys Gln Tyr Arg Asp Leu Lys Trp Trp Glu Leu Arg
        1010                1015                1020

His Ala Gly His Gly Gln Gln Gln Lys Val Ile Val Val Ala Val
        1025                1030                1035

Cys Val Val Val Leu Val Met Leu Leu Leu Leu Ser Leu Trp Gly
        1040                1045                1050

Ala His Tyr Tyr Arg Thr Gln Lys Leu Leu Ser Lys Asn Pro Lys
        1055                1060                1065

Asn Pro Tyr Glu Glu Ser Ser Arg Asp Val Arg Ser Arg Arg Pro
        1070                1075                1080

Ala Asp Thr Glu Asp Gly Met Ser Ser Cys Pro Gln Pro Trp Phe
        1085                1090                1095

Val Val Ile Lys Glu His Gln Asp Leu Lys Asn Gly Gly Gln Pro
        1100                1105                1110

Val Ala Gly Glu Asp Gly Gln Ala Ala Asp Gly Ser Met Gln Pro
        1115                1120                1125

Thr Ser Trp Arg Gln Glu Pro Gln Leu Cys Gly Met Gly Thr Glu
        1130                1135                1140

Gln Gly Cys Trp Ile Pro Val Ser Ser Asp Lys Gly Ser Cys Pro
        1145                1150                1155

Gln Val Met Glu Arg Ser Phe His Met Pro Ser Tyr Gly Thr Gln
        1160                1165                1170

Thr Leu Glu Gly Gly Val Glu Lys Pro His Ser Leu Leu Ser Ala
```

```
                1175                1180                1185
Asn Pro Leu Trp Gln Gln Arg Ala Leu Asp Pro Pro His Gln Met
            1190                1195                1200

Glu Leu Thr Gln
        1205

<210> SEQ ID NO 22
<211> LENGTH: 160
<212> TYPE: PRT
<213> ORGANISM: Homo sapiens

<400> SEQUENCE: 22

Met Val Pro Ser Ala Gly Gln Leu Ala Leu Phe Ala Leu Gly Ile Val
1               5                   10                  15

Leu Ala Ala Cys Gln Ala Leu Glu Asn Ser Thr Ser Pro Leu Ser Ala
                20                  25                  30

Asp Pro Pro Val Ala Ala Val Val Ser His Phe Asn Asp Cys Pro
            35                  40                  45

Asp Ser His Thr Gln Phe Cys Phe His Gly Thr Cys Arg Phe Leu Val
        50                  55                  60

Gln Glu Asp Lys Pro Ala Cys Val Cys His Ser Gly Tyr Val Gly Ala
65                  70                  75                  80

Arg Cys Glu His Ala Asp Leu Leu Ala Val Val Ala Ala Ser Gln Lys
                85                  90                  95

Lys Gln Ala Ile Thr Ala Leu Val Val Val Ser Ile Val Ala Leu Ala
                100                 105                 110

Val Leu Ile Ile Thr Cys Val Leu Ile His Cys Cys Gln Val Arg Lys
                115                 120                 125

His Cys Glu Trp Cys Arg Ala Leu Ile Cys Arg His Glu Lys Pro Ser
                130                 135                 140

Ala Leu Leu Lys Gly Arg Thr Ala Cys Cys His Ser Glu Thr Val Val
145                 150                 155                 160

<210> SEQ ID NO 23
<211> LENGTH: 159
<212> TYPE: PRT
<213> ORGANISM: Artificial sequence
<220> FEATURE:
<223> OTHER INFORMATION: Synthetic peptide

<400> SEQUENCE: 23

Met Val Pro Ser Ala Gly Gln Leu Ala Leu Phe Ala Leu Gly Ile Val
1               5                   10                  15

Leu Ala Ala Cys Gln Ala Leu Glu Asn Ser Thr Ser Pro Leu Ser Asp
                20                  25                  30

Pro Pro Val Ala Ala Val Val Ser His Phe Asn Asp Cys Pro Asp
            35                  40                  45

Ser His Thr Gln Phe Cys Phe His Gly Thr Cys Arg Phe Leu Val Gln
        50                  55                  60

Glu Asp Lys Pro Ala Cys Val Cys His Ser Gly Tyr Val Gly Ala Arg
65                  70                  75                  80

Cys Glu His Ala Asp Leu Leu Ala Val Val Ala Ala Ser Gln Lys Lys
                85                  90                  95

Gln Ala Ile Thr Ala Leu Val Val Val Ser Ile Val Ala Leu Ala Val
                100                 105                 110

Leu Ile Ile Thr Cys Val Leu Ile His Cys Cys Gln Val Arg Lys His
                115                 120                 125
```

-continued

Cys Glu Trp Cys Arg Ala Leu Ile Cys Arg His Glu Lys Pro Ser Ala
         130                 135                 140

Leu Leu Lys Gly Arg Thr Ala Cys Cys His Ser Glu Thr Val Val
145                 150                 155

<210> SEQ ID NO 24
<211> LENGTH: 160
<212> TYPE: PRT
<213> ORGANISM: Artificial sequence
<220> FEATURE:
<223> OTHER INFORMATION: Synthetic peptide

<400> SEQUENCE: 24

Met Val Pro Leu Ala Gly Gln Leu Ala Leu Phe Ala Leu Gly Ile Val
1               5                   10                  15

Leu Ala Ala Cys Gln Ala Leu Glu Asn Ser Thr Ser Pro Leu Ser Asp
                20                  25                  30

Pro Pro Val Ala Ala Ala Val Val Ser His Phe Asn Asp Cys Pro Asp
            35                  40                  45

Ser His Thr Gln Phe Cys Phe His Gly Thr Cys Arg Phe Leu Val Gln
        50                  55                  60

Glu Asp Lys Pro Ala Cys Val Cys His Ser Gly Tyr Val Gly Ala Arg
65                  70                  75                  80

Cys Glu His Ala Asp Leu Leu Ala Val Val Ala Ala Ser Gln Lys Lys
                85                  90                  95

Gln Ala Ile Thr Ala Leu Val Val Val Ser Ile Val Ala Leu Ala Val
                100                 105                 110

Leu Ile Ile Thr Cys Val Leu Ile His Cys Cys Gln Val Arg Lys His
            115                 120                 125

Cys Glu Trp Cys Arg Ala Leu Ile Cys Arg His Glu Lys Pro Ser Ala
         130                 135                 140

Leu Leu Lys Gly Arg Thr Ala Cys Cys His Ser Glu Thr Val Val Leu
145                 150                 155                 160

<210> SEQ ID NO 25
<211> LENGTH: 50
<212> TYPE: PRT
<213> ORGANISM: Homo sapiens

<400> SEQUENCE: 25

Val Val Ser His Phe Asn Asp Cys Pro Asp Ser His Thr Gln Phe Cys
1               5                   10                  15

Phe His Gly Thr Cys Arg Phe Leu Val Gln Glu Asp Lys Pro Ala Cys
                20                  25                  30

Val Cys His Ser Gly Tyr Val Gly Ala Arg Cys Glu His Ala Asp Leu
            35                  40                  45

Leu Ala
     50

<210> SEQ ID NO 26
<211> LENGTH: 246
<212> TYPE: PRT
<213> ORGANISM: Homo sapiens

<400> SEQUENCE: 26

Met Thr Ile Leu Phe Leu Thr Met Val Ile Ser Tyr Phe Gly Cys Met
1               5                   10                  15

Lys Ala Ala Pro Met Lys Glu Ala Ile Arg Gly Gln Gly Gly Leu Ala

```
            20                  25                  30
Tyr Pro Gly Val Arg Thr His Gly Thr Leu Glu Ser Val Asn Gly Pro
        35                  40                  45

Lys Ala Gly Ser Arg Gly Leu Thr Ser Leu Ala Asp Thr Phe Glu His
 50                  55                  60

Val Ile Glu Glu Leu Leu Asp Glu Asp Gln Lys Val Arg Pro Asn Glu
 65                  70                  75                  80

Glu Asn Asn Lys Asp Ala Asp Leu Tyr Thr Ser Arg Val Met Leu Ser
                 85                  90                  95

Ser Gln Val Pro Leu Glu Pro Pro Leu Leu Phe Leu Leu Glu Glu Tyr
                100                 105                 110

Lys Asn Tyr Leu Asp Ala Ala Asn Met Ser Met Arg Val Arg Arg His
            115                 120                 125

Ser Asp Pro Ala Arg Arg Gly Glu Leu Ser Val Cys Asp Ser Ile Ser
        130                 135                 140

Glu Trp Val Thr Ala Ala Asp Lys Lys Thr Ala Val Asp Met Ser Gly
145                 150                 155                 160

Gly Thr Val Thr Val Leu Glu Lys Val Pro Val Ser Lys Gly Gln Leu
                165                 170                 175

Lys Gln Tyr Phe Tyr Glu Thr Lys Cys Asn Pro Met Gly Tyr Thr Lys
            180                 185                 190

Glu Gly Cys Arg Gly Ile Asp Lys Arg His Trp Asn Ser Gln Cys Arg
        195                 200                 205

Thr Thr Gln Ser Tyr Val Arg Ala Leu Thr Met Asp Ser Lys Lys Arg
    210                 215                 220

Ile Gly Trp Arg Phe Ile Arg Ile Asp Thr Ser Cys Val Cys Thr Leu
225                 230                 235                 240

Thr Ile Lys Arg Gly Arg
                245

<210> SEQ ID NO 27
<211> LENGTH: 194
<212> TYPE: PRT
<213> ORGANISM: Homo sapiens

<400> SEQUENCE: 27

Met His Lys Trp Ile Leu Thr Trp Ile Leu Pro Thr Leu Leu Tyr Arg
 1               5                  10                  15

Ser Cys Phe His Ile Ile Cys Leu Val Gly Thr Ile Ser Leu Ala Cys
                20                  25                  30

Asn Asp Met Thr Pro Glu Gln Met Ala Thr Asn Val Asn Cys Ser Ser
            35                  40                  45

Pro Glu Arg His Thr Arg Ser Tyr Asp Tyr Met Glu Gly Gly Asp Ile
 50                  55                  60

Arg Val Arg Arg Leu Phe Cys Arg Thr Gln Trp Tyr Leu Arg Ile Asp
 65                  70                  75                  80

Lys Arg Gly Lys Val Lys Gly Thr Gln Glu Met Lys Asn Asn Tyr Asn
                 85                  90                  95

Ile Met Glu Ile Arg Thr Val Ala Val Gly Ile Val Ala Ile Lys Gly
                100                 105                 110

Val Glu Ser Glu Phe Tyr Leu Ala Met Asn Lys Glu Gly Lys Leu Tyr
            115                 120                 125

Ala Lys Lys Glu Cys Asn Glu Asp Cys Asn Phe Lys Glu Leu Ile Leu
        130                 135                 140
```

Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
            165                 170                 175

Lys Lys Thr Lys Lys Glu Gln Lys Thr Ala His Phe Leu Pro Met Ala
            180                 185                 190

Ile Thr

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36
<211> LENGTH: 17
<212> TYPE: PRT

```
<213> ORGANISM: Artificial sequence
<220> FEATURE:
<223> OTHER INFORMATION: Synthetic peptide

<400> SEQUENCE: 36

Cys Asp Asp Tyr Tyr Tyr Gly Phe Gly Cys Asn Lys Phe Cys Arg Pro
1               5                   10                  15

Arg
```

STEM CELL CULTURE SYSTEMS FOR COLUMNAR EPITHELIAL STEM CELLS, AND USES RELATED THERETO

CROSS REFERENCE TO RELATED APPLICATIONS

This application is a national phase application under 35 U.S.C. § 371 of International Application No. PCT/US2018/067858, filed Dec. 28, 2018, which claims priority to U.S. Provisional Patent Application No. 62/611,176, filed Dec. 28, 2017, and U.S. Provisional Patent Application No. 62/724,937, filed Aug. 30, 2018. The entire contents of these applications are incorporated herein by reference in their entireties.

BACKGROUND OF THE INVENTION

The isolation and long-term expansion of primary cells, particularly stem/progenitor populations, are fundamental and important basic techniques in various biological fields, including developmental biology and stem cell biology, and medical science. Cells in epithelial tissues are highly regenerative and disproportionately accountable for many human cancers and inflammatory/autoimmune diseases. There are three principal shapes of epithelial cell: squamous, columnar, and cuboidal. These can be arranged in a single layer of cells as simple epithelium, either squamous, columnar, cuboidal, pseudo-stratified columnar or in layers of two or more cells deep as stratified (layered), either squamous, columnar or cuboidal. All glands are made up of epithelial cells. Functions of epithelial cells include secretion, selective absorption, protection, transcellular transport, and sensing. To illustrate, the intestinal epithelium is the layer of cells that forms the luminal surface or lining of both the small and large intestine (colon) of the gastrointestinal tract. It is composed of simple columnar epithelium. It has two important functions: absorbing helpful substances and providing a barrier against harmful substances. Some diseases and conditions are caused by dysfunction in the intestinal epithelium, and some diseases and conditions cause problems with these cells, which then leads to further complications.

Stem cells of the gastrointestinal tract, pancreas, liver and other columnar epithelia collectively resist cloning in their elemental states. The isolation and long-term expansion of primary cells, particularly stem/progenitor populations, are fundamental and important basic techniques in various biological fields, including developmental biology and stem cell biology, and medical science. Cells in stratified and columnar epithelial tissues are highly regenerative and disproportionately accountable for many human cancers; however, cloning adult stem cells is limited by difficulties in maintaining these cells in an immature state.

While dominating prospective strategies for regenerative medicine, embryonic stem cells (ESC) and induced pluripotent stem cells (iPSC) face formidable challenges including risk of teratoma, complex guiding protocols for lineage specificity, and limited regenerative capacity of the lineages ultimately produced. Müller et al. Development (1993) 118:1343-51; Helgason et al. Blood (1996) 87:2740-9; Bonde et al. Transplantation (2008) 86:1803-9; Iuchi et al. PNAS (2006) 103:1792-7; Amabile et al. Blood (2013) 121:1255-64; and Suzuki et al. Mol Ther (2013) 21:1424-31. The success and promise of iPSCs have largely overshadowed efforts to harness stem cells intrinsic to regenerative tissues. Green and colleagues developed methods for cloning epidermal stem cells that form a stratified epithelium upon engraftment, and these methods have been successfully applied to corneal, thymic, and airway epithelia. Rama et al. NEJM (2010) 363:147-155; Senoo et al. Cell (2007) 129:523-536; and Kumar et al. Cell (2011) 147:525-538. However, stem cells of columnar epithelial tissues resist cloning in a manner that maintains their immaturity during proliferative expansion, and instead must be carried forward as regenerative, differentiating "organoids". Matsuura et al. Stem Cells (2006) 24:624-630; Sato et al. Nature (2009) 459:262-5; Ootani et al. Nat Med (2009) 15:701-706; Sato et al. Nature (2011) 469:415-418; Fordham et al. Cell Stem Cell (2013) 13:734-744; and Middendorp et al. Stem Cells (2014) 32:1083-1091. Despite their obvious potential in regenerative medicine and constant improvement (Yin et al. Nat Methods (2014) 11:106-112), the very low percentage of clonogenic cells in organoids limits the kinetics of their propagation as well as their utility for exploring the elemental stem cell.

The limited ability to isolate stem cells from diseased epithelial tissues (i.e., cancer or inflammatory diseases such as IBD, asthma, COPD and the like) is equally a problem. The majority of human cancers are derived from epithelial tissues. Since the concept of cancer stem cells ("CSC") was introduced in late 1990s, it has gained acceptance as the mechanism underlying tumor initiation, propagation and ultimately drug resistance; these stem cells have influenced all approaches to cancer research and therapy as they help to mechanistically explain the progression of more benign to more aggressive forms of cancers. The majority of cancer drugs, while killing the bulk of tumor cells, ultimately fail to induce durable clinical responses because they are not able to eliminate the critical CSCs which are often resistant to existing cancer therapies including targeted drugs, chemo- and radiation therapy. Surviving CSCs give rise to new tumors and metastases, causing relapse of the disease. The recurrent tumors become more malignant, fast spreading and resistant to radiotherapy and previously used drugs, making the prognosis for cancer patients dismal.

Compounding matters is that many tumors are believed to contain a heterogeneous population of CSCs, representing a range of tumor promoting activities and a range of drug sensitivity. Thus, the specific survival of CSCs, or subsets of CSCs from the heterogeneous CSC population, could provide an explanation for many therapeutic failures and highlight new directions for the enhancement of cancer therapy. In order to develop truly effective treatments that can create a durable clinical response it is important to develop drugs that can target and kill CSCs. CSCs have only recently begun to be precisely identified due to technical advancements that facilitate identification, isolation, and interrogation of distinct tumor cell subpopulations with differing abilities to form and perpetuate tumors. There is therefore a need for methods and reagents for the isolation and stable passaging and expansion of columnar epithelial CSCs—so as to be useful in drug screening.

It is an object of the present invention to provide systems and reagents for the rapid isolation/cloning of columnar epithelial stem cells, particularly from small biopsies, under conditions which preserve the epigenetic memory and faithfully preserves the in vivo characteristics of the stem cells as they existed in the tissue biopsy through rounds of expansion and passaging in culture, so as to be scalable, efficient and ultimately affordable enough to be done on a patient-by-patient process for patient-specific diagnostic and treatment strategy purposes (inflammatory diseases and metaplasia/tumors as examples) or regenerative medicine purposes.

SUMMARY OF THE INVENTION

In one aspect, the invention provides a method for isolating a stem cell from epithelial tissue, preferably columnar epithelial tissue, e.g., normal or diseased tissue, the method comprising:
(1) culturing dissociated epithelial cells from a columnar epithelial tissue sample to form stem cell colonies, wherein the dissociated cells and cell colonies are cultured in a medium comprising:
(a) a ROCK (Rho Kinase) inhibitor; (b) a Wnt agonist; (c) a mitogenic growth factor; (d) insulin (or an insulin mimetic) or IGF; (e) a BRAF inhibitor; and (f) a EGF inhibitor;
wherein the medium optionally further comprises nicotinamide;
wherein the medium optionally further comprises a Notch Agonist;
wherein the medium optionally further comprises an Oct4-activating agent;
wherein the medium optionally further comprises a PDGFRα/β inhibitor, preferably a selective PDGFRα/β inhibitor;
wherein the medium optionally further comprises an JNK Inhibitor; wherein the medium optionally further comprises a TGFβ signaling pathway inhibitor (e.g., a TGFβ inhibitor or a TGFβ receptor inhibitor);
wherein the medium optionally further comprising a Bone Morphogenetic Protein (BMP) antagonist;
wherein the cells from the tissue sample are optionally in fluid or direct contact with mitotically inactive feeder cells, or are cultured in the absence of feeder cells;
wherein the cells from the tissue sample are optionally in contact with extracellular matrix (such as a basement membrane matrix) or other bio- or synthetic matrix;
(2) isolating single stem cells from the cell colonies, and
(3) culturing isolated single stem cells from step (2) individually to form cultures purified stem cell clones, (optionally) in contact with feeder cells and/or a basement membrane matrix in the medium; wherein each of the stem cell clones represents a clonal expansion of an epithelial stem cell present in the columnar epithelial tissue sample, thereby isolating columnar epithelial stem cells.

In certain preferred embodiments, the media comprises (a) a ROCK (Rho Kinase) inhibitor; (b) a Wnt agonist; (c) a mitogenic growth factor; (d) insulin or IGF; (e) a BRAF inhibitor; (f) a VEGF inhibitor; (g) nicotinamide; and (h) a Notch Agonist.

In certain preferred embodiments, the media comprises (a) a ROCK (Rho Kinase) inhibitor; (b) a Wnt agonist; (c) a mitogenic growth factor; (d) insulin or IGF; (e) a BRAF inhibitor; (f) a VEGF inhibitor; (g) nicotinamide; and (h) a Notch Agonist, and wherein the cells from the tissue sample are in fluid or direct contact with mitotically inactive feeder cells.

In certain preferred embodiments, the media comprises (a) a ROCK (Rho Kinase) inhibitor; (b) a Wnt agonist; (c) a mitogenic growth factor; (d) insulin or IGF; (e) a BRAF inhibitor; (f) a VEGF inhibitor; (g) nicotinamide; (h) a Notch Agonist; (i) a TGF signaling pathway inhibitor (e.g., a TGFβ inhibitor or a TGFβ receptor inhibitor); and (j) a Bone Morphogenetic Protein (BMP) antagonist.

In certain preferred embodiments, the media comprises (a) a ROCK (Rho Kinase) inhibitor; (b) a Wnt agonist; (c) a mitogenic growth factor; (d) insulin or IGF; (e) a BRAF inhibitor; (f) a VEGF inhibitor; (g) nicotinamide; (h) a Notch Agonist; (i) a TGF signaling pathway inhibitor (e.g., a TGFβ inhibitor or a TGFβ receptor inhibitor); and (j) a Bone Morphogenetic Protein (BMP) antagonist, and wherein the cells from the tissue sample are in fluid or direct contact with mitotically inactive feeder cells.

In certain preferred embodiments, the media comprises (a) a ROCK (Rho Kinase) inhibitor; (b) a Wnt agonist; (c) a mitogenic growth factor; (d) insulin or IGF; (e) a BRAF inhibitor; (f) a VEGF inhibitor; (g) nicotinamide; (h) a Notch Agonist; (i) a TGF signaling pathway inhibitor (e.g., a TGFβ inhibitor or a TGFβ receptor inhibitor); (j) a Bone Morphogenetic Protein (BMP) antagonist; (k) an Oct4-activating agent; (l) a PDGFRα/β inhibitor, preferably a selective PDGFRα/β inhibitor; and (m) a JNK Inhibitor.

In certain preferred embodiments, the media comprises (a) a ROCK (Rho Kinase) inhibitor; (b) a Wnt agonist; (c) a mitogenic growth factor; (d) insulin or IGF; (e) a BRAF inhibitor; (f) a VEGF inhibitor; (g) nicotinamide; (h) a Notch Agonist; (i) a TGF signaling pathway inhibitor (e.g., a TGFβ inhibitor or a TGFβ receptor inhibitor); (j) a Bone Morphogenetic Protein (BMP) antagonist; (k) an Oct4-activating agent; (l) a PDGFRα/β inhibitor, preferably a selective PDGFRα/β inhibitor; and (m) a JNK Inhibitor, and wherein the cells from the tissue sample are in fluid or direct contact with mitotically inactive feeder cells.

In certain preferred embodiments, the media comprises (a) a ROCK (Rho Kinase) inhibitor; (b) a Wnt agonist; (c) a mitogenic growth factor; (d) insulin or IGF; (e) a BRAF inhibitor; (f) a VEGF inhibitor; (g) nicotinamide; (h) a Notch Agonist; (i) a TGF signaling pathway inhibitor (e.g., a TGFβ inhibitor or a TGFβ receptor inhibitor); (j) a Bone Morphogenetic Protein (BMP) antagonist; (k) an Oct4-activating agent; (I) a PDGFRα/β inhibitor, preferably a selective PDGFRα/β inhibitor; and (m) a JNK Inhibitor, and wherein the culture system is free of feeder cells (i.e., only includes cells from the tissue sample and the progeny thereof).

The phrase "free of feeder cells" as used herein refers to a culture medium and/or a cell culture being devoid of feeder cells and/or a conditioned medium generated thereby.

In one aspect, the invention provides a feeder-free method for isolating a stem cell from epithelial tissue, preferably columnar epithelial tissue, e.g., normal or diseased tissue, the method comprising:
(1) culturing dissociated epithelial cells from a columnar epithelial tissue sample to form stem cell colonies, wherein the dissociated cells and cell colonies are cultured in a medium comprising:
(a) a ROCK (Rho Kinase) inhibitor; (b) a Wnt agonist; (c) a mitogenic growth factor; (d) insulin or IGF; (e) a BRAF inhibitor; and (f) a VEGF inhibitor;
wherein the medium optionally further comprises nicotinamide;
wherein the medium optionally further comprises a Notch Agonist;
wherein the medium optionally further comprises an Oct4-activating agent;
wherein the medium optionally further comprises a PDGFRα/β inhibitor, preferably a selective PDGFRα/β inhibitor;
wherein the medium optionally further comprises an JNK Inhibitor;

wherein the medium optionally further comprises a TGFβ signaling pathway inhibitor (e.g., a TGFβ inhibitor or a TGFβ receptor inhibitor);

wherein the medium optionally further comprising a Bone Morphogenetic Protein (BMP) antagonist;

wherein the culture system is free of feeder cells (i.e., only includes cells from the tissue sample and the progeny thereof);

wherein the cells from the tissue sample are optionally in contact with extracellular matrix (such as a basement membrane matrix) or other bio- or synthetic matrix;

(2) isolating single stem cells from the cell colonies, and (3) culturing isolated single stem cells from step (2) individually to form cultures purified stem cell clones, (optionally) in contact with feeder cells and/or a basement membrane matrix in the medium; wherein each of the stem cell clones represents a clonal expansion of an epithelial stem cell present in the columnar epithelial tissue sample, thereby isolating columnar epithelial stem cells.

In certain embodiments, the Notched agonist is Jagged-1 and is provided in the culture media at a concentration from 0.1 micromolar to 50 micromolar, preferably 0.1 micromolar to 10 micromolar, and more preferably 0.5 micromolar to 5 micromolar. In other embodiments, the Notched agonist is other than Jagged-1, and is provided in the culture media at an EC50 equivalent concentration from 0.1 micromolar to 50 micromolar Jagged-1, preferably 0.1 micromolar to 10 micromolar Jagged-1, and more preferably 0.5 micromolar to 5 micromolar Jagged-1.

In certain embodiments, the ROCK inhibitor is Y-27632 and is provided in the culture media at a concentration from 0.25 micromolar to 125 micromolar, preferably 0.25 micromolar to 25 micromolar, and more preferably 1.25 micromolar to 10 micromolar. In other embodiments, the ROCK inhibitor is other than Y-27632, and is provided in the culture media at an EC50 equivalent concentration from 0.25 micromolar to 125 micromolar Y-27632, preferably 0.25 micromolar to 25 micromolar Y-27632, and more preferably 1.25 micromolar to 10 micromolar Y-27632.

In certain embodiments, the ROCK inhibitor is GSK429286A and is provided in the culture media at a concentration from 25 nanomolar to 12.5 micromolar, preferably 25 nanomolar to 2.5 micromolar, and more preferably 125 nanomolar to 1.25 micromolar. In other embodiments, the ROCK inhibitor is other than GSK429286A, and is provided in the culture media at an EC50 equivalent concentration from 25 nanomolar to 12.5 micromolar GSK429286A, preferably 25 nanomolar to 2.5 micromolar GSK429286A, and more preferably 125 nanomolar to 1.25 micromolar GSK429286A.

In certain embodiments, the ROCK inhibitor is a combination of Y-27632 and GSK429286A, at concentrations as set out above, or an EC50 equivalent concentration of one or more other ROCK inhibitors.

In certain embodiments, the BMP antagonist is Noggin and is provided in the culture media at a concentration from 10 ng/mL to 5 micrograms/mL, preferably 10 ng/mL to 1 microgram/mL, and more preferably 50 ng/mL to 500 ng/mL. In other embodiments, the BMP antagonist is other than Noggin, and is provided in the culture media at an EC50 equivalent concentration from 10 ng/mL to 5 micrograms/mL Noggin, preferably 10 ng/mL to 1 microgram/mL Noggin, and more preferably 50 ng/mL to 500 ng/mL Noggin.

In certain embodiments, the WNT agonist is R-spondin-1 and is provided in the culture media at a concentration from 12.5 ng/mL to 6.25 micrograms/mL, preferably 12.5 ng/mL to 1.25 microgram/mL, and more preferably 62.5 ng/mL to 625 ng/mL. In other embodiments, the WNT agonist is other than R-spondin-1, and is provided in the culture media at an EC50 equivalent concentration from 12.5 ng/mL to 6.25 micrograms/mL R-spondin-1, preferably 12.5 ng/mL to 1.25 microgram/mL R-spondin-1, and more preferably 62.5 ng/mL to 625 ng/mL R-spondin-1.

In certain embodiments, the mitogenic growth factor is EGF and is provided in the culture media at a concentration from 1 ng/mL to 500 nanograms/mL, preferably 1 ng/mL to 100 nanogram/mL, and more preferably 5 ng/mL to 50 ng/mL. In other embodiments, the mitogenic growth factor is other than EGF, and is provided in the culture media at an EC50 equivalent concentration from 1 ng/mL to 500 nanograms/mL EGF, preferably 1 ng/mL to 100 nanogram/mL EGF, and more preferably 5 ng/mL to 50 ng/mL EGF.

In certain embodiments, the TGFβ signaling pathway inhibitor is SB431542 and is provided in the culture media at a concentration from 0.2 micromolar to 100 micromolar, preferably 0.2 micromolar to 20 micromolar, and more preferably 1.0 micromolar to 10 micromolar. In other embodiments, the TGFβ signaling pathway inhibitor is other than SB431542, and is provided in the culture media at an EC50 equivalent concentration from 0.2 micromolar to 100 micromolar SB431542, preferably 0.2 micromolar to 20 micromolar SB431542, and more preferably 1.0 micromolar to 10 micromolar SB431542.

In certain embodiments, the culture includes insulin at a concentration from 0.5 micrograms/mL to 250 micrograms/mL, preferably 0.5 micrograms/mL to 50 micrograms/mL, and more preferably 2.5 micrograms/mL to 25 micrograms/mL. In other embodiments, instead of insulin the culture media includes IGF or an insulin mimetic at an EC50 equivalent concentration from from 0.5 micrograms/mL to 250 micrograms/mL insulin, preferably 0.5 micrograms/mL to 50 micrograms/mL insulin, and more preferably 2.5 micrograms/mL to 25 micrograms/mL insulin.

In certain embodiments, the VEGF inhibitor is Tivozanib and is provided in the culture media at a concentration from 50 nanomolar to 25 micromolar, preferably 50 nanomolar to 5 micromolar, and more preferably 250 nanomolar to 2500 micromolar. In other embodiments, the VEGF inhibitor is other than Tivozanib, and is provided in the culture media at an EC50 equivalent concentration from 50 nanomolar to 25 micromolar Tivozanib, preferably 50 nanomolar to 5 micromolar Tivozanib, and more preferably 250 nanomolar to 2500 micromolar Tivozanib.

In certain embodiments, the B-raf inhibitor is GDC-0879 and is provided in the culture media at a concentration from 50 nanomolar to 25 micromolar, preferably 50 nanomolar to 5 micromolar, and more preferably 250 nanomolar to 2500 micromolar. In other embodiments, the B-raf inhibitor is other than GDC-0879 and is provided in the culture media at an EC50 equivalent concentration from 50 nanomolar to 25 micromolar GDC-0879, preferably 50 nanomolar to 5 micromolar GDC-0879, and more preferably 250 nanomolar to 2500 micromolar GDC-0879.

In certain embodiments, nicotinamide is provided in the culture media at a concentration from 1 nanomolar to 500 nanomolar, preferably 1 nanomolar to 100 nanomolar, and more preferably 5 nanomolar to 50 nanomolar.

In certain embodiments, the PDGFRα/β inhibitor is CP673451 and is provided in the culture media at a concentration from 0.1 micromolar to 50 micromolar, preferably 0.1 micromolar to 10 micromolar, and more preferably 0.5 micromolar to 5 micromolar. In other embodiments, the PDGFRα/β inhibitor is other than CP673451, and is provided in the culture media at an EC50 equivalent concentration from 0.1 micromolar to 50 micromolar CP673451, preferably 0.1 micromolar to 10 micromolar CP673451, and more preferably 0.5 micromolar to 5 micromolar CP673451.

In certain embodiments, the OCT4 activating agent is OAC1 and is provided in the culture media at a concentration from 0.1 micromolar to 50 micromolar, preferably 0.1 micromolar to 10 micromolar, and more preferably 0.5 micromolar to 5 micromolar. In other embodiments, the OCT4 activating agent is other than OAC1, and is provided in the culture media at an EC50 equivalent concentration from 0.1 micromolar to 50 micromolar OAC1, preferably 0.1 micromolar to 10 micromolar OAC1, and more preferably 0.5 micromolar to 5 micromolar OAC1.

In certain embodiments, the JNK inhibitor is JNK-IN-8 and is provided in the culture media at a concentration from 0.1 micromolar to 50 micromolar, preferably 0.1 micromolar to 10 micromolar, and more preferably 0.5 micromolar to 5 micromolar. In other embodiments, JNK inhibitor is other than JNK-IN-8, and is provided in the culture media at an EC50 equivalent concentration from 0.1 micromolar to 50 micromolar JNK-IN-8, preferably 0.1 micromolar to 10 micromolar JNK-IN-8, and more preferably 0.5 micromolar to 5 micromolar JNK-IN-8.

As used herein "EC50 equivalent concentration" means a concentration of an agent relative to the reference agent, which after adjusting for the differences between the two agents in EC50 on the cultured cells, gives the same biological effect on the cultured cells. So, for example, a ROCK inhibitor that has an EC50 on the cultured cells that is 5 times higher (i.e., less effective) than Y-27632 may require a concentration of 6.25 micromolar to 50 micromolar to give the same range of biological effect on the cell culture as 1.25 micromolar to 10 micromolar of Y-27632. In the case of those agents which are inhibitors of a particular receptor, enzyme, pathway, etc, the IC50 can be used in place of EC50.

In certain embodiments, the epithelial tissue from the patient having the disease, disorder, or abnormal condition is afflicted by the disease, disorder, or abnormal condition. In certain embodiments, the columnar epithelial stem cell is an adult columnar epithelial stem cell. In certain embodiments, the columnar epithelial stem cell is a fetal columnar epithelial stem cell.

In certain embodiments, the medium does not include a Notch agonist.

In certain embodiments, in step (1), the (epithelial) cells are dissociated from the tissue through enzymatic digestion with an enzyme. For example, the enzyme may comprise collagenase, protease, dispase, pronase, elastase, hyaluronidase, accutase or trypsin.

In certain embodiments, in step (1), the (epithelial) cells are dissociated from the tissue through dissolving extracellular matrix surrounding the (epithelial) cells.

In certain embodiments, the mitotically inactivated cells are mitotically-inactivated fibroblasts, preferably human or murine fibroblasts, such as 3T3-J2 cells. Mitotic inactivation can be accomplished by the administration of mitomycin C or other chemically-based mitotic inhibitors, irradiation with γ-rays, irradiation with X-rays, and/or irradiation with UV light.

In certain embodiments, the extracellular matrix is a basement membrane matrix, such as a laminin-containing basement membrane matrix (e.g., MATRIGEL™ basement membrane matrix (BD Biosciences)), and is preferably growth factor-reduced. In other embodiments, the biopolymer is selected from the group consisting of collagen, chitosan; fibronectin, fibrin, and mixtures thereof.

In certain embodiments, the basement membrane matrix does not support 3-dimensional growth, or does not form a 3-dimensional matrix necessary to support 3-dimensional growth.

In certain embodiments, the medium further comprises serum, preferably FBS (and even more preferably FBS that is not heat inactivated), such as in a concentration of 5%-15%, such as 10% FBS.

In certain embodiments, the ROCK inhibitor comprises Rho Kinase Inhibitor VI (Y-27632, (R)-(+)-trans-N-(4-Pyridyl)-4-(1-aminoethyl)-cyclohexanecarboxamide)), Fasudil or HA1077 (5-(1,4-diazepan-1-ylsulfonyl)isoquinoline), or HI 152 ((S)-(+)-2-methyl-1-[(4-methyl-5-isoquinolinyl)sulfonyl]-hexahydro-1H-1,4-diazepine dihydrochloride).

In certain embodiments, the BMP antagonist comprises Noggin, DAN, a DAN-like proteins comprising a DAN cystine-knot domain (e.g., Cerberus and Gremlin), Chordin, a chordin-like protein comprising a chordin domain, Follistatin, a follistatin-related protein comprising a follistatin domain, sclerostin/SOST, decorin, or a-2 macro globulin. In certain preferred embodiments, the BMP antagonist is Noggin.

In certain embodiments, the Wnt agonist comprises R-spondin 1, R-spondin 2, R-spondin 3, R-spondin 4, an R-spondin mimic, a Wnt family protein (e.g., Wnt-3a, Wnt 5, Wnt-6a), Norrin, or a GSK-inhibitor (e.g., CHIR99021).

In certain embodiments, the mitogenic growth factor comprises EGF, Keratinocyte Growth Factor (KGF), TGFa, BDNF, HGF, and/or FGF (e.g., FGF7 or FGF10).

In certain embodiments, the TGF-beta receptor inhibitor comprises SB431542 (4-(4-(5-benzo[1,3]dioxol-5-yl)-4-(pyridin-2-yl)-1H-imidazol-2-yl)benzamide), A83-01, SB-505124, SB-525334, LY 364947, SD-208, or SJN 2511.

In certain embodiments, the TGF-beta (signaling) inhibitor binds to and reduces the activity of one or more serine/threonine protein kinases selected from the group consisting of ALK5, ALK4, TGF-beta receptor kinase 1 and ALK7.

In certain embodiments, the TGF-beta (signaling) inhibitor is added at a concentration of between 1 nM and 100 µM, between 10 nM and 100 µM, between 100 nM and 10 µM, or approximately 1 µM.

In certain embodiments, the BRAF inhibitor is selected from the group consisting of AMG542, ARQ197, ARQ736, AZ628, CEP-32496, GDC-0879, GSK1120212, GSK2118436 (dabrafenib, Tafinlar), LGX818 (encorafenib), NMS-P186, NMS-P349, NMS-P383, NMS-P396, NMS-P730, PLX3603 (RO5212054), PLX4032 (vemurafenib, Zelboraf), PLX4720 (Difluorophenyl-sulfonamine), PF-04880594, PLX4734, RAF265 (CHIR-265), RO4987655, SB590885, sorafenib, sorafenib tosylate, and XL281 (BMS-908662). Exemplary BRAF inhibitors are also available from Selleckchem (world-wide web at selleckchem.com/BRAF.html) and include Vemurafenib (PLX4032, RG7204); Sorafenib Tosylate; PLX-4720; Dabrafenib (GSK2118436); GDC-0879; Lifirafenib (BGB-283); CCT196969; RAF265 (CHIR-265); AZ 628; NVP-BHG712; SB590885; ZM 336372; Sorafenib; GW5074; TAK-632; Raf265 derivative; CEP-32496; Encorafenib (LGX818); PLX7904; LY3009120; RO5126766 (CH5126766) and MLN2480.

In certain embodiments, the VEGF inhibitor is selected from aflibercept, pegaptanib, tivozanib, 3-(4-Bromo-2,6-difluoro-benzyloxy)-5-[3-(4-pyrrolidin-1-yl-butyl)-ureido]-isothiazole-4-carboxylic acid amide hydrochloride, axitinib, N-(4-bromo-2-fluorophenyl)-6-methoxy-7-[(1-methylpiperidin-4-yl-)methoxy]quinazolin-4-amine, an inhibitor of VEGF-R2 and VEGF-R1, axitinib, N,2-dimethyl-6-(2-(1-methyl-1H-imidazol-2-yl)thieno[3,2-b]pyrid-in-7-yloxy) benzo[b]thiophene-3-carboxamide, tyrosine kinase inhibitor of the RET/PTC oncogenic kinase, N-(4-bromo-2-fluorophenyl)-6-methoxy-7-[(1-methylpiperidin-4-yl) methoxy] quinazol in-4-amine, pan-VEGF-R-kinase inhibitor; protein kinase inhibitor, multitargeted human epidermal receptor (HER) 1/2 and vascular endothelial growth factor receptor (VEGFR) 1/2 receptor family tyrosine kinases inhibitor, cediranib, sorafenib, vatalanib, glufanide disodium, VEGFR2-selective monoclonal antibody, angiozyme, an siRNA-based VEGFR1 inhibitor, 5-((7-Benzyloxyquinazolin-4-yl)amino)-4-fluoro-2-methyl phenol hydrochloride, any derivatives thereof and any combinations thereof.

In certain preferred embodiments, the VEGF inhibitor is a VEGF Receptor inhibitor, and even more preferably a VEGF Receptor kinase inhibitor such as Tivozanib (AV-951), AZD2932, Midostaurin (pkc412), BAW2881 (NVP-BAW2881), Nintedanib (BIBF 1120), SU5402, SU1498, BFH772, Sorafenib, Sunitinib, Dovitinib (TK1258), Semaxanib (SU5416), hypericin, vatalanib, ZM306416, AAL993, SU4312, DMXAA or Foretinib.

In certain embodiments, the BRAF inhibitor and the VEGF Receptor kinase inhibitor are the same compound, such as Sorafenib which is a dual inhibitor of VEGFR kinases and RAF kinases.

An exemplary selective inhibitor of PDGFRα/β is CP-673451

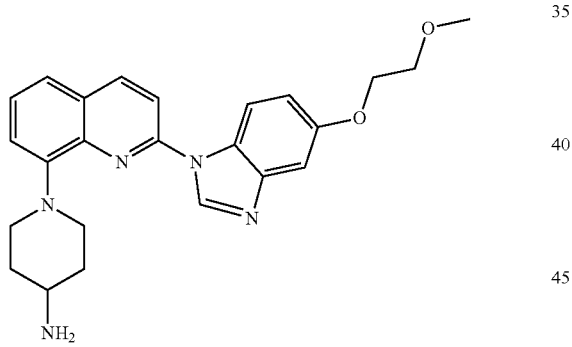

Exemplary JNK inhibitors include, but are not limited to, SP600125 (anthra[1-9-cd]pyrazol-6(2H)-one), JNK-IN-8 (3-[[4-(dimethylamino)-1-oxo-2-buten-1-yl]amino]-N-[3-methyl-4-[[4-(3-pyridinyl)-2-pyrimidinyl]amino]phenyl]-benzamide); and JNK-Inhibitor IX (N-(3-cyano-4,5,6,7-tetrahydrobenzo[b]thien-2-yl)-1-naphthalenecarboxamide).

In certain embodiments, the Oct4-activating agent is selected from the group consisting of

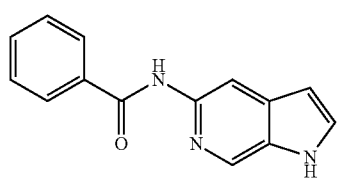

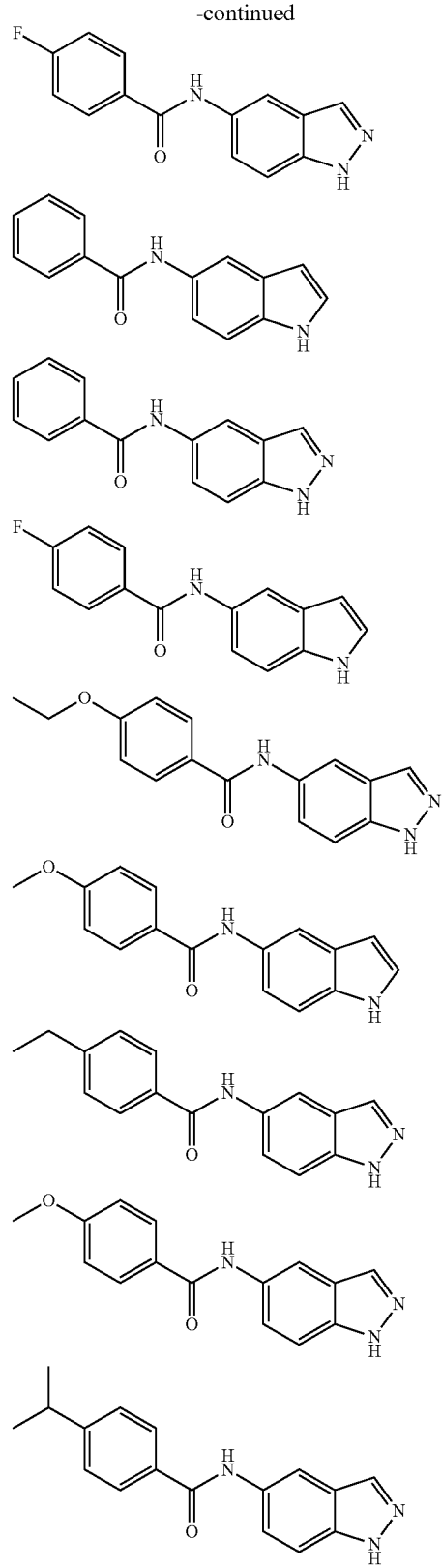

In another aspect, the invention provides a single cell clone of an epithelial stem cell, or an in vitro culture thereof, such as one comprising a subject medium, wherein the epithelial stem cell substantially lacks expression of marker(s) associated with differentiated cell types in the epithelial tissue from which it was derived.

In another aspect, the invention provides a single cell clone of a non-embryonic epithelial stem cell, or an in vitro culture thereof, such as one comprising a subject medium, wherein the non-embryonic epithelial stem cell has an immature, undifferentiated morphology characterized by small round cell shape with high nucleus to cytoplasm ratio.

In a related aspect, the invention also provides a library or collection of the subject single cell clone, or in vitro culture (such as one comprising a subject medium) thereof. In certain embodiments, the library or collection may comprise single cell clones from the same tissue/organ type. In certain embodiments, the library or collection may comprise single cell clones isolated from the same type of tissue/organ type, but from different members of a population. In certain embodiments, one or more (preferably each) member of the population are homozygous across at least one tissue typing locus (such as HLA-A, HLA-B, and HLA-D). In certain embodiments, at least one tissue typing locus (e.g., the HLA loci above) is engineered in the cloned stem cells via, for example, TALEN or CRISPR technologies (see below) to generate universal donor cell lines (e.g. liver cells) lacking tissue antigens encode by the tissue typing locus (e.g., HLA-A, HLA-B, and HLA-D, etc.). See Torikai et al. (Blood, 122(8): 1341-1349, 2013, incorporated by reference). In certain embodiments, the population may be defined by ethnic group, age, gender, disease status, or any common characteristics of a population. The library or collection may have at least about 20, 30, 40, 50, 60, 70, 80, 90, 100, 120, 150, 180, 200, 250, 300 or more members.

In another aspect, the invention provides a method of treating a subject having a disease, a disorder, or an abnormal condition and in need of treatment, comprising: (1) using any of the subject method, isolating an epithelial stem cell from a tissue corresponding to a tissue affected by the disease, disorder, or abnormal condition in the subject; (2) optionally, altering the expression of at least one gene in the epithelial stem cell to produce an altered epithelial stem cell; (3) reintroducing the isolated epithelial stem cell or altered epithelial stem cell, or a clonal expansion thereof, into the subject, wherein at least one adverse effect or symptom of the disease, disorder, or abnormal condition is alleviated in the subject.

In certain embodiments, the expression of at least one gene in the epithelial stem cell is genetically, recombinantly and/or epigenetically altered to produce an altered epithelial stem cell.

In certain embodiments, the tissue from which the epithelial stem cell is isolated is from a healthy adult or fetal (i.e., non-embryonic) subject.

In certain embodiments, the tissue from which the epithelial stem cell is isolated is from the subject. In certain embodiments, the tissue from which the epithelial stem cell is isolated is an affected tissue affected by the disease, disorder, or abnormal condition.

In certain embodiments, the tissue from which the epithelial stem cell is isolated is adjacent to an affected tissue affected by the disease, disorder, or abnormal condition.

In certain embodiments, the at least one gene is underexpressed in the tissue affected by the disease, disorder, or abnormal condition in the subject, and expression of the at least one gene is enhanced in the altered epithelial stem cell.

In certain embodiments, the at least one gene is overexpressed in the tissue affected by the disease, disorder, or abnormal condition in the subject, and expression of the at least one gene is reduced in the altered epithelial stem cell.

In certain embodiments, step (2) is affected by introducing into the epithelial stem cell an exogenous DNA or RNA.

In yet another aspect, the invention provides a method of screening for a compound, the method comprising: (1) using any of the methods of the invention, isolating an epithelial stem cell from a subject; (2) producing a cell line of the epithelial stem cell via single cell clonal expansion; (3) contacting test cells from the cell line with a plurality of candidate compounds; and, (4) identifying one or more compounds that produces a pre-determined phenotype change in the test cells.

Another aspect of the invention provides the use of epithelial stem cells, or the progeny thereof, isolated from a diseased epithelial tissue utilizing a culture medium system of the present invention, for the identification of a drug agent that selectively inhibits the growth or proliferation of the stem cell or its progeny relative to normal regenerative epithelial stem cells, or reverts the epithelial stem cell to a normal epigenetic state so that it differentiates to normal epithelial tissue. The diseased epithelial tissue can be, for example, from a patient with an inflammatory disease or a tumor. In certain embodiments, the method further provides that the identified drug agent is formulated for administration to a mammalian subject, such as a human patient, such as by formulation with pharmaceutical acceptable excipients.

Another aspect of the invention provides the use of epithelial stem cells, or the progeny thereof, isolated from normal epithelial tissue utilizing the culture medium system of the present invention, for the identification of a drug agent that promotes the growth, proliferation and/or regenerative capacity of the stem cells. In certain embodiments, the method further provides that the identified drug agent is formulated for administration to a mammalian subject, such as a human patient, such as by formulation with pharmaceutical acceptable excipients.

It is contemplated that any embodiments described herein, including embodiments described in the examples and figures/drawings, and embodiments described under different aspects of the invention, can be combined with any one or more other embodiments where applicable.

BRIEF DESCRIPTION OF THE DRAWINGS

FIG. 3B: Single-cell derived human colonic stem cell pedigree differentiate in to all cell types in intestine. This figure illustrates that following cell polarity formation, a single-stem-cell derived pedigree differentiate into goblet cells (MUC2 positive), endocrine cells (CHGA positive), paneth cells (DEFA6 positive), and enterocyte (Villin positive).

FIG. 5C: Illustrates the polyclonality in intestinal epithelium by sampling ISCGS clones from aged patients (40-70) in a copy number variation study. This figure shows that several other clones of the same patient from FIGS. 5A and 5B displayed wild-type genome.

FIG. 7: Is a schema showing a process for screening cultured intestinal stem cells prior to transplantation for safety concerns.

DETAILED DESCRIPTION OF EXEMPLARY EMBODIMENTS

1. Overview

Figure 1:
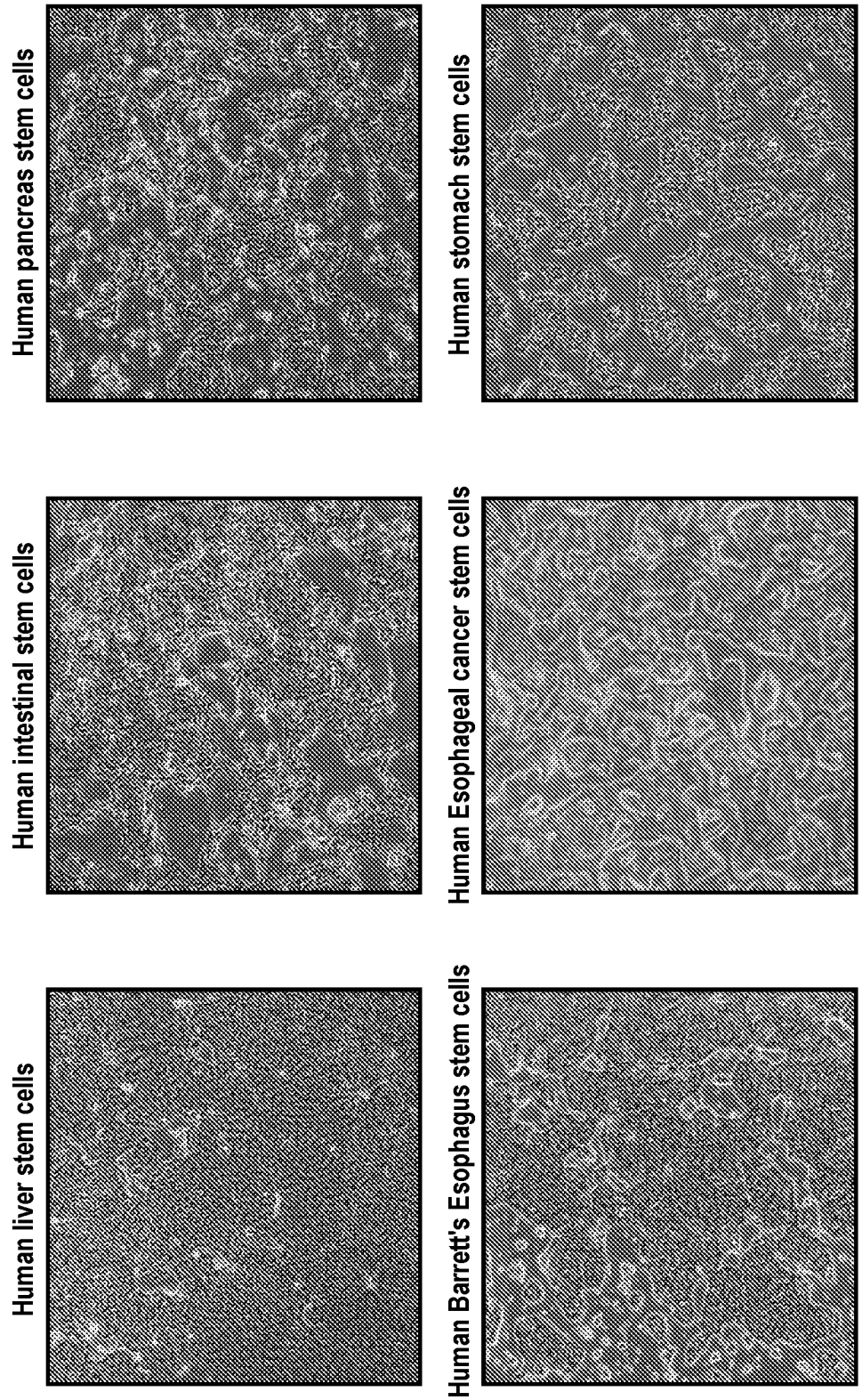
FIG. 1: Representative images of stem cells derived from various human columnar epithelium such as liver, intestine, pancreas, Stomach and diseased epithelium such as Barrett's Esophagus and Esophageal cancer.
Figure 2:
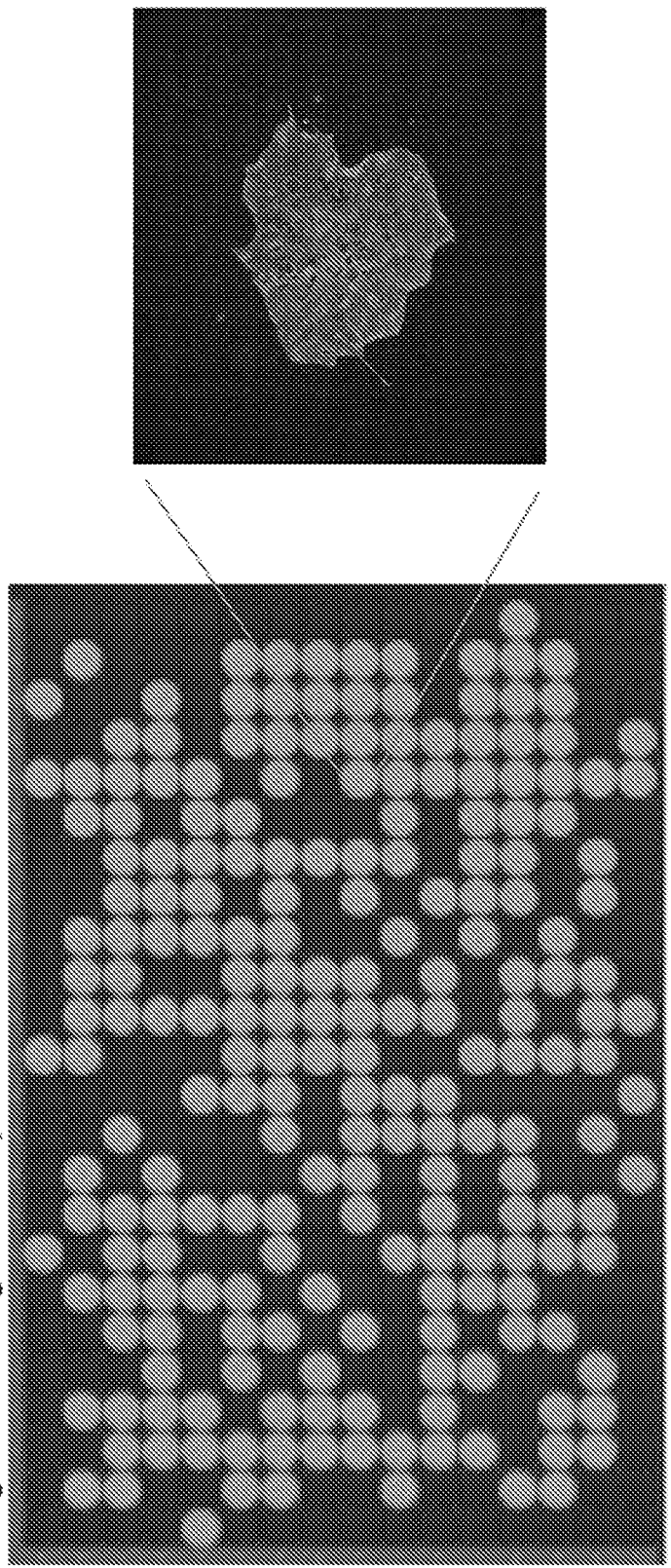
FIG. 2: Epithelial stem cells are highly clonogenic. Single cell was sorted into each well of tissue culture plate and approximately 70% of the single cells can give rise to a colony that can then be expanded to a pedigree.
Figure 3A:
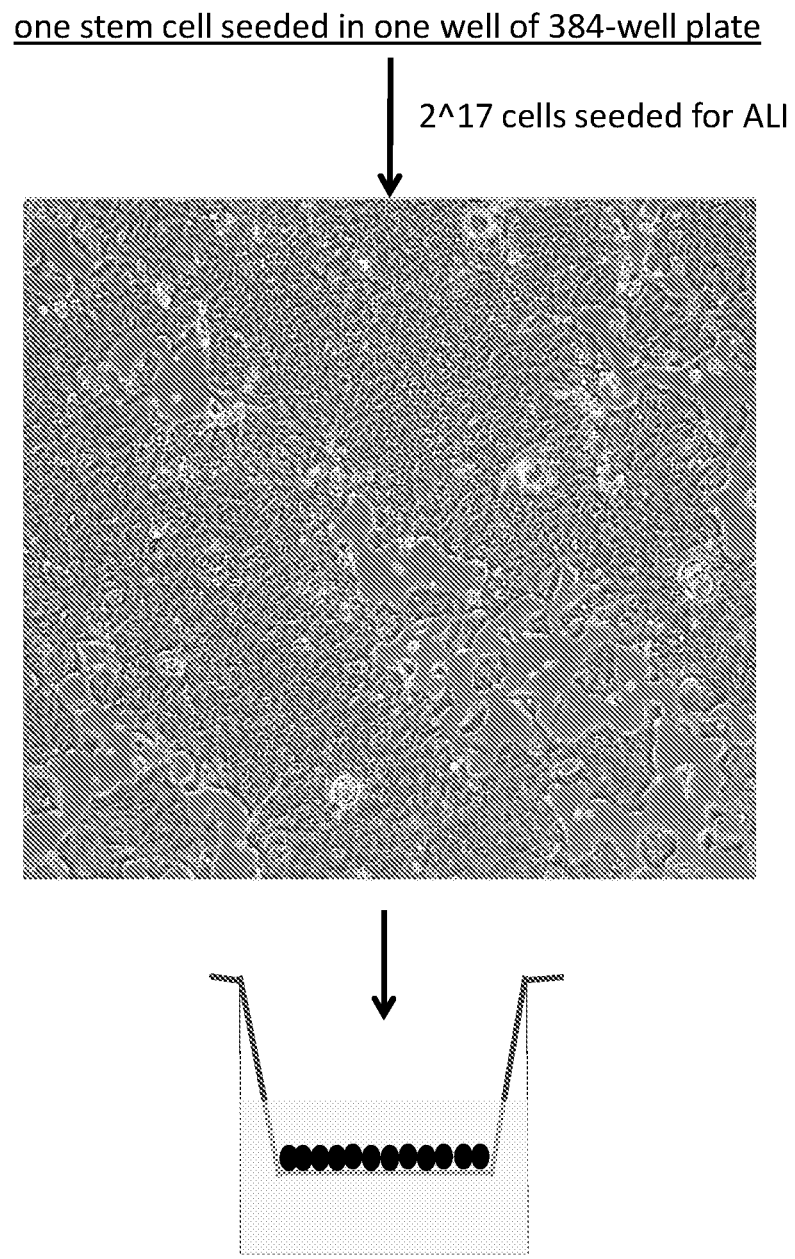
FIG. 3A: Single-cell derived human colonic stem cell pedigree differentiate in to all cell types in intestine. This figure shows the colonic stem cells cultured in MGM medium were seeded in transwell membrane and allowed to reach confluent. Then the air-liquid interface was created by removing the medium inside the well.

The invention described herein relates to methods of isolating and/or maintaining in culture non-embryonic (e.g., adult or fetal) epithelial stem cells from the columnar epithelia of organs. Epithelial stem cells thus isolated from the various tissues or organs can self-renew or propagate indefinitely in vitro, are multipotent and can differentiate into the various differentiated cell types normally found within the tissue or organ from which the stem cells are isolated. Cultures (including in vitro cultures) comprising the epithelial stem cells thus isolated are also within the scope of the invention.

In addition, the isolated epithelial stem cells can be propagated through clonal expansion of a single isolated stem cell, to produce a clone (e.g., as an in vitro culture) of which at least about 40%, 70%, or 90% or more cells within the clone can be further passaged as single cell originated clones. Thus, the stem cells isolated using the methods of the invention are uniquely capable of being manipulated in vitro through standard molecular biology techniques, such as introduction of exogenous genetic materials through infection or transfection.

As used herein, "epithelial stem cell" includes adult stem cell isolated from an adult tissue or organ, and fetal stem cell isolated from prenatal tissue or organ.

In a related embodiment, the methods of the invention described herein isolate fetal stem cells from a fetal or prenatal tissue or organ. In certain embodiments, when fetal tissue or organ is the source of the stem cell, the methods of the invention do not destroy the fetus or otherwise impair the normal development of the fetus, especially when the fetus is a human fetus. In other embodiments, the source of the fetal tissue is obtained from aborted fetus, dead fetus, macerated fetal material, or cell, tissue or organs excised therefrom.

The methods of the invention is applicable to any animal columnar epithelial tissue containing epithelial stem cells, including tissues from human, non-human mammal, non-human primate, rodent (including but not limited to mouse, rat, ferret, hamster, guinea pig, rabbit), livestock animals (including but not limited to pig, cattle, sheep, goat, horse, camel), bird, reptile, fish, pet or other companion animals (e.g., cat, dog, bird) or other vertebrates, etc.

"Columnar epithelial cells" are elongated and column-shaped and have a height of at least four times their width. Their nuclei are elongated and are usually located near the base of the cells. Columnar epithelium forms the lining of the stomach and intestines. The cells here may possess microvilli for maximizing the surface area for absorption and these microvilli may form a brush border. Other cells may be ciliated to move mucus in the function of mucociliary clearance. Other ciliated cells are found in the fallopian tubes, the uterus and central canal of the spinal cord. Some columnar cells are specialized for sensory reception such as in the nose, ears and the taste buds. Hair cells in the inner ears have stereocilia which are similar to microvilli. Goblet cells are modified columnar cells and are found between the columnar epithelial cells of the duodenum. They secrete mucus, which acts as a lubricant. Single-layered non-ciliated columnar epithelium tends to indicate an absorptive function.

A simple columnar epithelium is a columnar epithelium that is uni-layered. In humans, a simple columnar epithelium lines most organs of the digestive tract including the stomach, small intestine, and large intestine. Simple columnar epithelia line the uterus. Simple columnar epithelium is further divided into two categories: ciliated and non-ciliated. Ciliated columnar epithelium moves mucus and other substances via cilia and is found in the upper respiratory tract, the Fallopian tubes, the uterus, and the central part of the spinal cord.

A ciliated columnar epithelium lines the lumen of the uterine tube, where currents generated by the cilia propel the egg cell toward the uterus.

Non-ciliated epithelium is found lining sections of the gastrointestinal tract and may be brush bordered.

"Pseudostratified columnar epithelium" is columnar epithelia which, though comprising only a single layer of cells, has its cell nuclei positioned in a manner suggestive of stratified epithelia. Pseudostratified columnar epithelium is found, for example, in lining the trachea, bronchi, male urethra, and a few other places.

In certain embodiments, the epithelial tissue is isolated from a healthy or normal individual.

In certain embodiments, the epithelial tissue is isolated from a disease tissue (e.g., a tissue affected by a disease), a disorder tissue (e.g., a tissue affected by a disorder), or a tissue otherwise have an abnormal condition.

As used herein, the term "disease" includes an abnormal or medical condition that affects the body of an organism, and is usually associated with specific symptoms and signs. The disease may be caused by external factors (such as infectious disease, including papilloma virus infection or a sexually transmitted disease), or by internal dysfunctions (such as autoimmune diseases or cancer). In a broad sense, "disease" may also include any condition that causes pain, dysfunction, distress, social problems, or death to the person afflicted, or similar problems for those in contact with the person. In this broader sense, it may include injuries, disabilities, disorders, syndromes, infections, isolated symptoms, deviant behaviors, and atypical variations of structure and function, while in other contexts and for other purposes these may be considered distinguishable categories. In certain preferred embodiments, the stem cells are isolated from a tumor biopsy.

In certain embodiments, the epithelial tissue is isolated from an individual having a disease, disorder, or otherwise abnormal condition, although the epithelial tissue itself may not have been inflicted with the disease, disorder, or abnormal condition. For example, the epithelial tissue may be isolated from a patient having inflammatory bowel disease or gastric cancer, but from a healthy portion of the bowel (in the case of IBD) or stomach (in the case of the tumor) not already inflicted with the inflammatory condition or cancer. In certain embodiments, the epithelial tissue may be nearby or distant from the disease, disorder, or abnormal tissue.

In certain embodiments, the epithelial tissue is isolated from an individual predisposed to develop a disease, disorder, or otherwise abnormal condition, or in high risk of developing the disease, disorder, or otherwise abnormal condition, based on, for example, genetic composition, family history, life style choice (e.g., smoking, diet, exercise habit), previous viral infection or the like of the individual, although the individual has not yet developed the disease, disorder, or otherwise abnormal condition, or displayed a detectable symptom of the disease, disorder, or otherwise abnormal condition.

Another aspect of the invention provides an epithelial stem cell isolated according to any one of the methods of the invention, or an in vitro culture thereof.

In yet another aspect, the invention further provides a single cell clone of an isolated epithelial stem cell, or an in vitro culture thereof, wherein at least about 40%, 50%, 60%, 70%, or about 80% of cells within the single cell clone, when isolated as single cell, is capable of proliferation to produce single cell clone.

Each single cell clone, depending on stages of growth and other growth conditions, may comprise at least about 10, 100, $10^3$, $10^4$, $10^5$, $10^6$ or more cells.

In a related aspect, the invention provides a single cell clone of an isolated epithelial stem cell, or an in vitro culture thereof, wherein the epithelial stem cell, when isolated as single cell, is capable of self-renewal for greater than about 50 generations, 70 generations, 100 generations, 150 generations, 200 generations, 250 generations, 300 generations, 350 generations, or about 400 or more generations.

In certain embodiments, the in vitro culture comprises a medium of the invention (e.g., a modified medium of the invention as described below). See section below describing the medium of the invention, each medium described therein is incorporated herein by reference. In certain embodiments, the epithelial stem cell is capable of differentiating into a differentiated cell type of the epithelial tissue from which it was originally biopsied, or in the case of a cancer stem cell, a tumor of that tissue origin. For example, the isolated epithelial stem cell of the invention may differentiate into one or more cell types normally found in epithelial tissue of the biopsy from which it was derived.

In certain embodiments, the epithelial stem cell is capable of differentiating into organized structures resembling the structure or substructures found in the tissue from which such epithelial stem cell originates. For example, an isolated liver stem cell of the invention may differentiate into liver-tissue-like structure that resembles liver epithelia, and an isolated gastrointestinal stem cell of the invention may differentiate into GI-tissue-like structure that resembles gastrointestinal epithelia.

In certain embodiments, the epithelial stem cell has an immature, undifferentiated morphology characterized by small round cell shape with high nucleus to cytoplasm ratio.

A further aspect of the invention provides a method of treating a subject having a disease, a disorder, or an abnormal condition and in need of treatment, comprising: (1) using any of the methods of the invention to isolate a non-embryonic (e.g., an adult) stem cell from a regenerative tissue corresponding to a tissue affected by the disease, disorder, or abnormal condition in the subject; (2) altering the expression of at least one gene in the epithelial stem cell to produce an altered epithelial stem cell; (3) reintroducing the altered epithelial stem cell or a clonal expansion or a culture derived tissue transplant thereof into the subject, wherein at least one adverse effect or symptom of the disease, disorder, or abnormal condition is alleviated in the subject, or as a means of regenerating/replacing damaged reproductive tissue. In other instances, the transplanted cells/tissue can be genetically engineered to be resistant to viral infection, such as papillomavirus infection.

For example, step (2) of the method may be effected by introducing into the epithelial stem cell an exogenous DNA or RNA that either increases or decreases the expression of a target gene in the isolated epithelial stem cell. Any of the art-recognized molecular biology techniques can be used to alter gene expression in a cell, e.g., in vitro or ex vivo. Such methods may include, without limitation, transfection or infection by a viral or non-viral based vector, which may encode the coding sequence of a protein or functional fragments thereof that is dysfunctional or deficient in the target cell, or may encode an RNA (antisense RNA, siRNA, miRNA, shRNA, ribozyme, etc.) that disrupts the function of a target gene.

In certain embodiments, the tissue from which the epithelial stem cell is isolated is from a healthy subject. Preferably, the healthy subject is HLA-type matched with the subject in need of treatment.

In certain embodiments, the tissue from which the epithelial stem cell is isolated is from the subject, and the isolated epithelial stem cell is autologous with respect to the subject.

In certain embodiments, the tissue from which the epithelial stem cell is isolated is an affected tissue affected by the disease, disorder, or abnormal condition.

In certain embodiments, the tissue from which the epithelial stem cell is isolated is adjacent to an affected tissue affected by the disease, disorder, or abnormal condition.

In certain embodiments, at least one gene is under-expressed in the tissue affected by the disease, disorder, or abnormal condition in the subject, and expression of the at least one gene is enhanced in the altered epithelial stem cell.

In certain embodiments, at least one gene is over-expressed in the tissue affected by the disease, disorder, or abnormal condition in the subject, and expression of the at least one gene is reduced in the altered epithelial stem cell.

In another aspect, the invention also provides a method of screening for agents or conditions that alter the "phenotype" of the cells—such as the differentiation, epigenetics, survival or the like of a reproductive tissue stem cells—whether normal or from a cancer/disease state. In an exemplary embodiment, the method comprises: (1) using any of the methods of the invention to isolate epithelial stem cells (including a cancer stem cell) from the reproductive tissue of a subject; (2) producing one or more stem cell lines from the epithelial stem cells via single cell clonal expansion; (3) contacting test cells from the cell line with one or more candidate compounds; and, (4) identifying compounds that produces a predetermined phenotype change in the test cells. This screening method of the invention may be used for target identification and validation. For example, a potential target gene in an epithelial stem cell isolated from a patient in need of treatment may functional abnormally (either over-expression or under-expression) to cause a phenotype associated with a disease, disorder, or abnormal condition. A clonal expansion of the epithelial stem cell isolated using the method of the invention may be subject to the screening method of the invention to test an array of potential compounds (small molecule compounds, etc.) to identify one or more compounds that can correct, alleviate, or reverse the phenotype.

In another embodiment, an epithelial stem cell may be isolated from regenerative tissue of a patient in need of treatment, such as from the reproductive tissue affected by a disease, disorder, or abnormal condition. A clonal expansion of the epithelial stem cell isolated using the method of the invention may be subject to the screening method of the invention to test an array of potential compounds (small molecule compounds, or any RNA-based antagonists such as library of siRNA, etc.) to identify one or more compounds that can correct, alleviate, or reverse the phenotype. The affected target gene by an effective compound may be further identified by, for example, microarray, RNA-Seq, or PCR based expression profile analysis.

The epithelial stem cell isolated using the methods of the invention and clonal expansion thereof may be further useful for toxicology screens or studies such that any toxicology analysis and test can be tailored to individual patients set to receive a certain medicine or medical intervention.

The epithelial stem cell isolated using the methods of the invention and clonal expansion thereof may also be useful for regenerative medicine, where either autologous stem cells or stem cells isolated from HLA-type matched healthy donor can be induced to differentiate into reproductive tissues or organs in vitro, ex vivo, or in vivo to treat an existing condition or prevent/delay such a condition from developing. Such stem cells may be genetically manipulated prior to induced differentiation.

The epithelial stem cell isolated using the methods of the invention and clonal expansion thereof may be used in an in vitro or in vivo disease model. For example, isolated intestinal stem cells may be induced to differentiate in an air-liquid interface (ALI) to produce intestinal epithelia-like structures, which may be used in any of the screening methods described herein. The isolated epithelial stem cells (e.g., those from human) may also be introduced into SCID or nude mice or rat to establish humanized disease model suitable for carrying out in vivo methods, such as the screening methods of the invention.

2. Methods for Obtaining and/or Culturing Stem Cells

One aspect of the invention relates to a method for isolating an epithelial stem cell from a epithelial tissue, as generally described above.

To illustrate, one step of the method comprises culturing dissociated epithelial cells from the epithelial tissue, (optionally) in contact with a first population of mitotically inactive feeder cells and/or an extracellular matrix, e.g., a basement membrane matrix, to form epithelial cell clones.

In certain embodiments, the (epithelial) cells are dissociated from the tissue through enzymatic digestion with an enzyme, including, without limitation, any one or more of collagenase, protease, dispase, pronase, elastase, hyaluronidase, Accutase and/or trypsin.

These enzymes or functional equivalents are well known in the art, and in almost all cases are commercially available.

In other embodiments, the (epithelial) cells may be dissociated from the tissue sample through dissolving extracellular matrix surrounding the (epithelial) cells. One reagent suitable for this embodiment of the invention include a non-enzymatic proprietary solution marketed by BD Biosciences (San Jose, Calif.) as the BD™ Cell Recovery Solution (BD Catalog No. 354253), which allows for the recovery of cells cultured on BD MATRIGEL™ Basement Membrane Matrix for subsequent biochemical analyses.

In certain embodiments the culture system includes feeder cells, which feeder cells may comprise, to illustrate, certain lethally irradiated fibroblast, such as the murine 3T3-J2 cells. Other feeder cells include human dermal fibroblasts, (human) adipose-derived mesenchymal stem cells, (human) bone marrow-derived mesenchymal stem cells, (human) amniotic epithelial cells, (mouse or human) embryonic feeder cells, (human) bone marrow stromal cells, HELA cells, and (human) amniocytes. The feeder cells may form a feeder cell layer on top of the basement membrane matrix.

In other embodiments, feeder cell conditioned media can be used to substitute in those embodiments where feeder cells might be used.

A suitable 3T3-J2 cell clone is well known in the art (see, for example, Todaro and Green, "Quantitative studies of the growth of mouse embryo cells in culture and their development into established lines.". Cell Biol. 17: 299-313, 1963), and is readily available to the public. For example, Waisman Biomanufacturing (Madison, Wis.) sells irradiated 3T3-J2 feeder cells produced and tested according to cGMP guidelines. These cells were originally obtained from Dr. Howard Green's laboratory under a material transfer agreement, and according to the vender, are of the quality sufficient to support, for example, skin gene therapy and wound healing clinical trials. Also, according to the vendor, each vial of the 3T3 cells contains a minimum of $3 \times 10^6$ cells that have been manufactured in fully compliant cleanrooms, and are certified mycoplasma free and low endotoxin. In addition, the cell bank has been fully tested for adventitious agents, including murine viruses. These cells have been screened for keratinocyte culture support and do not contain mitomycin C.

The method of the invention provides the use of feeder cells, such as the murine 3T3-J2 clone of fibroblasts. In general, without being limited to any particular phenotype, feeder cell layers are often used to support the culture of stem cells, and/or to inhibit their differentiation. A feeder cell layer is generally a monolayer of cells that is co-cultured with, and which provides a surface suitable for growth of, the cells of interest. The feeder cell layer provides an environment in which the cells of interest can grow. Feeder cells are often mitotically inactivated (e.g. by (lethal) irradiation or treatment with mitomycin C) to prevent their proliferation.

In certain embodiments, the feeder cells are appropriately screened and GMP-grade human feeder cells, e.g., those sufficient to support clinical-grade stem cell of the invention. See Crook et al. (Cell Stem Cell I(5):490-494, 2007, incorporated by reference), for GMP-grade human feeder cells grown in medium with GMP-quality FBS.

In certain embodiments, the feeder cells can be labeled by a marker that is lacking in the stem cells, such that the stem cells can be readily distinguished and isolated from the feeder cells. For example, the feeder cells can be engineered to express a fluorescent marker, such as GFP or other similar fluorescent markers. The fluorescent-labeled feeder cells can be isolated from the stem cells using, for example, FACS sorting.

Any one of a number of physical methods of separation known in the art may be used to separate the stem cells of the invention from the feeder cells. Such physical methods, other than FACS, may include various immuno-affinity methods based upon specifically expressed makers. For example, the stem cells of the invention can be isolated based on the specific stem cell markers they express, using antibodies specific for such markers.

In one embodiment, the stem cells of the invention may be isolated by FACS utilizing an antibody, for example, against one of these markers. Fluorescent activated cell sorting (FACS) can be used to detect markers characteristic of a particular cell type or lineage. As will be apparent to one skilled in the art, this may be achieved through a fluorescent labeled antibody, or through a fluorescent labeled secondary antibody with binding specificity for the primary antibody. Examples of suitable fluorescent labels includes, but is not limited to, FITC, Alexa Fluor® 488, GFP, CFSE, CFDA-SE, DyLight 488, PE, PerCP, PE-Alexa Fluor® 700, PE-Cy5 (TRI-COLOIT), PE-Cy5.5, PI, PE-Alexa Fluor*750, and PE-Cy7. The list of fluorescent markers is provided by way of example only, and is not intended to be limiting.

It will be apparent to a person skilled in the art that FACS analysis using, for example, an antibody specific for stem cell will provide a purified stem cell population. However, in some embodiments, it may be preferable to purify the cell population further by performing a further round of FACS analysis using one or more of the other identifiable markers, such as one that select against the feeders.

The use of feeder cells is considered undesirable for certain competing methods, because the presence of feeders may complicate passaging of the cells in those competing methods. For example, the cells must be separated from the feeder cells at each passage, and new feeder cells are required at each passage. In addition, the use of feeder cells may lead to contamination of the desired cells by the feeder cells.

Use of feeder layer, however, is not necessarily a disadvantage of the present invention, since the isolated stem cells of the invention are capable of being passaged as single cells, and are in fact preferably passaged as single cell clones. Thus, the potential risk of contamination by the feeders during passaging is minimized, if not eliminated.

In certain embodiments, the basement membrane matrix is a laminin-containing basement membrane matrix (e.g., MATRIGEL™ basement membrane matrix (BD Biosciences)), preferably growth factor-reduced.

In certain embodiments, the basement membrane matrix does not support 3-dimensional growth, or does not form a 3-dimensional matrix necessary to support 3-dimensional growth. Thus, when plating the basement membrane matrix, it is usually not required to deposit the basement membrane matrix in a specific shape or form on a support, such as forming a dome shape or form and maintaining such shape or form after solidification, which shape or form may be required to support 3-dimensional growth. In certain embodiments, the basement membrane matrix is evenly distributed or spread out on a flat surface or supporting structure (such as a flat bottom tissue culture dish or well).

In certain embodiments, the basement membrane matrix is first thawed and diluted in cold (e.g., about 0-4° C.) feeder cell growth medium to a proper concentration (e.g., 10%), and plated and solidified on a flat surface, such as by warming up to 37° C. in a tissue culture incubator with appropriate $CO_2$ content (e.g., about 5%). Lethally irradiated feeder cells are then plated on top of the solidified basement membrane matrix at a proper density such that settled feeder cells forms a subconfluent or confluent feeder cell layer overnight on top of the basement membrane matrix. The feeder cells are cultured in feeder cell medium, such as a medium (e.g., 3T3-J2 growth medium) comprising: a base tissue culture medium that preferably has high glucose (e.g., about 4.5 g/L), no L-glutamine, and no sodium pyruvate (e.g., DMEM (Invitrogen cat. no. 11960; high glucose (4.5 g/L), no L-glutamine, no sodium pyruvate), 10% bovine calf serum (not heat inactivated), one or more antibiotics (e.g., 1% penicillin-streptomycin), and L-glutamine (e.g., about 1.5 mM, or 1-2 mM, or 0.5-5 mM, or 0.2-10 mM, or 0.1-20 mM).

According to the methods of the invention, epithelial cell colonies becomes detectable after a few days (e.g. 3-4 days, or about 10 days) of culturing the dissociated cells from the source tissue in the subject stem cell medium.

In certain embodiments, single cells may be isolated from these epithelial cell colonies by, for example, enzyme digestion. Suitable enzymes for this purpose include trypsin, such as warm 0.25% trypsin (Invitrogen, cat. no 25200056). In certain embodiments, the enzyme digestion is substantially complete such that essentially all cells in the epithelial cell clones becomes dissociated from other cells and becomes single cells. In certain embodiments, the method comprises culturing the isolated single cells (preferably after washing and resuspending the single cells) in the modified growth medium in contact with a second population of lethally irradiated feeder cells and a second basement membrane matrix in the modified growth medium. Optionally, the isolated single cells may be passed through a cell strainer of proper size (e.g., 40 micron), before the single cells are plated on the feeder cells and basement membrane matrix.

In certain embodiments, the modified growth medium is changed periodically (e.g., once every day, once every 2, 3, or 4 days, etc.) till single cell clones or clonal expansion of the isolated single stem cells form.

In certain embodiments, a single colony of the stem cell can be isolated using, for example, a cloning ring. The isolated stem cell clone can be expanded to develop a pedigree cell line, i.e., a cell line that has been derived from a single stem cell.

In certain embodiments, single stem cells can be isolated from the clonal expansion of the single stem cell, and can be passaged again as single stem cells.

3. Medium

The invention provides various cell culture media for isolating, culturing, and/or differentiation of the subject stem cells, comprising a base medium to which a number of factors are added to produce the stem cell culture medium for reproductive tissue stem cells. The factors that may be added to the base medium or the modified medium are first described below. Several exemplary base media and modified media of the invention are then described with further details to illustrate specific non-limiting embodiments of the invention.

ROCK (Rho-Kinase) Inhibitor

While not wishing to be bound by any particular theory, the addition of a ROCK inhibitor may prevent anoikis, especially when culturing single stem cells. The ROCK inhibitor may be (R)-(+)-trans-N-(4-Pyridyl)-4-(1-aminoethyl)-cyclohexanecarboxamide) dihydrochloride monohydrate (Y-27632, Sigma-Aldrich), 5-(1,4-diazepan-1-ylsulfonyl)isoquinoline (fasudil or HA1077, Cayman Chemical), (1S)-(+)-2-methyl-1-[(4-methyl-5-isoquinolinyl)sulfonyl]-hexahydro-1H-1,4-diazepine dihydrochloride (HI 152, Tocris Bioscience), and N-(6-fluoro-1H-indazol-5-yl)-2-methyl-6-oxo-4-(4-(trifluoromethyl)phenyl)-1,4,5,6-tetrahydropyridine-3-carboxamide (GSK429286A, Stemgent).

In certain embodiments, the final concentration for Y27632 is about 1-5 µM, or 2.5 µM.

The Rho-kinase inhibitor, e.g., Y-21632, may be added to the culture medium every 1, 2, 3, 4, 5, 6, or 7 days during the first seven days of culturing the stem cells.

Wnt Agonist

The Wnt signaling pathway is defined by a series of events that occur when a Wnt protein ligand binds to a cell-surface receptor of a Frizzled receptor family member. This results in the activation of Dishevelled (Dsh) family proteins which inhibit a complex of proteins that includes axin, GSK-3, and the protein APC to degrade intracellular β-catenin. The resulting enriched nuclear β-catenin enhances transcription by TCF/LEF family of transcription factors. A "Wnt agonist" as used herein includes an agent that directly or indirectly activates TCF/LEF-mediated transcription in a cell, such as through modulating the activity of any one of the proteins/genes in the Wnt signaling cascade (e.g., enhancing the activity of a positive regulator of the Wnt signaling pathway, or inhibiting the activity of a negative regulator of the Wnt signaling pathway).

Wnt agonists are selected from true Wnt agonists that bind and activate a Frizzled receptor family member including any and all of the Wnt family proteins, an inhibitor of intracellular β-catenin degradation, and activators of TCF/LEF. The Wnt agonist may stimulate a Wnt activity in a cell by at least about 10%, at least about 20%, at least about 30%, at least about 50%, at least about 70%, at least about 90%, at least about 100%, at least about 2-fold, 3-fold, 5-fold, 10-fold, 20-fold, 50-fold, 100-fold, 200-fold, 500-fold, or 1000-fold or more relative to a level of the Wnt activity in the absence of the Wnt agonist. As is known to a person of skill in the art, a Wnt activity can be determined by measuring the transcriptional activity of Wnt, for example by pTOPFLASH and pFOPFLASH Tcf luciferase reporter constructs (see Korinek et al, Science 275: 1784-1787, 1997, incorporated herein by reference).

Representative Wnt agonist may comprise a secreted glycoprotein including Wnt-1/Int-1, Wnt-2/Irp (Int-1-related Protein), Wnt-2b/13, Wnt-3/Int-4, Wnt-3a (R&D systems), Wnt-4, Wnt-5a, Wnt-5b, Wnt-6 (Kirikoshi et al, Biochem. Biophys. Res. Com., 283:798-805, 2001), Wnt-7a (R&D systems), Wnt-7b, Wnt-8a/8d, Wnt-8b, Wnt-9a/14, Wnt-9b/14b/15, Wnt-10a, Wnt-10b/12, Wnt-11, and Wnt-16. An overview of human Wnt proteins is provided in "The Wnt Family of Secreted Proteins," R&D Systems Catalog, 2004 (incorporated herein by reference).

Further Wnt agonists include the R-spondin family of secreted proteins, which is implicated in the activation and regulation of Wnt signaling pathway, and which comprises at least 4 members, namely R-spondin 1 (NU206, Nuvelo, San Carlos, Calif.), R-spondin 2 (R&D systems), R-spondin 3, and R-spondin 4. Wnt agonists also include Norrin (also known as Norrie Disease Protein or NDP) (R&D systems), which is a secreted regulatory protein that functions like a Wnt protein in that it binds with high affinity to the Frizzled-4 receptor and induces activation of the Wnt signaling pathway (Kestutis Planutis et al, BMC Cell Biol. 8: 12, 2007).

Wnt agonists further include a small-molecule agonist of the Wnt signaling pathway, an aminopyrimidine derivative (N4-[(2H-1,3-benzodioxol-5-yl)methyl]-6-(3-methoxyphenyl)pyrimidine-2,4-diamine) of the following structure, as described in Liu et al. (Angew Chem. Int. Ed. Engl. 44 13): 1987-1990, 2005, incorporated herein by reference).

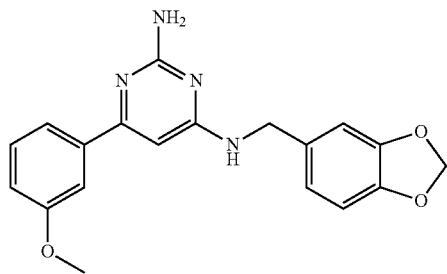 [SMILES: COc1cccc(-c2cc(NCc3ccc4c(c3)OCO4)nc(N)n2)c1]

GSK-inhibitors comprise small-interfering RNAs (siRNA, Cell Signaling), lithium (Sigma), kenpaullone (Biomol International, Leost et al., Eur. J. Biochem. 267:5983-5994, 2000), 6-Bromoindirubin-30-acetoxime (Meyer et al., Chem. Biol. 10:1255-1266, 2003), SB 216763, and SB 415286 (Sigma-Aldrich), and FRAT-family members and FRAT-derived peptides that prevent interaction of GSK-3 with axin. An overview is provided by Meijer et al. (Trends in Pharmacological Sciences 25:471-480, 2004, incorporated herein by reference). Methods and assays for determining a level of GSK-3 inhibition are known in the art, and may comprise, for example, the methods and assay as described in Liao et al. (Endocrinology 145(6):2941-2949, 2004, incorporated herein by reference).

In certain embodiments, Wnt agonist is selected from: one or more of a Wnt family member, R-spondin 1-4 (such as R-spondin 1), Norrin, Wnt3a, Wnt-6, and a GSK-inhibitor.

In certain embodiments, the Wnt agonist comprises or consists of R-spondin 1. R-spondin 1 may be added to the subject culture medium at a concentration of at least about 50 ng/mL, at least about 75 ng/mL, at least about 100 ng/mL, at least about 125 ng/mL, at least about 150 ng/mL, at least about 175 ng/mL, at least about 200 ng/mL, at least about 300 ng/mL, at least about 500 ng/mL. In certain embodiments, R-spondin 1 is about 125 ng/mL.

In certain embodiments, any of the specific protein-based Wnt agonist referenced herein, such as R-spondin 1 to R-spondin 4, any Wnt family member, etc. may be replaced by a natural, synthetic, or recombinantly produced homologs or fragments thereof that retain at least about 80%, 85%, 90%, 95%, 99% of the respective Wnt agonist activity, and/or homologs or fragments thereof that share at least about 60%, 70%, 80%, 90%, 95%, 97%, 99% amino acid sequence identity as measured by any art recognized sequence alignment software based on either a global alignment technique (e.g., the Needleman-Wunsch algorithm) or a local alignment technique (e.g., the Smith-Waterman algorithm). The sequences of the representative Wnt agonist referenced herein are represented in SEQ ID NOs. 10-17.

During culturing of the subject stem cells, the Wnt family member may be added to the medium every day, every second day, every third day, while the medium is refreshed, e.g., every 1, 2, 3, 4, 5, or more days.

In certain embodiments, a Wnt agonist is selected from the group consisting of: an R-spondin, Wnt-3a and Wnt-6, or combinations thereof. In certain embodiments, an R-spondin and Wnt-3a are used together as Wnt agonist. In certain embodiments, R-spondin concentration is about 125 ng/mL, and Wnt3a concentration is about 100 ng/mL.

Mitogenic Growth Factor

Mitogenic growth factors suitable for the invention may include a family of growth factors comprising epidermal growth factor (EGF) (Peprotech), Transforming Growth Factor-α (TGFa, Peprotech), basic Fibroblast Growth Factor (bFGF, Peprotech), brain-derived neurotrophic factor (BDNF, R&D Systems), and Keratinocyte Growth Factor (KGF, Peprotech).

EGF is a potent mitogenic factor for a variety of cultured ectodermal and mesodermal cells, and has a profound effect on the differentiation of specific cells in vivo and in vitro, and of some fibroblasts in cell culture. The EGF precursor exists as a membrane-bound molecule, which is proteolytically cleaved to generate the 53-amino acid peptide hormone that stimulates cells. EGF may be added to the subject culture medium at a concentration of between 1-500 ng/mL. In certain embodiments, final EGF concentration in the medium is at least about 1, 2, 5, 10, 20, 25, 30, 40, 45, or 50 ng/mL, and is not higher than about 500, 450, 400, 350, 300, 250, 200, 150, 100, 50, 30, 20 ng/mL. In certain embodiments, final EGF concentration is about 1-50 ng/mL, or about 2-50 ng/mL, or about 5-30 ng/mL, or about 5-20 ng/mL, or about 10 ng/mL.

The same concentrations may be used for an FGF, such as FGF10 or FGF7. If more than one FGF is used, for example FGF7 and FGF 10, the concentration of FGF above may refer to the total concentration of all FGF used in the medium.

In certain embodiments, any of the specific mitogenic growth factors referenced herein, such as EGF, TGFa, bFGF, BDNF, KGF, etc. may be replaced by a natural, synthetic, or recombinantly produced homologs or fragments thereof that retain at least about 80%, 85%, 90%, 95%, 99% of the respective mitogenic growth factor activity, and/or homologs or fragments thereof that share at least about 60%, 70%, 80%, 90%, 95%, 97%, 99% amino acid sequence identity as measured by any art recognized sequence alignment software based on either a global alignment technique (e.g., the Needleman-Wunsch algorithm) or a local alignment technique (e.g., the Smith-Waterman algorithm).

The sequences of the representative mitogenic growth factors referenced herein are represented in SEQ ID NOs. 18-27.

During culturing of the subject stem cells, the mitogenic growth factor may be added to the culture medium every day, every 2nd day, while the culture medium is refreshed, e.g., every day.

Any member of the bFGF family may be used. In certain embodiments, FGF7 and/or FGF10 is used. FGF7 is also known as KGF (Keratinocyte Growth Factor). In certain embodiments, a combination of mitogenic growth factors, such as EGF and KGF, or EGF and BDNF, is added to the subject culture medium. In certain embodiments, a combination of mitogenic growth factors, such as EGF and KGF, or EGF and FGF10, is added to the subject culture medium.

BMP Inhibitor

Bone Morphogenetic Proteins (BMPs) bind as a dimeric ligand to a receptor complex consisting of two different receptor serine/threonine kinases, type I and type II receptors. The type II receptor phosphorylates the type I receptor, resulting in the activation of this receptor kinase. The type I receptor subsequently phosphorylates specific receptor substrates (such as SMAD), resulting in a signal transduction pathway leading to transcriptional activity.

A BMP inhibitor as used herein includes an agent that inhibits BMP signaling through its receptors. In one embodiment, a BMP inhibitor binds to a BMP molecule to form a complex such that BMP activity is neutralized, for example, by preventing or inhibiting the binding of the BMP molecule to a BMP receptor. Examples of such BMP inhibitors may include an antibody specific for the BMP ligand, or an antigen-binding portion thereof. Other examples of such BMP inhibitors include a dominant negative mutant of a BMP receptor, such as a soluble BMP receptor that binds the BMP ligand and prevents the ligand from binding to the natural BMP receptor on the cell surface.

Alternatively, the BMP inhibitor may include an agent that acts as an antagonist or reverse agonist. This type of inhibitor binds with a BMP receptor and prevents binding of a BMP to the receptor. An example of such an agent is an antibody that specifically binds a BMP receptor and prevents binding of BMP to the antibody-bound BMP receptor.

In certain embodiments, the BMP inhibitor inhibits a BMP-dependent activity in a cell to at most 90%, at most 80%, at most 70%, at most 50%, at most 30%, at most 10%, or about 0% (near complete inhibition), relative to a level of a BMP activity in the absence of the inhibitor. As is known to one of skill in the art, a BMP activity can be determined by, for example, measuring the transcriptional activity of BMP as exemplified in Zilberberg et al. ("A rapid and sensitive bioassay to measure bone morphogenetic protein activity," BMC Cell Biology 8:41, 2007, incorporated herein by reference).

Several classes of natural BMP-binding proteins are known, including Noggin (Peprotech), Chordin, and chordin-like proteins comprising a chordin domain (R&D systems) comprising chordin domains, Follistatin and follistatin-related proteins comprising a follistatin domain (R&D systems) comprising a follistatin domain, DAN and DAN-like proteins comprising a DAN Cystine-knot domain {e.g., Cerberus and Gremlin) (R&D systems), sclerostin/SOST (R&D systems), decorin (R&D systems), and alpha-2 macroglobulin (R&D systems) or as described in U.S. Pat. No. 8,383,349. An exemplary BMP inhibitor for use in a method of the invention is selected from Noggin, DAN, and DAN-like proteins including Cerberus and Gremlin (R&D systems). These diffusible proteins are able to bind a BMP ligand with varying degrees of affinity, and inhibit BMPs' access to their signaling receptors.

Any of the above-described BMP inhibitors may be added either alone or in combination to the subject culture medium when desirable.

In certain embodiments, the BMP inhibitor is Noggin. Noggin may be added to the respective culture medium at a concentration of at least about 10 ng/mL, or at least about 20 ng/mL, or at least about 50 ng/mL, or at least about 100 ng/mL (e.g., 100 ng/mL).

In certain embodiments, any of the specific BMP inhibitors referenced herein, such as Noggin, Chordin, Follistatin, DAN, Cerberus, Gremlin, sclerostin/SOST, decorin, and alpha-2 macroglobulin may be replaced by a natural, synthetic, or recombinantly produced homologs or fragments thereof that retain at least about 80%, 85%, 90%, 95%, 99% of the respective BMP inhibiting activity, and/or homologs or fragments thereof that share at least about 60%, 70%, 80%, 90%, 95%, 97%, 99% amino acid sequence identity as measured by any art recognized sequence alignment software based on either a global alignment technique (e.g., the Needleman-Wunsch algorithm) or a local alignment technique (e.g., the Smith-Waterman algorithm).

The sequences of the representative BMP inhibitors referenced herein are represented in SEQ ID NOs. 1-9.

During culturing of the subject stem cells, the BMP inhibitor may be added to the culture medium every day, every 2nd day, every 3rd day, or every 4th day, while the culture medium is refreshed every day, every second day, every third day, or every fourth day as appropriate.

BRAF Inhibitors

BRAF inhibitors that may be used in accordance with the embodiments described herein may include any agent which selectively inhibits at least a portion of the biological activity (e.g., signal transduction activity) of a wild type BRAF or a mutant form of BRAF (e.g., $BRAF^{V600E}$, $BRAF^{V600K}$, $BRAF^{V600D}$, $BRAF^{V600L}$, $BRAF^{V600R}$). In some aspects, the BRAF inhibitors may be selective for BRAF alone, or may have inhibitory activity against one or more additional targets in the RAF/MEK/ERK pathway. For example in one aspect, the BRAF inhibitor may be a RAF kinase inhibitor, i.e., the inhibitor may have inhibitory activity against RAF kinases such as ARAF, CRAF, or both, in addition to BRAF. In certain embodiments, the BRAF inhibitor is selected to have increased paradoxical MAPK activation activity. As such, the BRAF inhibitors used in accordance with the embodiments described herein may act as a MAPK paradox activator, meaning that the BRAF inhibitor causes an increase in MAPK signaling. In some aspects, a MAPK paradox activator is a BRAF inhibitor that exhibits increased MAPK signaling when the target BRAF kinase is a wild type BRAF kinase.

Several BRAF kinase inhibitors have been described in the art, any of which may be suitable for use in the methods, dressings and compositions described herein. Suitable BRAF inhibitors may include, but are not limited to, 1,2-di-cyclylsubstituted alkyne compounds or derivatives; 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine); 2,6-disubstituted quinazoline, quinoxaline, quinoline, and isoquinoline compounds or derivatives; 4-amino-5-oxo-8-phenyl-5H-pyrido-[2,3-D]-pyrimidine compounds or derivatives; 4-amino-thieno[3,2-C]pyridine-7-carboxylic acid compounds or derivatives; 5-(4-aminophenyl)-isoquinoline compounds or derivatives; benzene sulfonamide thiazole compounds or derivatives; benzimidazole compounds or derivatives; bicyclic compounds or derivatives; bridged, bicyclic heterocyclic or spiro bicyclic heterocyclic derivatives of pyrazolo[1,5-a]pyrimidine compounds or derivatives; cinnamide and hydro-cinnamide compounds or derivatives; di-substituted imidazole compounds or derivatives; fused tricyclic pyrazolo[1,5-a]pyrimidine compounds or derivatives; heteroaryl compounds or derivatives; heterocyclic compounds or derivatives; 1H-benzo [D] imidazole compounds or derivatives; imidazo [4,5-B] pyridine compounds or derivatives; N-(6-aminopytidin-3-yl)-3-(sulfonamido) benzamide compounds or derivatives; N-[3-(1-amino-5,6,7,8-tetrahydro-2,4,4B-triazafluoren-9-yl)-phenyl] benzamide compounds or derivatives; nitrogen-containing bicyclic heteroaryl compounds or derivatives; N-oxides of heterocyclic substituted bisarylurea compounds or derivatives; omega-carboxylaryl substituted diphenyl urea compounds or derivatives; oxazole compounds or derivatives; phenethylamide compounds or derivatives; phenylsulfonamide-substituted, pyrazolo[1,5-a] pyrimidine compounds or derivatives; phenyltriazole compounds or derivatives; heterocyclic compounds or derivatives; 1 h-pyrazolo[3,4-b] pyridine compounds or derivatives; purine compounds or derivatives; pyrazole [3,4-B] pyridine compounds or derivatives; pyrazole compounds or derivatives; pyrazoline compounds or derivatives; pyrazolo [3,4-b] pyridines, pyrrolo [2,3-b] pyridine compounds or derivatives; pyrazolo [3,4-d]pyrimidine compounds or derivatives; pyrazolo [5,1-c] [1,2,4] triazine compounds or derivatives; pyrazolyl compounds or derivatives; pyrimidine compounds or derivatives; pyrrol compounds or derivatives; pyrrolo [2,3-B] pyridine compounds or derivatives; substituted 6-phenyl-pyrido [2,3-D] pyrimidin-7-ones compounds or derivatives; substituted benzazole compounds or derivatives; substituted benzimidazole compounds or derivatives; substituted bisaryl-urea compounds or derivatives; thienopyridine compounds or derivatives; thienopyrimidine, thienopyridine, or pyrrolopyrimidine compounds or derivatives; thiophene amide compounds or derivatives, and any other suitable aryl and/or heteroaryl compounds or derivatives. In some aspects, the suitable BRAF inhibitors described herein may include the compound or derivative itself or may be a pharmaceutically acceptable salt or solvate thereof.

Several patents and patent applications disclose exemplar BRAF inhibitors that may be used in accordance with the embodiments described herein including, but not limited to, International Patent Application Publication Nos WO2011117381, WO2011119894, WO2011117381, WO2011097594, WO2011097526, WO2011085269, WO2011090738, WO2011025968, WO2011025927, WO2011023773, WO2011028540, WO2010111527, WO2010104973, WO2010100127, WO2010078408, WO2010065893, WO2010032986, WO2009115572, WO2009108838, WO2009111277, WO2009111278, WO2009111279, WO2009111280, WO2009108827, WO2009111260, WO2009100536, WO2009059272, WO2009039387, WO2009021869, WO2009006404, WO2009006389, WO2008140850, WO2008079277, WO2008055842, WO2008034008, WO2008115263, WO2008030448, WO2008028141, WO2007123892, WO2007115670, WO2007090141, WO2007076092, WO2007067444, WO2007056625, WO2007031428, WO2007027855, WO2007002433, WO2007002325, WO2006125101, WO2006124874, WO2006124780, WO2006102079, WO2006108482, WO2006105844, WO2006084015, WO2006076706, WO2006050800, WO2006040569, WO2005112932, WO2005075425, WO2005049603, WO2005037285, WO2005037273, WO2005032548; and U.S. Pat. Nos. 8,642,759, 8,557,830, 8,504,758, 7,863,288, 7,491,829, 7,482,367, and 7,235,576; the specifications of all of which are hereby incorporated by reference as if fully set forth herein.

In certain embodiments, the BRAF inhibitor may be selected from a group of molecules selected from AMG542, ARQ197, ARQ736, AZ628, CEP-32496, GDC-0879, GSK1120212, GSK2118436 (dabrafenib, Tafinlar), LGX818 (encorafenib), NMS-P186, NMS-P349, NMS-P383, NMS-P396, NMS-P730, PLX3603 (RO5212054), PLX4032 (vemurafenib, Zelboraf), PLX4720 (Difluorophenyl-sulfonamine), PF-04880594, PLX4734, RAF265 (CHIR-265), 804987655, SB590885, sorafenib, sorafenib tosylate, or XL281 (BMS-908662).

In some embodiments, the BRAF inhibitor has a structure of Formula (I) or Formula (II):

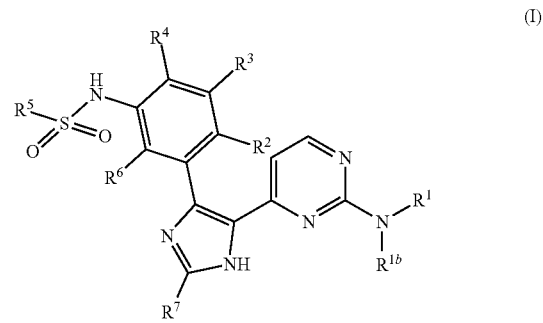

(I)

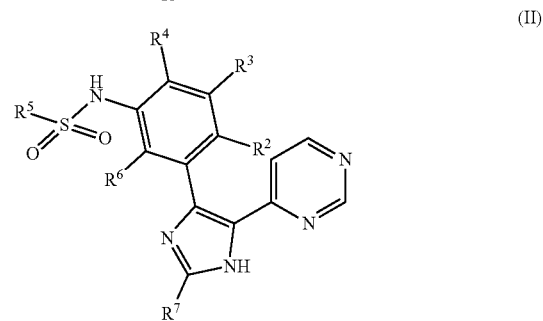

(II)

wherein:

$R^1$ is H, C3-C6 cycloalkyl optionally substituted with cyano, C1-C3 alkyl optionally substituted with cyano, —C(O)NH$_2$, hydroxy, —X$^1$NHC(O)OR$^1$a, —X$^1$NHC(O)NHR$^1$a, where X$^1$ is C1-C4 alkylene optionally substituted with 1 to 3 groups each independently selected from halo, C1-C4 alkyl or halosubstituted C1-C4 alkyl and R$^1$a is H, C1-C4 alkyl, or halosubstituted C1-C4 alkyl;

$R^{1b}$ is H or methyl;

$R^2$ is H or halogen;

$R^3$ is H, halogen, C1-C4 alkoxy, C1-C4 alkyl, halosubstituted C1-C4 alkoxy, or halosubstituted C1-C4 alkyl;

$R^4$ is halogen, H, or C1-C4 alkyl;

$R^5$ is C1-C6 alkyl, C3-C6 cycloalkyl, C3-C8 branched alkyl, halosubstituted C1-C6 alkyl, halosubstituted C3-C8 branched alkyl, C3-C6 cycloalkyl-(C1-C3)-alkylene, or phenyl, where said phenyl is optionally substituted with 1 to 3 substituents each independently selected form halo, CH$_3$, or CF$_3$;

R$^6$ is H, C1-C4 alkyl, or halogen; and

R$^7$ is H, C1-C6 alkyl, C3-C6 cycloalkyl, 1-methyl-(C3-C6)-cycloalkyl, 1-(halosubstituted-methyl)-(C3-C6)-cycloalkyl, C3-C8 branched alkyl, halosubstituted C1-C6 alkyl, halosubstituted C3-C8 branched alkyl, or phenyl, where said phenyl is optionally substituted with 1 to 3 substituents selected form halogen, C1-C4 alkyl or halosubstituted C1-C4 alkyl, preferably wherein R$^7$ is H, C1-C6 alkyl, C3-C6 cycloalkyl, 1-methyl-(C3-C6)-cycloalkyl, C3-C8 branched alkyl, or phenyl, where said phenyl is optionally substituted with 1 to 3 substituents selected form halogen, C1-C4 alkyl or halosubstituted C1-C4 alkyl; or a pharmaceutically acceptable salt thereof.

In one particular embodiment of a compound of Formula (I), R$^1$ is C1-C3 alkyl optionally substituted with cyano, —C(O)NH$_2$, hydroxy, —X$^1$NHC(O)OR$^1$a, where X$^1$ is C1-C4 alkylene optionally substituted with 1 to 3 groups each independently selected from halo, C1-C4 alkyl, or halosubstituted C1-C4 alkyl and R$^1$a is H, C1-C4 alkyl, or halosubstituted C1-C4 alkyl;

R$^2$ is H or halogen;

R$^3$ is H, halogen, C1-C4 alkoxy, C1-C4 alkyl, halosubstituted C1-C4 alkoxy or halosubstituted C1-C4 alkyl;

R$^4$ is halogen, H, or C1-C4 alkyl;

R$^5$ is C1-C6 alkyl, C3-C6 cycloalkyl, C3-C8 branched alkyl, halosubstituted C1-C6 alkyl, or halosubstituted C3-C8 branched alkyl;

R$^6$ is H, C1-C4 alkyl, or halogen; and

R$^7$ is H, C1-C6 alkyl, C3-C6 cycloalkyl, 1-methyl-(C3-C6)-cycloalkyl, 1-(halosubstituted-methyl)-(C3-C6)-cycloalkyl, C3-C8 branched alkyl, halosubstituted C1-C6 alkyl, or halosubstituted C3-C8 branched alkyl or phenyl, where said phenyl is optionally substituted with 1 to 3 substituents selected form halogen, C1-C4 alkyl or halosubstituted C1-C4 alkyl, preferably wherein R$^7$ is H, C1-C6 alkyl, C3-C6 cycloalkyl, 1-methyl-(C3-C6 cycloalkyl, or phenyl, wherein said phenyl is optionally substituted with 1 to 3 substituents selected form halogen, C1-C4 alkyl or halosubstituted C1-C4 alkyl; or a pharmaceutically acceptable salt thereof.

In a preferred embodiment, a compound of Formula (II) is provided wherein

R$^1$ is —CH$_2$—(S)—CH(CH$_3$)NHC(O)OCH$_3$;

R$^{1b}$ is H;

R$^2$ is H;

R$^3$ is Cl;

R$^4$ is H;

R$^5$ is CH$_3$;

R$^6$ is F; and

R$^7$ is isopropyl, or a pharmaceutically acceptable salt thereof (also referred to herein as "LGX818" or "encorafenib").

In another embodiment, compounds of Formula (II) are provided wherein

R$^2$ is H or F;

R$^3$ is H, halogen, C1-C2 alkoxy, C1-C2 alkyl, halosubstituted C1-C2 alkoxy, or halosubstituted C1-C2 alkyl;

R$^4$ is H or methyl;

R$^5$ is C1-C4 alkyl, C3-C6 cycloalkyl, C3-05 branched alkyl, halosubstituted C1-C4 alkyl, halosubstituted C3-C6 branched alkyl, or C3-C6 cycloalkyl-(C1-C3)-alkylene;

R$^6$ is H, C1-C2 alkyl, or halogen; and

R$^7$ is C3-C6 cycloalkyl, 1-methyl-(C3-C6)-cycloalkyl, or C3-C6 branched alkyl; or a pharmaceutically acceptable salt thereof.

In another embodiment, compounds of Formula (II) are provided wherein

R$^2$ is H;

R$^3$ is H, Cl, F, methoxy, methyl, or difluoromethoxy;

R$^4$ is H;

R$^5$ is methyl, cyclopropyl, ethyl, propyl, isopropyl, sec-butyl, isobutyl, trifluoromethyl, or 3,3,3-trifluoropropyl;

R$^6$ is H, methyl, F, or Cl; and

R$^7$ is t-butyl, cyclopropyl, or 1-methylcyclopropyl; or a pharmaceutically acceptable salt thereof.

In some embodiments, the BRAF inhibitor is a compound of Formula (III):

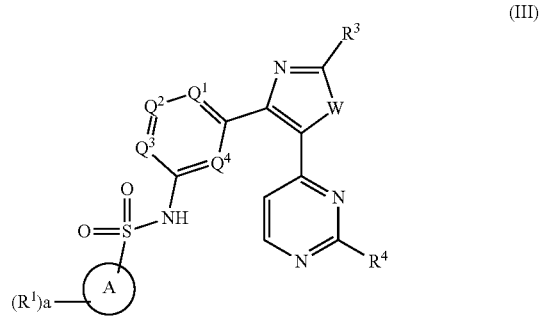

(III)

wherein:

a is 0, 1, 2 or 3;

each R$^1$ is the same or different and is independently selected from halo, alkyl, haloalkyl, —OR$^6$, —CO$_2$R$^6$, —NR$^6$R$^7$, and —CN;

Ring A is selected from C3-C6 cycloalkyl, phenyl, 5-6 membered heterocycle and 5-6 membered heteroaryl, said heterocycle and said heteroaryl each having 1 or 2 heteroatoms selected from N, O and S;

each of Q$^1$, Q$^2$, Q$^3$ and Q$^4$ is CH, CR$^2$ or N, wherein not more than one of Q$^1$, Q$^2$, Q$^3$ and Q$^4$ is N;

each R$^2$ is the same or different and is independently selected from halo, alkyl, haloalkyl, and —OR$^6$;

W is selected from —O— and —S—;

R$^3$ is selected from H, alkyl, haloalkyl-, -alkylene-OH, —NR$^6$R$^7$, —C3-C6 cycloalkyl, -alkylene-C(O)—OH, -alkylene-NH$_2$, and Het;

wherein when R$^3$ is C3-C6 cycloalkyl, said C3-C6 cycloalkyl is optionally substituted with 1 or 2 substituents which are the same or different and are independently selected from halo, C1-C3 alkyl, halo-(C1-C3)-alkyl, OH, O—(C1-C3)-alkyl, oxo, S—(C1-C3)-alkyl), SO$_2$, NH$_2$, N(H)(C1-C3)-alkyl and N(C1-C3alkyl)$_2$;

Het is a 5-6 membered heterocycle having 1 or 2 heteroatoms selected from N, O and S and optionally substituted with 1 or 2 substituents which are the same or different and are each independently selected from halo, C1-C3 alkyl, halo-(C1-C3)-alkyl, O—(C1-C3)-alkyl, C1-C3 alkylene-O—(C1-C3)-alkyl, OH, C1-C3 alkylene-OH, oxo, SO$_2$((C1-C3)-alkyl), C1-C3 alkylene-SO$_2$((C1-C3)-alkyl), NH$_2$, N(H)((C1-C3)-alkyl), N(C1-C3 alkyl)$_2$, CN, and —CH$_2$CN;

R$^4$ is selected from H, alkyl, haloalkyl, alkenyl, —OR$^6$, —R$^5$—OR$^6$, —R$^5$—CO$_2$R$^6$, —R$^5$—SO$_2$R$^6$, —R$^5$-Het, —$R^5$—C(O)-Het, —N(H)$R^8$, —N(CH3)$R^8$, and —$R^5$—N$R^6R^7$; each $R^5$ is the same or different and is independently C1-C4 alkylene;

each $R^6$ and each $R^7$ is the same or different and is independently selected from H, alkyl, haloalkyl, —C(O)-alkyl, and —C(O)-cycloalkyl;

$R^8$ is selected from H, alkyl (optionally substituted by —OH), haloalkyl, C3-C6 cycloalkyl, —$R^5$—(C3-C6)-cycloalkyl, Het$^2$, —$R^5$-Het$^2$, —$R^5$—O$R^6$, —$R^5$—O—$R^5$—O$R^6$, —$R^5$—C(O)$_2R^6$, —$R^5$—C(O)N$R^6R^7$, —$R^5$—N(H)C(O)—$R^6$, —$R^5$—N(H)C(O)—$R^5$—O$R^6$, —$R^5$—N(H)C(O)$_2$—$R^5$—$R^5$—N$R^5R^7$, —$R^5$—S(O)$_2R^6$, —$R^5$—CN, and —$R^5$—N(H)S(O)$_2R^6$;

wherein when $R^8$ is C3-C6 cycloalkyl, said C3-C6 cycloalkyl is optionally substituted with 1 or 2 substituents which are the same or different and are independently selected from halo, C1-C3 alkyl, halo-(C1-C3)-alkyl, OH, O—(C1-C3)-alkyl, oxo, S—(C1-C3)-alkyl, SO$_2$(C1-C3 alkyl), NH$_2$, N(H)—(C1-C3)-alkyl and N(C1-C3 alkyl)$_2$, and N(H)SO$_2$—(C1-C3)-alkyl; and Het$^2$ is a 4-6 membered heterocycle having 1 or 2 heteroatoms selected from N, O and S and optionally substituted with 1, 2, 3, 4 or 5 C1-C3 alkyl or 1 or 2 substituents which are the same or different and are each independently selected from halo, C1-C3 alkyl, halo-(C1-C3)-alkyl, O—(C1-C3)-alkyl, C1-C3 alkylene-O—(C1-C3 alkyl), OH, C1-C3 alkylene-OH, oxo, SO$_2$(C1-C3 alkyl), C1-C3 alkylene-SO$_2$(C1-C3 alkyl), NH$_2$, N(H)—(C1-C3 alkyl), N(C1-C3 alkyl)$_2$, N(H)SO$_2$—(C1-C3 alkyl), C(O)(C1-C3 alkyl), CO$_2$(C1-C4 alkyl), CN, and —CH$_2$CN;

and $R^9$ and $R^1$9 are independently selected from H and alkyl, and pharmaceutically acceptable salts thereof.

In a preferred embodiment, a compound of Formula (III) is provided wherein a is 2;
$R^1$ is F;
each $R^2$ is F;
$R^3$ is t-butyl;
$R^4$ is N(H)$R^8$;
$R^8$ is H; and
W is S (referred to herein as "GSK2118436," "dabrafenib," or "Tafinlar"), or a pharmaceutically acceptable salt thereof.

In some embodiments, the BRAF inhibitor is a compound of Formula (IV):

(IV)

wherein:
$R^2$, $R^4$, $R^5$, and $R^6$ are independently selected from the group consisting of hydrogen, halogen, optionally substituted lower alkyl, optionally substituted lower alkenyl, optionally substituted lower lkynyl, optionally substituted cycloalkyl, optionally substituted heterocycloalkyl, optionally substituted aryl, optionally substituted heteroaryl, —CN, —NO$_2$, —CR$^a$R$^b$R$^{26}$, and -L$R^{26}$;

$R^3$ is selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —CN, —NO$_2$, —CR$^a$R$^b$R$^{26}$, -L$R^{26}$ and -A-Ar-L1-R$^{24}$;

A is selected from the group consisting of —O—, —S—, —CR$^a$R$^b$—, —NR$^1$—, —C(O)—, —C(S)—, —S(O)—, and —S(O)$_2$—;

$R^1$ is selected from the group consisting of hydrogen, lower alkyl, cycloalkyl, heterocycloalkyl, aryl, heteroaryl, —C(O)$R^7$, —C(S)$R^7$, —S(O)$_2R^7$, —C(O)NH$R^7$, —C(S)NH$R^7$, and —S(O)$_2$NH$R^7$, wherein lower alkyl is optionally substituted with one or more substituents selected from the group consisting of fluoro, —OH, —NH$_2$, lower alkoxy, lower alkylthio, mono-alkylamino, di-alkylamino, and —N$R^8R^9$, wherein the alkyl chain(s) of lower alkoxy, lower alkylthio, mono-alkylamino, or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl chain carbon bound to O of alkoxy, S of thioalkyl or N of mono- or di-alkylamino is fluoro, further provided, however, that when $R^1$ is lower alkyl, any substitution on the lower alkyl carbon bound to the N of —N$R^1$— is fluoro, and wherein cycloalkyl, heterocycloalkyl, aryl or heteroaryl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino; $R^7$ is selected from the group consisting of lower alkyl, cycloalkyl, heterocycloalkyl, aryl, and heteroaryl, wherein lower alkyl is optionally substituted with one or more substituents selected from the group consisting of fluoro, —OH, —NH$_2$, lower alkoxy, lower alklylthio, mono-alkylamino, di-alkylamino, and —K$R^8R^9$, provided, however, that any substitution of the alkyl carbon bound to the N of —C(O)NH$R^7$, —C(S)NH$R^7$ or —S(O)$_2$NH$R^7$ is fluoro, wherein the alkyl chain(s) of lower alkoxy, lower alkylthio, mono-alkylamino, or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl chain carbon bound to O of alkoxy, S of thioalkyl or N of mono- or di-alkylamino is fluoro, and wherein cycloalkyl, heterocycloalkyl, aryl and heteroaryl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

Ar is selected from the group consisting of optionally substituted arylene and optionally substituted heteroarylene;

L at each occurrence is independently selected from the group consisting of -(alk)$_a$-S-(alk)$_b$-, -(alk)$_a$-O-(alk)$_b$-, -(alk)$_a$-NR$^{25}$-(alk)$_b$-, -(alk)$_a$-C(O)-(alk)$_b$-, -(alk)$_a$-C(S)-(alk)$_b$-, -(aUc)$_a$-S(O)-(alk)$_b$-, -(alk)$_a$-S(O)$_2$-(alk)$_b$-, -(alk)$_a$-OC(O)-(alk)$_b$-, -(alk)$_a$-C(O)O-(alk)$_b$-, -(alk)$_a$-OC(S)-(alk)$_b$-, -(alk)$_a$-C(S)O-(alk)$_b$-, -(alk)$_a$-C(O)NR$^{25}$-(alk)$_b$-, -(alk)$_a$-C(S)NR$^{25}$-(alk)$_b$-, -(alk)$_a$-S(O)$_2$NR$^{25}$-(alk)$_b$-, -(alk)$_a$-NR$^{25}$C(O)-(alk)$_b$-, -(alk)$_a$-NR$^{25}$C(S)-(alk)$_b$-, -(alk)$_a$-NR$^{25}$S(O)$_2$-(alk)$_b$-, -(alk)$_a$-NR$^{25}$C(O)O-(alk)$_b$-, -(alk)$_a$-

$NR^{25}C(S)O\text{-}(alk)_b\text{-}$, $\text{-}(alk)_a\text{-}OC(O)NR^{25}\text{-}(alk)_b\text{-}$, $\text{-}(alk)_a\text{-}OC(S)NR^{25}\text{-}(alk)_b\text{-}$, $\text{-}(alk)_a\text{-}NR^{25}C(O)NR^{25}\text{-}(alk)_b\text{-}$, $\text{-}(alk)_a\text{-}NR^{25}C(S)NR^{25}\text{-}(alk)_b\text{-}$, and $\text{-}(alk)_a\text{-}NR^{25}S(O)_2NR^{25}\text{-}(alk)_b\text{-}$; a and b are independently 0 or 1; alk is C1-C3 alkylene or C1-C3 alkylene substituted with one or more substituents selected from the group consisting of fluoro, —OH, —NH$_2$, lower alkyl, lower alkoxy, lower alkylthio, mono-alkylamino, di-alkylamino, and —NR$^8$R$^9$, wherein lower alkyl or the alkyl chain(s) of lower alkoxy, lower alkylthio, mono-alkylamino or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution of the alkyl chain carbon bound to O of alkoxy, S of thioalkyl or N of mono- or di-alkylamino is fluoro;

L1 is —(CR$^a$R$^b$)$_v$— or L, wherein v is 1, 2, or 3; wherein R$^a$ and R$^b$ at each occurrence are independently selected from the group consisting of hydrogen, fluoro, —OH, —NH$_2$, lower alkyl, lower alkoxy, lower alklylthio, mono-alkylamino, di-alkylamino, and —NR$^8$R$^9$, wherein the alkyl chain(s) of lower alkyl, lower alkoxy, lower alkylthio, mono-alkylamino, or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl chain carbon bound to O of alkoxy, S of thioalkyl or N of mono- or di-alkylamino is fluoro; or any two of R$^a$ and R$^b$ on the same or different carbons combine to form a 3-7 membered monocyclic cycloalkyl or 5-7 membered monocyclic heterocycloalkyl and any others of R$^a$ and R$^b$ are independently selected from the group consisting of hydrogen, fluoro, —OH, —NH$_2$, lower alkyl, lower alkoxy, lower alklylthio, mono-alkylamino, di-alkylamino, and —NR$^8$R$^9$, wherein the alkyl chain(s) of lower alkyl, lower alkoxy, lower alkylthio, mono-alkylamino, or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl chain carbon bound to O of alkoxy, S of thioalkyl or N of mono- or di-alkylamino is fluoro, and wherein the 3-7 membered monocyclic cycloalkyl or 5-7 membered monocyclic heterocycloalkyl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

R$^8$ and R$^9$ combine with the nitrogen to which they are attached to form a 5-7 membered heterocycloalkyl optionally substituted with one or more substituents selected from the group consisting of fluoro, —OH, —NH$_2$, lower alkyl, fluoro substituted lower alkyl, lower alkoxy, fluoro substituted lower alkoxy, lower alkylthio, and fluoro substituted lower alkylthio;

R$^{25}$ at each occurrence is independently selected from the group consisting of hydrogen, optionally substituted lower alkyl, optionally substituted cycloalkyl, optionally substituted heterocycloalkyl, optionally substituted aryl, and optionally substituted heteroaryl; and R$^{24}$ and R$^{26}$ at each occurrence are independently selected from the group consisting of hydrogen, provided, however, that hydrogen is not bound to any of S(O), S(O)$_2$, C(O) or C(S) of L or Li, optionally substituted lower alkyl, optionally substituted lower alkenyl, provided, however, that when R$^{24}$ or R$^{26}$ is optionally substituted lower alkenyl, no alkene carbon thereof is bound to N, S, O, S(O), S(O)$_2$, C(O) or C(S) of L or L1, optionally substituted lower alkynyl, provided, however, that when R$^{24}$ or R$^{26}$ is optionally substituted lower alkynyl, no alkyne carbon thereof is bound to N, S, O, S(O), S(O)$_2$, C(O) or C(S) of L or L1, optionally substituted cycloalkyl, optionally substituted heterocycloalkyl, optionally substituted aryl, and optionally substituted heteroaryl.

In a preferred embodiment, a compound of Formula (III) is provided wherein:
R$^2$ is H;
R$^3$ is -A-Ar-L1-R$^{24}$;
A is —C(O)—;
Ar is 2,4-difluorophenyl;
L1 is —SO$_2$—;
R$^4$ is H;
R$^5$ is 4-chlorophenyl;
R$^6$ is H;
R$^{24}$ is n-propyl (referred to herein as "PLX4032" "vemurafenib," or "Zelboraf") or a pharmaceutically acceptable salt thereof.

In other embodiments, one skilled in the art may generate or identify novel BRAF inhibitors using in vitro, in vivo, in silico, or other screening methods known in the art. For example, a BRAF inhibitor of wild type BRAF may be identified from a training set of small molecules, peptides, or nucleic acids using an assay for detecting phosphorylation of molecules which are downstream from BRAF in the MAPK signaling cascade (e.g., MEK and/or ERK). The BRAF inhibitor may act to suppress or inhibit BRAF expression and/or signaling function, thereby reducing phosphorylation of MEK and ERK. Several phosphorylation assays are available which could be used in such embodiments including, but not limited to, kinase activity assays (e.g., those sold by R&D Systems, Promega, Life Technologies); phospho-specific antibodies for use with immunoassays such as western blots, enzyme-linked immunosorbent assays (ELISA), flow cytometry, immunocytochemistry, immunohistochemistry; mass spectrometry, proteomics, and phospho-protein multiplex assays. In certain embodiments, BRAF inhibitors for use in the embodiments described herein may be identified using screening methods which measure candidate inhibitor ability to activate the MAPK pathway.

VEGF Inhibitor

In certain embodiments, the VEGF inhibitor is selected from aflibercept, pegaptanib, tivozanib, 3-(4-Bromo-2,6-difluoro-benzyloxy)-5-[3-(4-pyrrolidin-1-yl-butyl)-ureido]-isothiazole-4-carboxylic acid amide hydrochloride, axitinib, N-(4-bromo-2-fluorophenyl)-6-methoxy-7-[(1-methylpiperidin-4-yl-)methoxy]quinazolin-4-amine, an inhibitor of VEGF-R2 and VEGF-R1, axitinib, N,2-dimethyl-6-(2-(1-methyl-1H-imidazol-2-yhthieno[3,2-b]pyrid-in-7-yloxy) benzo[b]thiophene-3-carboxamide, tyrosine kinase inhibitor of the RET/PTC oncogenic kinase, N-(4-bromo-2-fluorophenyl)-6-methoxy-7-[(1-methylpiperidin-4-yl)methoxy] quinazolin-4-amine, pan-VEGF-R-kinase inhibitor; protein kinase inhibitor, multitargeted human epidermal receptor (HER) 1/2 and vascular endothelial growth factor receptor (VEGFR) 1/2 receptor family tyrosine kinases inhibitor, cediranib, sorafenib, vatalanib, glufanide disodium, VEGFR2-selective monoclonal antibody, angiozyme, an siRNA-based VEGFR1 inhibitor, 5-((7-Benzyloxyquinazolin-4-yl)amino)-4-fluoro-2-methyl phenol hydrochloride, any derivatives thereof and any combinations thereof.

In certain preferred embodiments, the VEGF inhibitor is a VEGF Receptor inhibitor, and even more preferably a VEGF Receptor kinase inhibitor such as Tivozanib (AV-951), AZD2932, Midostaurin (pkc412), BAW2881 (NVP-BAW2881), Nintedanib (BIBF 1120), SU5402, SU1498, BFH772, Sorafenib, Sunitinib, Dovitinib (TK1258), Semaxanib (SU5416), hypericin, vatalanib, ZM306416, AAL993, SU4312, DMXAA or Foretinib.

In certain embodiments, the VEGF Receptor inhibitor is a multi-tyrosine kinase inhibitor, such as afatinib, imatinib, dacomitinib, dasatinib, ponatinib, KD-019, bosutinib, lapatinib ditosylate, AZD9291, neratinib, poziotinib, S-222611, suramin hexasodium, AL-6802, BGB-102, PB357, Pyrotinib, sunitinib, sorafenib tosylate, pazopanib, regorafenib, apatinib, axitinib, carbozantinib, lenvatinib, nintedanib, vandetanib, tivozanib, anlotinib, midostaurin, muparfostat, BMS-690514, ENMD-2076, golvatinib, lucitanib, motesanib, necuparinib, RAF265, famitinib, telatinib, X82, ALNVSP, altiratinib, ABT348, MGCD516, OB318, ODM203, HHGV678, LY-3012207, CS2164, ilorasertib, radotinib, bafetinib, NRCAN-019, ABL001, metatinib tromethamine, rebastinib tosylate or VX-15.

TGF-Beta or TGF-Beta Receptor Inhibitor

TGF-β signaling is involved in many cellular functions, including cell growth, cell fate and apoptosis. Signaling typically begins with binding of a TGF-β superfamily ligand to a Type II receptor, which recruits and phosphorylates a Type I receptor. The Type 1 receptor then phosphorylates SMADs, which act as transcription factors in the nucleus and regulate target gene expression. Alternatively, TGF-β signaling can activate MAP kinase signaling pathways, for example, via p38 MAP kinase.

The TGF-β superfamily ligands comprise bone morphogenetic proteins (BMPs), growth and differentiation factors (GDFs), anti-Mullerian hormone (AMH), activin, nodal and TGF-βs.

A TGF-β inhibitor as used herein include an agent that reduces the activity of the TGF-β signaling pathway. There are many different ways of disrupting the TGF-β signaling pathway known in the art, any of which may be used in conjunction with the subject invention. For example, TGF-β signaling may be disrupted by: inhibition of TGF-β expression by a small-interfering RNA strategy; inhibition of furin (a TGF-β activating protease); inhibition of the pathway by physiological inhibitors, such as inhibition of BMP by Noggin, DAN or DAN-like proteins; neutralization of TGF-β with a monoclonal antibody; inhibition with small-molecule inhibitors of TGF-β receptor kinase 1 (also known as activin receptor-like kinase, ALK5), ALK4, ALK6, ALK7 or other TGF-β-related receptor kinases; inhibition of Smad 2 and Smad 3 signaling by overexpression of their physiological inhibitor, Smad 7, or by using thioredoxin as an Smad anchor disabling Smad from activation (Fuchs, Inhibition of TGF-β Signaling for the Treatment of Tumor Metastasis and Fibrotic Diseases. Current Signal Transduction Therapy 6(1):29-43(15), 2011).

For example, a TGF-β inhibitor may target a serine/threonine protein kinase selected from: TGF-β receptor kinase 1, ALK4, ALK5, ALK7, or p38. ALK4, ALK5 and ALK7 are all closely related receptors of the TGF-β superfamily. ALK4 has GI number 91; ALK5 (also known as TGF-β receptor kinase 1) has GI number 7046; and ALK7 has GI number 658. An inhibitor of any one of these kinases is one that effects a reduction in the enzymatic activity of any one (or more) of these kinases. Inhibition of ALK and p38 kinase has previously been shown to be linked in B-cell lymphoma (Bakkebo et al, "TGF-β-induced growth inhibition in B-cell lymphoma correlates with Smad 1/5 signaling and constitutively active p38MAPK," BMC Immunol. 11:57, 2010).

In certain embodiments, a TGF-β inhibitor may bind to and inhibit the activity of a Smad protein, such as R-SMAD or SMAD1-5 {i.e., SMAD1, SMAD2, SMAD3, SMAD4 or SMAD5).

In certain embodiments, a TGF-β inhibitor may bind to and reduces the activity of Ser/Thr protein kinase selected from: TGF-β receptor kinase 1, ALK4, ALK5, ALK7, or p38.

In certain embodiments, the medium of the invention comprises an inhibitor of ALK5.

In certain embodiments, the TGF-β inhibitor or TGF-β receptor inhibitor does not include a BMP antagonist {i.e., is an agent other than BMP antagonist).

Various methods for determining if a substance is a TGF-β inhibitor are known. For example, a cellular assay may be used in which cells are stably transfected with a reporter construct comprising the human PAI-1 promoter or Smad binding sites, driving a luciferase reporter gene. Inhibition of luciferase activity relative to control groups can be used as a measure of compound activity (De Gouville et al, Br. J. Pharmacol. 145(2): 166-177, 2005, incorporated herein by reference). Another example is the ALPHASCREEN® phosphosensor assay for measurement of kinase activity (Drew et al, J. Biomol. Screen. 16(2): 164-173, 2011, incorporated herein by reference).

A TGF-β inhibitor useful for the present invention may be a protein, a peptide, a small-molecule, a small-interfering RNA, an antisense oligonucleotide, an aptamer, an antibody or an antigen-binding portion thereof. The inhibitor may be naturally occurring or synthetic. Examples of small-molecule TGF-β inhibitors that can be used in the context of this invention include, but are not limited to, the small molecule inhibitors listed in Table 1 below:

TABLE 1

Small-molecule TGF-inhibitors targeting receptor kinases

| Inhibitor | Targets | IC$_{50}$ (nM) | Mol Wt | Name | Formula |
| --- | --- | --- | --- | --- | --- |
| A83-01 | ALK5 (TGF-β R1) | 12 | 421.52 | 3-(6-methyl-2-pyridinyl)-N-phenyl-4-(4-quinolinyl)-1H-pyrazole-1-carbothioamide | $C_{25}H_{19}N_5S$ |
|  | ALK4 | 45 |  |  |  |
|  | ALK7 | 7.5 |  |  |  |
| SB-431542 | ALK5 | 94 | 384.39 | 4-[4-(1,3-benzodioxol-5-yl)-5-(2-pyridinyl)-1H-imidazol-2-yl]benzamide | $C_{22}H_{16}N_4O_3$ |
|  | ALK4 |  |  |  |  |
|  | ALK7 |  |  |  |  |

TABLE 1-continued

Small-molecule TGF-inhibitors targeting receptor kinases

| Inhibitor | Targets | IC$_{50}$ (nM) | Mol Wt | Name | Formula |
|---|---|---|---|---|---|
| SB-505124 | ALK5 | 47 | 335.4 | 2-(5-benzo[1,3]dioxol-5-yl-2-tert-butyl-3H-imidazol-4-yl)-6-methylpyridine hydrochloride hydrate | $C_{20}H_{21}N_3O_2$ |
|  | ALK4 | 129 |  |  |  |
| SB-525334 | ALK5 | 14.3 | 343.42 | 6-[2-(1,1-dimethylethyl)-5-(6-methyl-2-pyridinyl)-1H-imidazol-4-yl]quinoxaline | $C_{21}H_{21}N_5$ |
| SD-208 | ALK5 | 49 | 352.75 | 2-(5-chloro-2-fluorophenyl)-4-[(4-pyridyl)amino]pteridine | $C_{17}H_{10}ClFN_6$ |
| LY-36494 | TGR-β RI | 59 | 272.31 | 4-[3-(2-pyridinyl)-1H-pyrazol-4-yl]-quinoline | $C_{17}H_{12}N_4$ |
|  | TGF-β RII | 400 |  |  |  |
|  | MLK-7K | 1400 |  |  |  |
| SJN-2511 | ALK5 | 23 | 287.32 | 2-(3-(6-methylpyridin-2-yl)-1H-pyrazol-4-yl)-1,5-naphthyridine | $C_{17}H_{13}N_5$ |

One or more of any of the inhibitors listed in Table 1 above, or a combination thereof, may be used as a TGF-β inhibitor in the subject invention. In certain embodiments, the combination may include: SB-525334 and SD-208 and A83-01; SD-208 and A83-01; or SD-208 and A83-01.

One of skill in the art will appreciate that a number of other small-molecule inhibitors exist that are primarily designed to target other kinases, but at high concentrations may also inhibit TGF-β receptor kinases. For example, SB-203580 is a p38 MAP kinase inhibitor that, at high concentrations (for example, approximate 10 µM or more) may inhibit ALK5. Any such inhibitor that inhibits the TGF-β signaling pathway may also be used in this invention. In certain embodiments, A83-01 may be added to the culture medium at a concentration of between 10 nM and 10 µM, or between 20 nM and 5 µM, or between 50 nM and 1 µM. In certain embodiments, A83-01 may be added to the medium at about 500 nM. In certain embodiments, A83-01 may be added to the culture medium at a concentration of between 350-650 nM, 450-550 nM, or about 500 nM. In certain embodiments, A83-01 may be added to the culture medium at a concentration of between 25-75 nM, 40-60 nM, or about 50 nM.

SB-431542 may be added to the culture medium at a concentration of between 80 nM and 80 µM, or between 100 nM and 40 µM, or between 500 nM and 10 µM, or between 1-5 µM. For example, SB-431542 may be added to the culture medium at about 2 µM.

SB-505124 may be added to the culture medium at a concentration of between 40 nM and 40 µM, or between 80 nM and 20 µM, or between 200 nM and 1 µM. For example, SB-505124 may be added to the culture medium at about 500 nM.

SB-525334 may be added to the culture medium at a concentration of between 10 nM and 10 µM, or between 20 nM and 5 µM, or between 50 nM and 1 µM. For example, SB-525334 may be added to the culture medium at about 100 nM.

LY 364947 may be added to the culture medium at a concentration of between 40 nM and 40 µM, or between 80 nM and 20 µM, or between 200 nM and 1 µM. For example, LY 364947 may be added to the culture medium at about 500 nM.

SD-208 may be added to the culture medium at a concentration of between 40 nM and 40 µM, or between 80 nM and 20 µM, or between 200 nM and 1 µM. For example, SD-208 may be added to the culture medium at abut 500 nM.

S JN 2511 may be added to the culture medium at a concentration of between 20 nM and 20 µM, or between 40 nM and 10 µM, or between 100 nM and 1 µM. For example, A83-01 may be added to the culture medium at approximately 200 nM.

p38 Inhibitor

A "p38 inhibitor" may include an inhibitor that, directly or indirectly, negatively regulates p38 signaling, such as an agent that binds to and reduces the activity of at least one p38 isoform. p38 protein kinases (see, GI number 1432) are part of the family of mitogen-activated protein kinases (MAPKs). MAPKs are serine/threonine-specific protein kinases that respond to extracellular stimuli, such as environmental stress and inflammatory cytokines, and regulate various cellular activities, such as gene expression, differentiation, mitosis, proliferation, and cell survival/apoptosis. The p38 MAPKs exist as α, β, β32, γ and δ isoforms.

Various methods for determining if a substance is a p38 inhibitor are known, such as: phospho-specific antibody detection of phosphorylation at Thr180/Tyr182, which provides a well-established measure of cellular p38 activation or inhibition; biochemical recombinant kinase assays; tumor necrosis factor alpha (TNFa) secretion assays; and DiscoverRx high throughput screening platform for p38 inhibitors. Several p38 activity assay kits also exist (e.g. Millipore, Sigma-Aldrich).

In certain embodiments, high concentrations (e.g., more than 100 nM, or more than 1 µM, more than 10 µM, or more than 100 µM) of a p38 inhibitor may have the effect of inhibiting TGF-β. In other embodiments, the p38 inhibitor does not inhibit TGF-β signaling.

Various p38 inhibitors are known in the art (for example, see Table 1). In some embodiments, the inhibitor that directly or indirectly negatively regulates p38 signaling is selected from the group consisting of SB-202190, SB-203580, VX-702, VX-745, PD-169316, RO-4402257 and BIRB-796.

In certain embodiments, the medium comprises both: a) an inhibitor that binds to and reduces the activity of any one or more of the kinases from the group consisting of: ALK4, ALK5 and ALK7; and b) an inhibitor that binds to and reduces the activity of p38.

In certain embodiments, the medium comprises an inhibitor that binds to and reduces the activity of ALK5 and an inhibitor that binds to and reduces the activity of p38.

In one embodiment, the inhibitor binds to and reduces the activity of its target (for example, TGF-β and/or p38) by more than 10%; more than 30%; more than 60%; more than 80%; more than 90%; more than 95%; or more than 99% compared to a control, as assessed by a cellular assay. Examples of cellular assays for measuring target inhibition are well known in the art as described above.

An inhibitor of TGF-β and/or p38 may have an IC50 value equal to or less than 2000 nM; less than 1000 nM; less than 100 nM; less than 50 nM; less than 30 nM; less than 20 nM or less than 10 mM. The IC50 value refers to the effectiveness of an inhibitor in inhibiting its target's biological or biochemical function. The IC50 indicates how much of a particular inhibitor is required to inhibit a kinase by 50%. IC50 values can be calculated in accordance with the assay methods set out above. An inhibitor of TGF-β and/or p38 may exist in various forms, including natural or modified substrates, enzymes, receptors, small organic molecules, such as small natural or synthetic organic molecules of up to 2000 Da, preferably 800 Da or less, peptidomimetics, inorganic molecules, peptides, polypeptides, antisense oligonucleotides aptamers, and structural or functional mimetics of these including small molecules.

In certain embodiments, the inhibitor of TGF-β and/or p38 may also be an aptamer. As used herein, the term "aptamer" refers to strands of oligonucleotides (DNA or RNA) that can adopt highly specific three-dimensional conformations. Aptamers are designed to have high binding affinities and specificities towards certain target molecules, including extracellular and intracellular proteins. Aptamers may be produced using, for example, Systematic Evolution of Ligands by Exponential Enrichment (SELEX) process (see, for example, Tuerk and Gold, Systematic evolution of ligands by exponential enrichment: RNA ligands to bacteriophage T4 DNA Polymerase. Science 249:505-510, 1990, incorporated herein by reference).

In certain embodiments, the TGF-β and/or p38 inhibitor may be a small synthetic molecule with a molecular weight of between 50 and 800 Da, between 80 and 700 Da, between 100 and 600 Da, or between 150 and 500 Da.

In certain embodiments, the TGF-β and/or p38 inhibitor comprises a pyridinylimidazole or a 2,4-disubstituted teridine or a quinazoline, for example comprises:

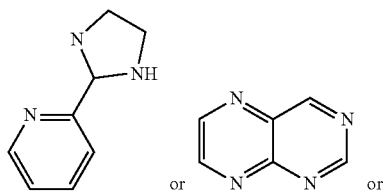 or

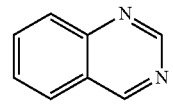 or

-continued

Particular examples of TGF-β and/or p38 inhibitors that may be used in accordance with the invention include, but are not limited to: SB-202190, SB-203580, SB-206718, SB-227931, VX-702, VX-745, PD-169316, RO-4402257, BIRB-796, A83-01 SB-431542, SB-505124, SB-525334, LY 364947, SD-208, SJ 2511 (see Table 2).

For example, SB-202190 may be added to the culture medium at a concentration of between 50 nM and 100 μM, or between 100 nM and 50 μM, or between 1 μM and 50 μM. For example, SB-202190 may be added to the culture medium at approximately 10 μM.

SB-203580 may be added to the culture medium at a concentration of between 50 nM and 100 μM, or between 100 nM and 50 μM, or between 1 μM and 50 μM. For example, SB-203580 may be added to the culture medium at approximately 10 μM.

VX-702 may be added to the culture medium at a concentration of between 50 nM and 100 μM, or between 100 nM and 50 μM, or between 1 μM and 25 μM. For example, VX-702 may be added to the culture medium at approximately 5 μM.

VX-745 may be added to the culture medium at a concentration of between 10 nM and 50 μM, or between 50 nM and 50 μM, or between 250 nM and 10 μM. For example, VX-745 may be added to the culture medium at approximately 1 μM.

PD-169316 may be added to the culture medium at a concentration of between 100 nM and 200 μM, or between 200 nM and 100 μM, or between 1 μM and 50 μM. For example, PD-169316 may be added to the culture medium at approximately 20 μM.

RO-4402257 may be added to the culture medium at a concentration of between 10 nM and 50 μM, or between 50 nM and 50 μM, or between 500 nM and 10 μM. For example, RO-4402257 may be added to the culture medium at approximately 1 μM.

BIRB-796 may be added to the culture medium at a concentration of between 10 nM and 50 μM, or between 50 nM and 50 μM, or between 500 nM and 10 μM. For example, BIRB-796 may be added to the culture medium at approximately 1 μM.

See Table 1 and associated text above for the applicable concentrations for the other factors in Table 2.

TABLE 2

Exemplary TGF-β and/or p38 Inhibitors

| Inhibitor | Targets | IC$_{50}$ (nM) | Mol Wt | Name | Formula |
| --- | --- | --- | --- | --- | --- |
| A83-01 | ALK5 (TGF-βRI) | 12 | 421.52 | 3-(6-methyl-2-pyridinyl)-N-phenyl-4-(4-quinolinyl)-1H-pyrazole-1-carbothioamide | $C_{25}H_{19}N_5S$ |
|  | ALK4 | 45 |  |  |  |
|  | ALK7 | 7.5 |  |  |  |

TABLE 2-continued

Exemplary TGF-β and/or p38 Inhibitors

| Inhibitor | Targets | IC$_{50}$ (nM) | Mol Wt | Name | Formula |
|---|---|---|---|---|---|
| SB-431542 | ALK5 ALK4 ALK7 | 94 | 384.39 | 4-[4-(1,3-benzodioxol-5-yl)-5-(2-pyridinyl)-1H-imidazol-2-yl]benzamide | $C_{22}H_{16}N_4O_3$ |
| SB-505124 | ALK5 ALK4 | 47 129 | 335.4 | 2-(5-benzo[1,3]dioxol-5-yl-2-tert-butyl-3H-imidazol-4-yl)-6-methylpyridine hydrochloride hydrate | $C_{20}H_{21}N_3O_2$ |
| SB-525334 | ALK5 | 14.3 | 343.42 | 6-[2-(1,1-dimethylethyl)-5-(6-methyl-2-pyridinyl-1H-imidazol-4-yl]quinoxaline | $C_{21}H_{21}N_5$ |
| SD-208 | ALK5 | 49 | 352.75 | 2-(5-chloro-2-fluorophenyl)-4-[(4-pyridyl)amino]pteridine | $C_{17}H_{10}ClFN_6$ |
| LY-36494 | TGR-βRI TGF-βRII MLK-7K | 59 400 1400 | 272.31 | 4-[3-(2-pyridinyl)-1H-pyrazol-4-yl]-quinoline | $C_{17}H_{12}N_4$ |
| LY-364947 | ALK5 | 59 | 272.30 | 4-[3-(2-pyridinyl)-1H-pyrazol-4-yl]quinoline | $C_{17}H_{12}N_4$ |
| SJN-2511 | ALK5 | 23 | 287.32 | 2-(3-(6-methylpyridin-2-yl)-1H-pyrazol-4-yl)-1,5-naphthyridine | $C_{17}H_{13}N_5$ |
| SB-202190 | p38 MAP kinase p38α p38β | 38 50 100 | 331.35 | 4-[4-(4-fluorophenyl)-5-(4-pyridinyl)-1H-imidazol-2-yl]phenol | $C_{20}H_{14}N_3OF$ |
| SB-203580 | p38 p38β2 | 50 500 | 377.44 | 4-[5-(4-fluorophenyl)-2-[4-(methylsulfonyl)phenyl]-1H-imidazol-4-yl]pyridine | $C_{21}H_{16}FN_3OS$ |
| VX-702 | p38α p38β | 4-20; $K_d$ = 23.7 $K_d$ = 17 | 404.32 | 6-[(aminocarbonyl)(2,6-difluorophenyl)amino]-2-(2,4-difluorophenyl)-3-pyridinecarboxamide | $C_{19}H_{12}F_4N_4O_2$ |
| VX-745 | p38α | 10 | 436.26 | 5-(2,6-dichlorophenyl)-2-[2,4-difluorophenyl)thio]-6H-pyrimido[1,6-b]pyridazin-6-one | $C_{19}H_9Cl_2F_2N_3OS$ |
| PD-169316 | p38 | 89 | 360.3 | 4-[5-(4-fluorophenyl)-2-(4-nitrophenyl)-1H-imidazol-4-yl]-pyridine | $C_{20}H_{13}FN_4O$ |
| RO-4402257 | p38α p38β | 14 480 | | pyrido[2,3-d]pyrimidin-7(8H)-one,6-(2,4-difluorophenoxy)-2-[[3-hydroxy-1-(2-hydroxyethyl)propyl]amino]-8-methyl] | |
| BIRB-796 | p38 | 4 | 527.67 | 1-[2-(4-methylphenyl)-5-tert-butyl-pyrazol-3-yl]-3-[4-(2-morpholin-4-ylethoxy)naphthalen-1-yl]urea::3-[2-(4-methylphenyl)-5-tert-butyl-pyrazol-3-yl]-1-[4-(2-morpholin-4-ylethoxy)naphthalen-1-yl]urea::3-[3-tert-butyl-1-(4-methylphenyl)-1H-pyrazol-5-yl]-1-{4-[2-(morpholin-4-yl)ethoxy]naphthalen-1-yl}urea | $C_{31}H_{37}N_5O_3$ |

Thus, in some embodiments, the inhibitor that directly or indirectly, negatively regulates TGF-β and/or p38 signaling is added to the culture medium at a concentration of between 1 nM and 100 μM, between 10 nM and 100 μM, between 100 nM and 10 μM, or about 1 μM. For example, wherein the total concentration of the one or more inhibitor is between 10 nM and 100 μM, between 100 nM and 10 μM, or about 1 μM.

Oct4-Activating Agent

An Oct4-activating agent is an agent that can activate Oct4 promoter-driven reporter genes, such as a luciferase gene under the transcriptional control of an Oct4-promoter, and more preferably is an able to activate both Oct4 and Nanog promoter-driven reporter genes. Furthermore, when added to the reprogramming mixture along with the quartet reprogramming factors (Oct4, Sox2, c-Myc, and Klf4), an Oct4-activating agent enhances the iPSC reprogramming efficiency and accelerated the reprogramming process. Exemplary Oct4-activating Agents are taught in, for example, US Patent Application 20150191701 and Li et al.

(2012) "Identification of Oct4-activating compounds that enhance reprogramming efficiency". PNAS 109(51):20853-8.

In certain embodiments, the Oct4-activating agent is represented in formula

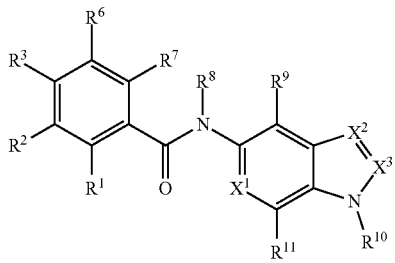

wherein, $X^1$ is $C(R^{12})$ or N;
$X^2$ is $C(R^4)$ or N;
$X^3$ is $C(R^5)$ or N;
$R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, wherein $R^2$ and $R^3$ are optionally joined to form a substituted or unsubstituted heterocycloalkyl or substituted or unsubstituted heteroaryl.

In certain preferred embodiments, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, substituted or unsubstituted alkyl, substituted or unsubstituted heteroalkyl, or substituted or unsubstituted heterocycloalkyl.

In certain preferred embodiments, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, substituted or unsubstituted alkyl, or substituted or unsubstituted heteroalkyl.

In certain preferred embodiments, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, substituted or unsubstituted $C_1$ to $C_{10}$ alkyl, substituted or unsubstituted 2 to 10 membered heteroalkyl or substituted or unsubstituted 3 to 8 membered heterocycloalkyl.

In certain preferred embodiments, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, substituted or unsubstituted $C_1$ to $C_{10}$ alkyl or substituted or unsubstituted 2 to 10 membered heteroalkyl.

In certain preferred embodiments, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, unsubstituted alkyl, unsubstituted heteroalkyl, or substituted heterocycloalkyl.

In certain preferred embodiments, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, unsubstituted alkyl or unsubstituted heteroalkyl.

In certain preferred embodiments, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, unsubstituted $C_1$ to $C_{10}$ alkyl, unsubstituted 2 to 10 membered heteroalkyl, or substituted 3 to 8 membered heterocycloalkyl.

In certain preferred embodiments, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, unsubstituted $C_1$ to $C_{10}$ alkyl or unsubstituted 2 to 10 membered heteroalkyl.

In certain preferred embodiments, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, unsubstituted $C_1$ to $C_{10}$ alkyl or unsubstituted 2 to 10 membered heteroalkyl.

In certain preferred embodiments, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —N(CH$_3$)$_2$, unsubstituted $C_1$ to $C_5$ alkyl or unsubstituted $C_1$ to $C_5$ alkoxy.

In certain preferred embodiments, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —N(CH$_3$)$_2$, unsubstituted $C_1$ to $C_5$ alkyl, methoxy, ethoxy or propoxy.

In certain embodiments, the Oct4-activating agent is selected from the group consisting of

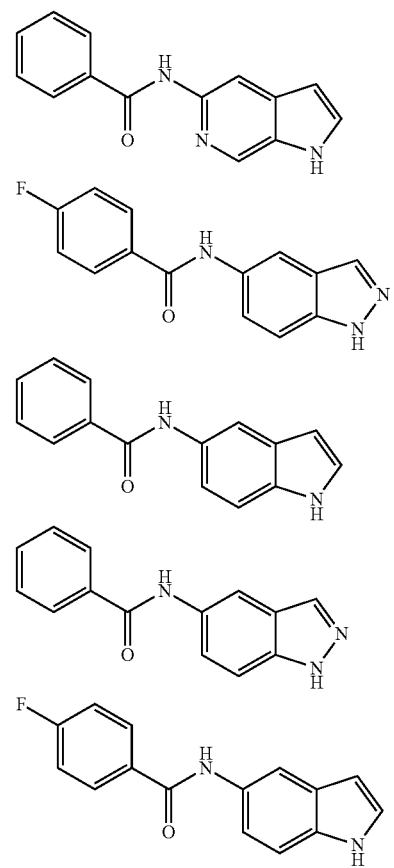

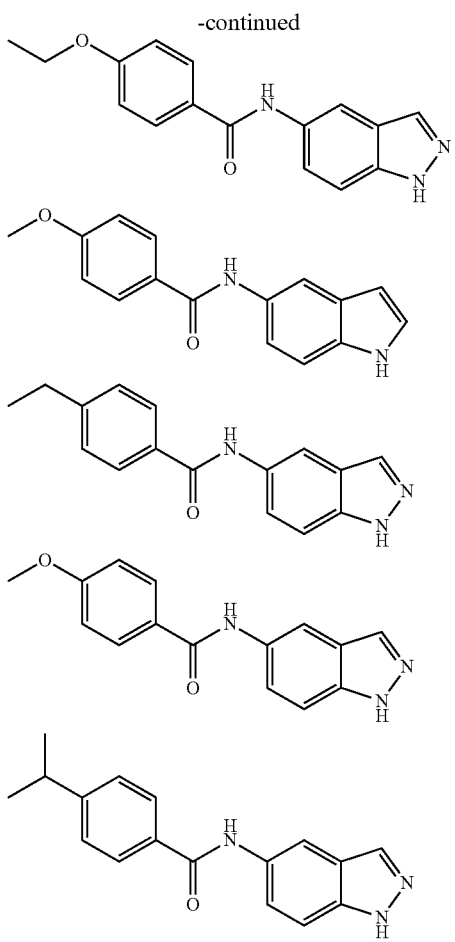

In certain embodiments, the Oct4-activating agent is OAC1, having the structure

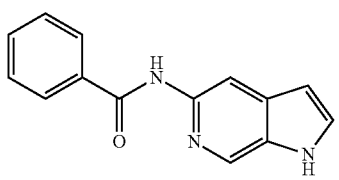 [SMILES: O=C(Nc1cc2cc[nH]c2cn1)c1ccccc1]

PDGFRα/β Inhibitor

In certain embodiments, the medium includes a PDGFR inhibitor, preferably a PDGFRα/β inhibitor.

An exemplary PDGFRα/β inhibitor is GZD856 (Zhang et al. Cancer Lett. 2016 May 28; 375(1):172-178)

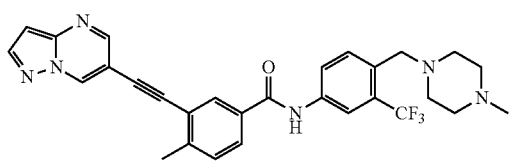 [SMILES: Cc1ccc(C(=O)Nc2ccc(CN3CCN(C)CC3)c(C(F)(F)F)c2)cc1C#Cc1cnc2ccnn2c1]

In certain embodiments, the PDGFRα/β inhibitor is a potent inhibitor having a IC50 of 250 nM or less and more preferably 100 nM or less (in cell-free assays), and may be selected from Sunitinib Malate, Ponatinib (AP24534), Telatinib, Amuvatinib (MP-470), Ki8751, Regorafenib, Crenolanib (CP-868596), CP-673451, Axitinib, and Nintedanib (BIBF 1120).

In certain embodiments, the PDGFRα/β inhibitor is a potent and selective inhibitor of PDGFRα/β with IC50 of 250 nM or less and more preferably 100 nM (in cell-free assays), and exhibits greater than 100-fold selectivity over other angiogenic receptors, and more preferably greater than 200, 300 or even 400-fold selectivity over other angiogenic receptors. An exemplary selective inhibitor of PDGFRα/β is CP-673451

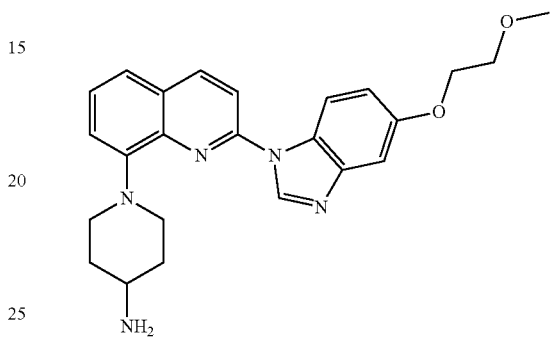

JNK Inhibitor

In certain embodiments, the culture medium includes a JNK Inhibitor. The mitogen activated kinases JNK1/2/3 are key enzymes in signaling modules that transduce and integrate extracellular stimuli into coordinated cellular response. In certain embodiments, the JNK Inhibitor inhibitors JNK kinases (i.e., inhibits phosphorylation of c-Jun, a direct substrate of JNK kinase, in cells exposed to the inhibitor, with an IC50 of 250 nM or less and more preferably 100 nM.

In certain embodiments, the at least one apoptosis inhibitor is a JNK inhibitor. Any JNK inhibitor is contemplated for use in the formulations, compositions, methods of the present invention. JNK inhibitors are generally known to those skilled in the art (e.g., see U.S. Pat. Nos. 6,949,544; 7,129, 242; 7,326,418, 8,143,271 and 8,530,480).

In certain embodiments, the JNK Inhibitor is a selective JNK inhibitor that inhibits phosphorylation of c-Jun preferably in a manner that depends on covalent modification of the conserved cysteine residue in the JNK kinase.

In certain embodiments, the JNK Inhibitor is JNK-IN-5, JNK-IN-6, JNK-IN-7, JNK-IN-8, JNK-IN-9, JNK-IN-10, JNK-IN-11, JNK-IN-12, SP-600125, or AS601245.

Exemplary JNK inhibitors include, but are not limited to, SP600125 (anthra[1-9-cd]pyrazol-6(2H)-one), JNK-IN-8 (3-[[4-(dimethylamino)-1-oxo-2-buten-1-yl]amino]-N-[3-methyl-4-[[4-(3-pyridinyl)-2-pyrimidinyl]amino]phenyl]-benzamide); and JNK-Inhibitor IX (N-(3-cyano-4,5,6,7-tetrahydrobenzo[b]thien-2-yl)-1-naphthalenecarboxamide).

Notch Agonist

The culture medium of the invention may additionally include a Notch agonist. Notch signaling has been shown to play an important role in cell-fate determination, as well as in cell survival and proliferation. Notch receptor proteins can interact with a number of surface-bound or secreted ligands, including but not limited to Jagged-1, Jagged-2, Delta-1 or Delta-like 1, Delta-like 3, Delta-like 4, etc. Upon ligand binding, Notch receptors are activated by serial cleavage events involving members of the ADAM protease family, as well as an intramembranous cleavage regulated by the gamma secretase presinilin. The result is a translocation of the intracellular domain of Notch to the nucleus, where it transcriptionally activates downstream genes.

A "Notch agonist" as used herein includes a molecule that stimulates a Notch activity in a cell by at least about 10%, at least about 20%, at least about 30%, at least about 50%, at least about 70%, at least about 90%, at least about 100%, at least about 3-fold, 5-fold, 10-fold, 20-fold, 50-fold, 100-fold, 200-fold, 500-fold, 1000-fold or more, relative to a level of a Notch activity in the absence of the Notch agonist. As is known in the art, Notch activity can be determined by, for example, measuring the transcriptional activity of Notch, by a 4xwtCBF1-luciferase reporter construct described by Hsieh et al. (Mol. Cell. Biol. 16:952-959, 1996, incorporated herein by reference).

In certain embodiments, the Notch agonist is selected from: Jagged-1, Delta-1 and Delta-like 4, or an active fragment or derivative thereof. In certain embodiments, the Notch agonist is DSL peptide (Dontu et al., Breast Cancer Res., 6:R605-R615, 2004), having the amino acid sequence CDDYYYGFGCNKFCRPR (SEQ ID NO: 36). The DSL peptide (ANA spec) may be used at a concentration between 10 μM and 100 nM, or at least 10 μM and not higher than 100 nM. In certain embodiments, the final concentration of Jagged-1 is about 0.1-10 μM; or about 0.2-5 μM; or about 0.5-2 μM; or about 1 μM.

In certain embodiments, any of the specific Notch agonist referenced herein, such as Jagged-1, Jagged-2, Delta-1 and Delta-like 4 may be replaced by a natural, synthetic, or recombinantly produced homologs or fragments thereof that retain at least about 80%, 85%, 90%, 95%, 99% of the respective Notch agonist activity, and/or homologs or fragments thereof that share at least about 60%, 70%, 80%, 90%, 95%, 97%, 99% amino acid sequence identity as measured by any art recognized sequence alignment software based on either a global alignment technique (e.g., the Needleman-Wunsch algorithm) or a local alignment technique (e.g., the Smith-Waterman algorithm).

The sequences of the representative Notch agonists referenced herein are represented in SEQ ID NOs. 28-35.

The Notch agonist may be added to the culture medium every 1, 2, 3, or 4 days during the first 1-2 weeks of culturing the stem cells.

Nicotinamide

The culture medium of the invention may additionally be supplemented with nicotinamide or its analogs, precursors, or mimics, such as methyl-nicotinamid, benazamid, pyrazinamide, thymine, or niacin. Nicotinamide may be added to the culture medium to a final concentration of between 1 and 100 mM, between 5 and 50 mM, or preferably between 5 and 20 mM. For example, nicotinamide may be added to the culture medium to a final concentration of approximately 10 mM. The similar concentrations of nicotinamide analogs, precursors, or mimics can also be used alone or in combination.

Extracellular Matrix (ECM)

Extracellular matrix (ECM), used interchangeably herein with "basement membrane matrix," is secreted by connective tissue cells, and comprises a variety of polysaccharides, water, elastin, and proteins that may comprise proteoglycans, collagen, entactin (nidogen), fibronectin, fibrinogen, fibrillin, laminin, and hyaluronic acid. ECM may provide the suitable substrate and microenvironment conductive for selecting and culturing the subject stem cells.

In certain embodiments, the subject stem cells are attached to or in contact with an ECM. Different types of ECM are known in the art, and may comprise different compositions including different types of proteoglycans and/or different combination of proteoglycans. The ECM may be provided by culturing ECM-producing cells, such as certain fibroblast cells. Examples of extracellular matrix-producing cells include chondrocytes that mainly produce collagen and proteoglycans; fibroblast cells that mainly produce type IV collagen, laminin, interstitial procollagens, and fibronectin; and colonic myofibroblasts that mainly produce collagens (type I, III, and V), chondroitin sulfate proteoglycan, hyaluronic acid, fibronectin, and tenascin-C.

In certain embodiments, at least some ECM is produced by the murine 3T3-J2 clone, which may be grown on top of the MATRIGEL™ basement membrane matrix (BD Biosciences) as feeder cell layer.

Alternatively, the ECM may be commercially provided. Examples of commercially available extracellular matrices are extracellular matrix proteins (Invitrogen) and MATRIGEL™ basement membrane matrix (BD Biosciences). The use of an ECM for culturing stem cells may enhance long-term survival of the stem cells and/or the continued presence of undifferentiated stem cells. An alternative may be a fibrin substrate or fibrin gel—or a scaffold, such as glycerolized allografts that are depleted from the original cells.

In certain embodiments, the ECM for use in a method of the invention comprises at least two distinct glycoproteins, such as two different types of collagen or a collagen and laminin. The ECM may be a synthetic hydrogel extracellular matrix, or a naturally occurring ECM. In certain embodiments, the ECM is provided by MATRIGEL™ basement membrane matrix (BD Biosciences), which comprises laminin, entactin, and collagen IV.

Medium

A cell culture medium that is used in a method of the invention may comprise any cell culture medium, such as culture medium buffered at about pH 7.4 (e.g., between about pH 7.2-7.6) with a carbonate-based buffer. Many commercially available tissue culture media are potentially suitable for the methods of the invention, including, but are not limited to, Dulbecco's Modified Eagle Media (DMEM, e.g., DMEM without L-glutamine but with high glucose), Minimal Essential Medium (MEM), Knockout-DMEM (KO-DMEM), Glasgow Minimal Essential Medium (G-MEM), Basal Medium Eagle (BME), DMEM/Ham's F12, Advanced DMEM/Ham's F12, Iscove's Modified Dulbecco's Media and Minimal Essential Media (MEM), Ham's F-10, Ham's F-12, Medium 199, and RPMI 1640 Media.

The cells may be cultured in an atmosphere comprising between 5-10% $CO_2$ (e.g., at least about 5% but no more than 10% $CO_2$, or about 5% $CO_2$). In certain embodiments, the cell culture medium is DMEM/F12 (e.g., 3:1 mixture) or RPMI 1640, supplemented with L-glutamine, insulin, Penicillin/streptomycin, and/or transferrin. In certain embodiments, Advanced DMEM/F12 or Advanced RPMI is used, which is optimized for serum free culture and already includes insulin. The Advanced DMEM/F12 or Advanced RPMI medium may be further supplemented with L-glutamine and Penicillin/streptomycin. In certain embodiments, the cell culture medium is supplemented with one or more a purified, natural, semi-synthetic, and/or synthetic factors described herein. In certain embodiments, the cell culture medium is supplemented by about 10% fetal bovine serum (FBS) that is not heat inactivated prior to use. Additional supplements, such as, for example, B-27® Serum Free Supplement (Invitrogen), N-Acetylcysteine (Sigma) and/or N2 serum free supplement (Invitrogen), or Neurobasal (Gibco), TeSR (StemGent) may also be added to the medium.

In certain embodiments, the medium may contain one or more antibiotics to prevent contamination (such as Penicillin/streptomycin). In certain embodiments, the medium may have an endotoxin content of less than 0.1 endotoxin units per mL, or may have an endotoxin content less than 0.05 endotoxin units per mL. Methods for determining the endotoxin content of culture media are known in the art.

A cell culture medium according to the invention allows the survival and/or proliferation and/or differentiation of epithelial stem cells on an extracellular matrix. The term "cell culture medium" as used herein is synonymous with "medium," "culture medium," or "cell medium."

The modified (growth) medium of the invention comprises, in a base medium, (a) a ROCK (Rho Kinase) inhibitor; (b) a Wnt agonist; (c) a mitogenic growth factor; (d) a TGF-beta signaling pathway inhibitor, such as TGF-beta inhibitor, or a TGF-beta receptor inhibitor); and (e) insulin or IGF; and the medium optionally further comprising a Bone Morphogenetic Protein (BMP) antagonist.

Thus in one aspect, the invention provides a base medium (Base Medium) comprising: insulin or an insulin-like growth factor; T3 (3,3',5-Triiodo-L-Thyronine); hydrocortisone; adenine; EGF; and 10% fetal bovine serum (without heat inactivation), in DMEM:F12 3:1 medium supplemented with L-glutamine.

In certain embodiments, the Base Medium comprises about: 5 µg/mL insulin; 2×10"9 M T3 (3,3',5-Triiodo-L-Thyronine); 400 ng/mL hydrocortisone; 24.3 µg/mL adenine; 10 ng/mL EGF; and 10% fetal bovine serum (without heat inactivation), in DMEM:F12 3: 1 medium supplemented with 1.35 mM L-glutamine.

In certain embodiments, the concentration for each of the medium components referenced in the immediate preceding paragraph is independently 2%, 5%, 10%, 15%, 20%, 25%, 30%, 35%, 40%, 45%, 50%, 60%, 70%, 80%, 90%, 95% higher or lower than the respective recited value, or 2-fold, 3-fold, 5-fold, 10-fold, 20-fold higher than the respective recited value. For example, in an illustrative medium, insulin concentration may be 6 µg/mL (20% higher than the recited 5 µg/mL), EGF concentration may be 5 ng/mL (50% lower than the recited 10 ng/mL), while the remaining components each has the same concentration recited above.

In a related aspect, the invention provides a base medium containing cholera enterotoxin. In other embodiments, the base medium does not contain cholera enterotoxin.

The Base Medium may further comprise one or more antibiotics, such as Pen/Strep, and/or gentamicin.

The base media may be used to produce Modified Growth Medium (or simply Modified Medium) by adding one or more of the factors above.

4. Protein Sequences of the Representative Medium Factors

Several representative (non-limiting) protein factors used in the media and methods of the invention are provided below. For each listed factor, numerous homologs or functional equivalents are known in the art, and can be readily retrieved from public databases such as GenBank, EMBL, and/or NCBI RefSeq, just to name a few. Additional proteins or peptide fragments thereof, or polynucleotides encoding the same, including functional homologs from human or non-human mammals, can be readily retrieved from public sources through, for example, sequence-based searches such as NCBI BLASTp or BLASTn or both.

```
BMP inhibitors
Noggin: (GenBank: AAA83259.1), Homo sapiens:
                                                      (SEQ ID NO: 1)
MERCPSLGVT LYALVVVLGL RATPAGGQHY LHIRPAPSDN LPLVDLIEHP DPIFDPKEKD

LNETLLRSLL GGHYDPGFMA TSPPEDRPGG GGGAAGGAED LAELDQLLRQ RPSGAMPSEI

KGLEFSEGLA QGKKQRLSKK LRRKLQMWLW SQTFCPVLYA WNDLGSRFWP RYVKVGSCFS

KRSCSVPEGM VCKPSKSVHL TVLRWRCQRR GGQRCGWIPI QYPIISECKC SC

Chordin (GenBank: AAG35767.1), Homo sapiens:
                                                      (SEQ ID NO 2)
MPSLPAPPAP LLLLGLLLLG SRPARGAGPE PPVLPIRSEK EPLPVRGAAG CTFGGKVYAL

DETWHPDLGE PFGVMRCVLC ACEAPQWGRR TRGPGRVSCK NIKPECPTPA CGQPRQLPGH

CCQTCPQERS SSERQPSGLS FEYPRDPEHR SYSDRGEPGA EERARGDGHT DFVALLTGPR

SQAVARARVS LLRSSLRFSI SYRRLDRPTR IRFSDSNGSV LFEHPAAPTQ DGLVCGVWRA

VPRLSLRLLR AEQLHVALVT LTHPSGEVWG PLIRHRALAA ETFSAILTLE GPPQQGVGGI

TLLTLSDTED SLHFLLLFRG LLEPRSGGLT QVPLRLQILH QGQLLRELQA NVSAQEPGFA

EVLPNLTVQE MDWLVLGELQ MALEWAGRPG LRISGHIAAR KSCDVLQSVL CGADALIPVQ

TGAAGSASLT LLGNGSLIYQ VQVVGTSSEV VAMTLETKPQ RRDQRTVLCH MAGLQPGGHT

AVGICPGLGA RGAHMLLQNE LFLNVGTKDF PDGELRGHVA ALPYCGHSAR HDTLPVPLAG

ALVLPPVKSQ AAGHAWLSLD THCHLHYEVL LAGLGGSEQG TVTAHLLGPP GTPGPRRLLK

GFYGSEAQGV VKDLEPELLR HLAKGMASLL ITTKGSPRGE LRGQVHIANQ CEVGGLRLEA

AGAEGVRALG APDTASAAPP VVPGLPALAP AKPGGPGRPR DPNTCFFEGQ QRPHGARWAP

NYDPLCSLCT CQRRTVICDP VVCPPPSCPH PVQAPDQCCP VCPEKQDVRD LPGLPRSRDP
```

-continued

GEGCYFDGDR SWRAAGTRWH PVVPPFGLIK CAVCTCKGGT GEVHCEKVQC PRLACAQPVR

VNPTDCCKQC PVGSGAHPQL GDPMQADGPR GCRFAGQWFP ESQSWHPSVP PFGEMSCITC

RCGAGVPHCE RDDCSLPLSC GSGKESRCCS RCTAHRRPAP ETRTDPELEK EAEGS

Follistatin (GenBank: AAH04107.1) *Homo sapiens*:
(SEQ ID NO: 3)
MVRARHQPGG LCLLLLLLCQ FMEDRSAQAG NCWLRQAKNG RCQVLYKTEL SKEECCSTGR

LSTSWTEEDV NDNTLFKWMI FNGGAPNCIP CK-ETCENVDC GPGKKCRMNK KNKPRCVCAP

DCSNITWKGP VCGLDGKTYR NECALLKARC KEQPELEVQY QGRCKKTCRD VFCPGSSTCV

VDQTNNAYCV TCNRICPEPA SSEQYLCGND GVTYSSACHL RKATCLLGRS IGLAYEGKCI

KAKSCEDIQC TGGKKCLWDF KVGRGRCSLC DELCPDSKSD EPVCASDNAT YASECAMKEA

ACSSGVLLEV KHSGSCNSIS EDTEEEEEDE DQDYSFPISS ILEW

DAN (GenBank: BAA92265.1) *Homo sapiens*:
(SEQ ID NO: 4)
MLRVLVGAVL PAMLLAAPPP INKLALFPDK SAWCEAKNIT QIVGHSGCEA KSIQNRACLG

QCFSYSVPNT FPQSTESLVH CDSCMPAQSM WEIVTLECPG HEEVPRVDKL VEKILHCSCQ

ACGKEPSHEG LSVYVQGEDG PGSQPGTHPH PHPHPHPGGQ TPEPEDPPGA PHTEEEGAED

Cerberus (NCBI Reference Sequence: NP_005445.1) *Homo sapiens*:
(SEQ ID NO: 5)
MHLLLFQLLV LLPLGKTTRH QDGRQNQSSL SPVLLPRNQR ELPTGNHEEA EEKPDLFVAV

PHLVATSPAG EGQRQREKML SRFGRFWKKP EREMHPSRDS DSEPFPPGTQ SLIQPIDGMK

MEKSPLREEA KKFWHHFMFR KTPASQGVIL PIKSHEVHWE TCRTVPFSQT ITHEGCEKVV

VQNNLCFGKC GSVHFPGAAQ HSHTSCSHCL PAKFTTMHLP LNCTELSSVI KVVMLVEECQ

CKVKTEHEDG HILHAGSQDS FIPGVSA

Gremlin (GenBank: AAF06677.1) *Homo sapiens*:
(SEQ ID NO: 6)
MSRTAYTVGA LLLLLGTLLP AAEGKKKGSQ GAIPPPDKAQ HNDSEQTQSP QQPGSRNRGR

GQGRGTAMPG EEVLESSQEA LHVTERKYLK RDWCKTQPLK QTIHEEGCNS RTIINRFCYG

QCNSFYIPRH IRKEEGSFQS CSFCKPKKFT TMMVTLNCPE LQPPTKKKRV TRVKQCRCIS

IDLD

Sclerostin/SOST (GenBank: AAK13451.1) *Homo sapiens*:
(SEQ ID NO: 7)
MQLPLALCLV CLLVHTAFRV VEGQGWQAFK NDATEI IPEL GEYPEPPPEL ENNKTMNRAE

NGGRPPHHPF ETKDVSEYSC RELHFTRYVT DGPCRSAKPV TELVCSGQCG PARLLPNAIG

RGKWWRPSGP DFRCIPDRYR AQRVQLLCPG GEAPRARKVR LVASCKCKRL TRFHNQSELK

DFGTEAARPQ KGRKPRPRAR SAKANQAELE NAY

Decorin (GenBank: AAB60901.1) *Homo sapiens*:
(SEQ ID NO: 8)
MKATI ILLLL AQVSWAGPFQ QRGLFDFMLE DEASGIGPEV PDDRDFEPSL GPVCPFRCQC

HLRVVQCSDL alpha-2 macroglobulin (GenBank: EAW88590.1) *Homo sapiens*:
(SEQ ID NO 9)
MGKNKLLHPS LVLLLLVLLP TDASVSGKPQ YMVLVPSLLH TETTEKGCVL LSYLNETVTV

SASLESVRGN RSLFTDLEAE NDVLHCVAFA VPKSSSNEEV MFLTVQVKGP TQEFKKRTTV

MVKNEDSLVF VQTDKSIYKP GQTVKFRVVS MDENFHPLNE LIPLVYIQDP KGNRIAQWQS

FQLEGGLKQF SFPLSSEPFQ GSYKVVVQKK SGGRTEHPFT VEEFVLPKFE VQVTVPKIIT

ILEEEMNVSV CGLYTYGKPV PGHVTVSICR KYSDASDCHG EDSQAFCEKF SGQLNSHGCF

YQQVKTKVFQ LKRKEYEMKL HTEAQIQEEG TVVELTGRQS SEITRTITKL SFVKVDSHFR

QGIPFFGQVR LVDGKGVPIP NKVIFIRGNE ANYYSNATTD EHGLVQFSIN TTNVMGTSLT

```
VRVNYKDRSP CYGYQWVSEE HEEAHHTAYL VFSPSKSFVH LEPMSHELPC GHTQTVQAHY

ILNGGTLLGL KKLSFYYLIM AKGGIVRTGT HGLLVKQEDM KGHFSISIPV KSDIAPVARL

LIYAVLPTGD VIGDSAKYDV ENCLANKVDL SFSPSQSLPA SHAHLRVTAA PQSVCALRAV

DQSVLLMKPD AELSASSVYN LLPEKDLTGF PGPLNDQDDE DCINRHNVYI NGITYTPVSS

TNEKDMYSFL EDMGLKAFTN SKIRKPKMCP QLQQYEMHGP EGLRVGFYES DVMGRGHARL

VHVEEPHTET VRKYFPETWI WDLVVVNSAG VAEVGVTVPD TITEWKAGAF CLSEDAGLGI

SSTASLRAFQ PFFVELTMPY SVIRGEAFTL KATVLNYLPK CIRVSVQLEA SPAFLAVPVE

KEQAPHCICA NGRQTVSWAV TPKSLGNVNF TVSAEALESQ ELCGTEVPSV PEHGRKDTVI

KPLLVEPEGL EKETTFNSLL CPSGGEVSEE LSLKLPPNVV EESARASVSV LGDILGSAMQ

NTQNLLQMPY GCGEQNMVLF APNIYVLDYL NETQQLTPEI KSKAIGYLNT GYQRQLNYKH

YDGSYSTFGE RYGRNQGNTW LTAFVLKTFA QARAYIFIDE AHITQALIWL SQRQKDNGCF

RSSGSLLNNA IKGGVEDEVT LSAYITIALL EIPLTVTHPV VRNALFCLES AWKTAQEGDH

GSHVYTKALL AYAFALAGNQ DKRKEVLKSL NEEAVKKDNS VHWERPQKPK APVGHFYEPQ

APSAEVEMTS YVLLAYLTAQ PAPTSEDLTS ATNIVKWITK QQNAQGGFSS TQDTVVALHA

LSKYGAATFT RTGKAAQVTI QSSGTFSSKF QVDNNNRLLL QQVSLPELPG EYSMKVTGEG

CVYLQTSLKY NILPEKEEFP FALGVQTLPQ TCDEPKAHTS FQISLSVSYT GSRSASNMAI

VDVKMVSGFI PLKPTVKMLE RSNHVSRTEV SSNHVLIYLD KVSNQTLSLF FTVLQDVPVR

DLKPAIVKVY DYYETDEFAI AEYNAPCSKD LGNA

Wnt Agonists
R-spondin 1 (GenBank: ABC54570.1) Homo sapiens:
                                                   (SEQ ID NO: 10)
MRLGLCVVAL VLSWTHLTIS SRGIKGKRQR RISAEGSQAC AKGCELCSEV NGCLKCSPKL

FILLERNDIR QVGVCLPSCP PGYFDARNPD MNKCIKCKIE HCEACFSHNF CTKCKEGLYL

HKGRCYPACP EGSSAANGTM ECSSPAQCEM SEWSPWGPCS KKQQLCGFRR GSEERTRRVL

HAPVGDHAAC SDTKETRRCT VRRVPCPEGQ KRRKGGQGRR ENANRNLARK ESKEAGAGSR

RRKGQQQQQQ QGTVGPLTSA GPA

R-spondin 2 (NCBI Reference Sequence: NP_848660.3) Homo sapiens:
                                                   (SEQ ID NO: 11)
MQFRLFSFAL I ILNCMDYSH CQGNRWRRSK RASYVSNPIC KGCLSCSKDN GCSRCQQKLF

FFLRREGMRQ YGECLHSCPS GYYGHRAPDM NRCARCRIEN CDSCFSKDFC TKCKVGFYLH

RGRCFDECPD GFAPLEETME CVEGCEVGHW SEWGTCSRNN RTCGFKWGLE TRTRQIVKKP

VKDTILCPTI AESRRCKMTM RHCPGGKRTP KAKEKRNKKK KRKLIERAQE QHSVFLATDR

ANQ

R-spondin 3 (NCBI Reference Sequence: NP_116173.2) Homo sapiens:
                                                   (SEQ ID NO: 12)
MHLRLISWLF I ILNFMEYIG SQNASRGRRQ RRMHPNVSQG CQGGCATCSD YNGCLSCKPR

LFFALERIGM KQIGVCLSSC PSGYYGTRYP DINKCTKCKA DCDTCFNKNF CTKCKSGFYL

HLGKCLDNCP EGLEANNHTM ECVSIVHCEV SEWNPWSPCT KKGKTCGFKR GTETRVREI I

QHPSAKGNLC PPTNETRKCT VQRKKCQKGE RGKKGRERKR KKPNKGESKE AIPDSKSLES

SKEIPEQREN KQQQKKRKVQ DKQKSVSVST VH

R-spondin 4 (NCBI Reference Sequence: NP_001025042.2) Homo sapiens:
isoform 1
                                                   (SEQ ID NO: 13)
MRAPLCLLLL VAHAVDMLAL NRRKKQVGTG LGGNCTGCI I CSEENGCSTC QQRLFLFIRR

EGIRQYGKCL HDCPPGYFGI RGQEVNRCKK CGATCESCFS QDFCIRCKRQ FYLYKGKCLP
```

```
TCPPGTLAHQ NTRECQGECE LGPWGGWSPC THNGKTCGSA WGLESRVREA GRAGHEEAAT

CQVLSESRKC PIQRPCPGER SPGQKKGRKD RRPRKDRKLD RRLDVRPRQP GLQP
```

R-spondin 4 (NCBI Reference Sequence: NP_001035096.1) *Homo sapiens*: isoform 2

(SEQ ID NO: 14)

```
MRAPLCLLLL VAHAVDMLAL NRRKKQVGTG LGGNCTGCI I CSEENGCSTC QQRLFLFIRR

EGIRQYGKCL HDCPPGYFGI RGQEVNRCKK CGATCESCFS QDFCIRCKRQ FYLYKGKCLP

TCPPGTLAHQ NTRECQERSP GQKKGRKDRR PRKDRKLDRR LDVRPRQPGL QP
```

Norrin
norrin precursor *Homo sapiens*
NCBI Reference Sequence: NP_000257.1

(SEQ ID NO: 15)

```
MRKHVLAASF SMLSLLVIMG DTDSKTDSSF IMDSDPRRCM RHHYVDS I SH PLYKCSSKMV

LLARCEGHCS QASRSEPLVS FSTVLKQPFR SSCHCCRPQT SKLKALRLRC SGGMRLTATY

RYILSCHCEE CNS
```

WNT3A *Homo sapiens*
GenBank: BAB61052.1

(SEQ ID NO: 16)

```
MAPLGYFLLL CSLKQALGSY PIWWSLAVGP QYSSLGSQPI LCASIPGLVP KQLRFCRNYV

EIMPSVAEGI KIGIQECQHQ FRGRRWNCTT VHDSLAIFGP VLDKATRESA FVHAIASAGV

AFAVTRSCAE GTAAICGCSS RHQGSPGKGW KWGGCSEDIE FGGMVSREFA DARENRPDAR

SAMNRHNNEA GRQAIASHMH LKCKCHGLSG SCEVKTCWWS QPDFRAIGDF LKDKYDSASE

MVVEKHRESR GWVETLRPRY TYFKVPTERD LVYYEASPNF CEPNPETGSF GTRDRTCNVS

SHGIDGCDLL CCGRGHNARA ERRREKCRCV FHWCCYVSCQ ECTRVYDVHT CK
```

WNT6 *Homo sapiens*
GenBank: AAG45154.1

(SEQ ID NO: 17)

```
AVGSPLVMDP TSICRKARRL AGRQAELCQA EPEVVAELAR GARLGVRECQ FQFRFRRWNC

SSHSKAFGRI LQQDIRETAF VFAITAAGAS HAVTQACSMG ELLQCGCQAP RGRAPPRPSG

LPGTPGPPGP AGSPEGSAAW EWGGCGDDVD FGDEKSRLFM DARHKRGRGD IRALVQLHNN

EAGRLAVRSH TRTECKCHGL SGSCALRTCW QKLPPFREVG ARLLERFHGA SRVMGTNDGK

ALLPAVRTLK PPGRADLLYA ADSPDFCAPN RRTGSPGTRG RACNSSAPDL SGCDLLCCGR

GHRQESVQLE ENCLCRFHWC CVVQCHRCRV RKELSLCL
```

Mitogenic Factors
FGF-2 = bFGF (niProtKB/Swiss-Prot: P09038.3) *Homo sapiens*:

(SEQ ID NO: 18)

```
MVGVGGGDVE DVTPRPGGCQ I SGRGARGCN GIPGAAAWEA ALPRRRPRRH PSVNPRSRAA

GSPRTRGRRT EERPSGSRLG DRGRGRALPG GRLGGRGRGR APERVGGRGR GRGTAAPRAA

PAARGSRPGP AGTMAAGSIT TLPALPEDGG SGAFPPGHFK DPKRLYCKNG GFFLRIHPDG

RVDGVREKSD PHIKLQLQAE ERGVVSIKGV CANRYLAMKE DGRLLASKCV TDECFFFERL

ESNNYNTYRS RKYTSWYVAL KRTGQYKLGS KTGPGQKAIL FLPMSAKS
```

FGF7 (GenBank: CAG46799.1) *Homo sapiens*:

(SEQ ID NO: 19)

```
MHKWILTWIL PTLLYRSCFH IICLVGTISL ACNDMTPEQM ATNVNCSSPE RHTRSYDYME

GGDIRVRRLF CRTQWYLRID KRGKVKGTQE MKNNYNIMEI RTVAVGIVAI KGVESEFYLA

MNKEGKLYAK KECNEDCNFK ELILENHYNT YASAKWTHNG GEMFVALNQK GIPVRGKKTK

KEQKTAHFLP MAIT
```

FGF10 (GenBank: CAG46489.1) *Homo sapiens*:

(SEQ ID NO: 20)

```
MWKWILTHCA SAFPHLPGCC CCFLLLFLV SSVPVTCQAL GQMVSPEAT NSSSSSFSSP

SSAGRHVRSY NHLQGDVRWR KLFSFTKYFL KIEKNGKVSG TKKENCPYS I LEITSVEIGV
```

```
VAVKAINSNY YLAMNKKGKL YGSKEFNNDC KLKERIEENG YNTYASFNWQ HNGRQMYVAL

NGKGAPRRGQ KTRRKNTSAH FLPMVVHS

EGF (GenBank: EAX06257.1) Homo sapiens:
                                                         (SEQ ID NO 21)
MLLTLI ILLP VVSKFSFVSL SAPQHWSCPE GTLAGNGNST CVGPAPPLIF SHGNSIFRID

TEGTNYEQLV VDAGVSVIMD FHYNEKRIYW VDLERQLLQR VFLNGSRQER VCNIEKNVSG

MAINWINEEV IWSNQQEGII TVTDMKGNNS HILLSALKYP ANVAVDPVER FIFWSSEVAG

SLYRADLDGV GVKALLETSE KITAVSLDVL DKRLFWIQYN REGSNSLICS CDYDGGSVHI

SKHPTQHNLF AMSLFGDRIF YSTWKMKTIW IANKHTGKDM VRINLHSSFV PLGELKVVHP

LAQPKAEDDT WEPEQKLCKL RKGNCSSTVC GQDLQSHLCM CAEGYALSRD RKYCEDVNEC

AFWNHGCTLG CKNTPGSYYC TCPVGFVLLP DGKRCHQLVS CPRNVSECSH DCVLTSEGPL

CFCPEGSVLE RDGKTCSGCS SPDNGGCSQL CVPLSPVSWE CDCFPGYDLQ LDEKSCAASG

PQPFLLFANS QDIRHMHFDG TDYGTLLSQQ MGMVYALDHD PVENKIYFAH TALKWIERAN

MDGSQRERLI EEGVDVPEGL AVDWIGRRFY WTDRGKSLIG RSDLNGKRSK IITKENISQP

RGIAVHPMAK RLFWTDTGIN PRIESSSLQG LGRLVIASSD LIWPSGITID FLTDKLYWCD

AKQSVIEMAN LDGSKRRRLT QNDVGHPFAV AVFEDYVWFS DWAMPSVMRV NKRTGKDRVR

LQGSMLKPSS LVVVHPLAKP GADPCLYQNG GCEHICKKRL GTAWCSCREG FMKASDGKTC

LALDGHQLLA GGEVDLKNQV TPLDILSKTR VSEDNITESQ HMLVAEIMVS DQDDCAPVGC

SMYARCISEG EDATCQCLKG FAGDGKLCSD IDECEMGVPV CPPASSKCIN TEGGYVCRCS

EGYQGDGIHC LDIDECQLGE HSCGENASCT NTEGGYTCMC AGRLSEPGLI CPDSTPPPHL

REDDHHYSVR NSDSECPLSH DGYCLHDGVC MYIEALDKYA CNCVVGYIGE RCQYRDLKWW

ELRHAGHGQQ QKVIVVAVCV VVLVMLLLLS LWGAHYYRTQ KLLSKNPKNP YEESSRDVRS

RRPADTEDGM SSCPQPWFVV IKEHQDLKNG GQPVAGEDGQ AADGSMQPTS WRQEPQLCGM

GTEQGCWIPV SSDKGSCPQV MERSFHMPSY GTQTLEGGVE KPHSLLSANP LWQQRALDPP

HQMELTQ

TGFa Homo sapiens: protransforming growth factor alpha isoform 1
preproprotein [Homo sapiens] NCBI Reference Sequence: NP_003227.1
                                                         (SEQ ID NO: 22)
MVPSAGQLAL FALGIVLAAC QALENSTSPL SADPPVAAAV VSHFNDCPDS HTQFCFHGTC

RFLVQEDKPA CVCHSGYVGA RCEHADLLAV VAASQKKQAI TALVVVSIVA LAVLIITCVL

IHCCQVRKHC EWCRALICRH EKPSALLKGR TACCHSETVV protransforming growth factor alpha isoform 2 preproprotein
[Homo sapiens] NCBI Reference Sequence: NP_001093161.1
                                                         (SEQ ID NO: 23)
MVPSAGQLAL FALGIVLAAC QALENSTSPL SDPPVAAAVV SHFNDCPDSH TQFCFHGTCR

FLVQEDKPAC VCHSGYVGAR CEHADLLAVV AASQKKQAIT ALVVVSIVAL AVLIITCVLI

HCCQVRKHCE WCRALICRHE KPSALLKGRT ACCHSETVV

Transforming growth factor alpha [synthetic construct]
GenBank: AAX43291.1
                                                         (SEQ ID NO: 24)
MVPLAGQLAL FALGIVLAAC QALENSTSPL SDPPVAAAVV SHFNDCPDSH TQFCFHGTCR

FLVQEDKPAC VCHSGYVGAR CEHADLLAVV AASQKKQAIT ALVVVSIVAL AVLIITCVLI

HCCQVRKHCE WCRALICRHE KPSALLKGRT ACCHSETVVL
```

-continued

TGF alpha containing:
(SEQ ID NO: 25)
VVSHFNDCPD SHTQFCFHGT CRFLVQEDKP ACVCHSGYVG ARCEHA DLLA BDNF (UniProtKB/Swiss-Prot: P23560.1) Homo sapiens:
(SEQ ID NO 26)
MTILFLTMVI SYFGCMKAAP MKEA IRGQG GLAYPGVRTH GTLESVNGPK AGSRGLTSLA

DTFEHVIEEL LDEDQKVRPN EENNKDADLY TSRVMLSSQV PLEPPLLFLL EEYKNYLDAA

NMSMRVRRHS DPARRGELSV CDSISEWVTA ADKKTAVDMS GGTVTVLEKV PVSKGQLKQY

FYETKCNPMG YTKEGCRGID KRHWNSQCRT TQSYVRALTM DSKKRIGWRF IRIDTSCVCT

LTIKRGR

KGF (GenBank: AAB21431.1) Homo sapiens:
(SEQ ID NO: 27)
MHKWILTWIL PTLLYRSCFH IICLVGTISL ACNDMTPEQM ATNVNCSSPE RHTRSYDYME

GGDIRVRRLF CRTQWYLRID KRGKVKGTQE MKNNYNIMEI RTVAVGIVAI KGVESEFYLA

MNKEGKLYAK KECNEDCNFK ELILENHYNT YASAKWTHNG GEMFVALNQK GIPVRGKKTK

KEQKTAHFLP MAIT

5. Methods for Differentiating the Stem Cells

The isolated stem cells (e.g., epithelial stem cells) may be induced to differentiate into differentiated cells that normally reside in the tissue or organ from which the stem cells originate or are isolated. Other tissues include fallopian tubes, endometrium (uterus), male efferent ducts, male epididymis, male vas deferens, male ejaculatory duct, male bulbourethral glands, and seminal vesicle glands. The differentiated cells may express markers characteristic of the differentiated cells, and can be readily distinguished from the stem cells which do not express such differentiated cell markers.

6. Markers

In general, gene expression may be measured at RNA level for all of the markers described below. In addition, the expression of certain markers can also be detected by protein expression using, for example, antibody specific for proteins encoded by the marker genes.

7. Methods of Use

In a further aspect, the invention provides the use of the subject stem cells isolated from the various cultures in a drug discovery screen, toxicity assay, animal-based disease model, or in medicine, such as regenerative medicine.

Genetic Manipulation of Cloned Stem Cells

For instance, stem cells isolated by the methods of the invention are suitable for numerous types of genetic manipulation, including introduction of exogenous genetic materials that may modulate the expression of one or more target genes of interest. Such kind of gene therapy can be used, for example, in a method directed at repairing damaged or diseased tissue. In brief, any suitable vectors, including an adenoviral, elntiviral, or retroviral gene delivery vehicle (see below), may be used to deliver genetic information, like DNA and/or RNA to any of the subject stem cells. A skilled person can replace or repair particular genes targeted in gene therapy. For example, a normal gene may be inserted into a nonspecific location within the genome of a diseased cell to replace a nonfunctional gene. In another example, an abnormal gene sequence can be replaced for a normal gene sequence through homologous recombination. Alternatively, selective reverse mutation can return a gene to its normal function. A further example is altering the regulation (the degree to which a gene is turned on or off) of a particular gene. Preferably, the stem cells are ex vivo treated by a gene therapy approach and are subsequently transferred to the mammal, preferably a human being in need of treatment.

Any art recognized methods for genetic manipulation may be applied to the stem cells so isolated, including transfection and infection (e.g., by a viral vector) by various types of nucleic acid constructs.

For example, heterologous nucleic acids (e.g., DNA) can be introduced into the subject stem cells by way of physical treatment (e.g., electroporation, sonoporation, optical transfection, protoplast fusion, impalefection, hydrodynamic delivery, nanoparticles, magnetofection), using chemical materials or biological vectors (viruses). Chemical-based transfection can be based on calcium phosphate, cyclodextrin, polymers (e.g., cationic polymers such as DEAE-dextran or polyethylenimine), highly branched organic compounds such as dendrimers, liposomes (such as cationic liposomes, lipofection such as lipofection using Lipofectamine, etc.), or nanoparticles (with or without chemical or viral functionalization).

A nucleic acid construct comprises a nucleic acid molecule of interest, and is generally capable of directing the expression of the nucleic acid molecule of interest in the cells into which it has been introduced.

In certain embodiments, the nucleic acid construct is an expression vector wherein a nucleic acid molecule encoding a gene product, such as a polypeptide or a nucleic acid that antagonizes the expression of a polypeptide (e.g., an siRNA, miRNA, shRNA, antisense sequence, aptamer, rybozyme etc.) is operably linked to a promoter capable of directing expression of the nucleic acid molecule in the target cells (e.g., the isolated stem cell).

The term "expression vector" generally refers to a nucleic acid molecule that is capable of effecting expression of a gene/nucleic acid molecule it contains in a cell compatible with such sequences. These expression vectors typically include at least suitable promoter sequences and optionally, transcription termination signals. A nucleic acid or DNA or nucleotide sequence encoding a polypeptide is incorporated into a DNA/nucleic acid construct capable of introduction into and expression in an in vitro cell culture as identified in a method of the invention.

A DNA construct prepared for introduction into a particular cell typically include a replication system recognized by the cell, an intended DNA segment encoding a desired polypeptide, and transcriptional and translational initiation and termination regulatory sequences operably linked to the polypeptide-encoding segment. A DNA segment is "operably linked" when it is placed into a functional relationship with another DNA segment. For example, a promoter or enhancer is operably linked to a coding sequence if it stimulates the transcription of the sequence. DNA for a signal sequence is operably linked to DNA encoding a polypeptide if it is expressed as a preprotein that participates in the secretion of a polypeptide. Generally, a DNA sequence that is operably linked are contiguous, and, in the case of a signal sequence, both contiguous and in reading phase. However, enhancers need not be contiguous with a coding sequence whose transcription they control. Linking is accomplished by ligation at convenient restriction sites or at adapters or linkers inserted in lieu thereof.

The selection of an appropriate promoter sequence generally depends upon the host cell selected for the expression of a DNA segment. Examples of suitable promoter sequences include eukaryotic promoters well known in the art (see, e.g., Sambrook and Russell, Molecular Cloning: A Laboratory Manual, Third Edition, 2001). A transcriptional regulatory sequence typically includes a heterologous enhancer or promoter that is recognized by the cell. Suitable promoters include the CMV promoter. An expression vector includes the replication system and transcriptional and translational regulatory sequences together with the insertion site for the polypeptide encoding segment can be employed. Examples of workable combinations of cell lines and expression vectors are described in Sambrook and Russell (2001, supra) and in Metzger et al. (1988) Nature 334: 31-36.

Some aspects of the invention concern the use of a nucleic acid construct or expression vector comprising a nucleotide sequence as defined above, wherein the vector is a vector that is suitable for gene therapy. Vectors that are suitable for gene therapy are known in the art, such as those described in Anderson (Nature 392: 25-30, 1998); Walther and Stein (Drugs 60: 249-71, 2000); Kay et al. (Nat. Med. 7: 33-40, 2001); Russell (J. Gen. Virol. 81:2573-604, 2000); Amado and Chen (Science 285:674-6, 1999); Federico (Curr. Opin. Biotechnol. 10:448-53, 1999); Vigna and Naldini (J. Gene Med. 2:308-16, 2000); Marin et al. (Mol. Med. Today 3:396-403, 1997); Peng and Russell (Curr. Opin. Biotechnol. 10:454-7, 1999); Sommerfelt (J. Gen. Virol. 80:3049-64, 1999); Reiser (Gene Ther. 7: 910-3, 2000); and references cited therein (all incorporated by reference). Examples include integrative and non-integrative vectors such as those based on retroviruses, adenoviruses (AdV), adeno-associated viruses (AAV), lentiviruses, pox viruses, alphaviruses, and herpes viruses.

A particularly suitable gene therapy vector includes an Adenoviral (Ad) and Adeno-associated virus (AAV) vector. These vectors infect a wide number of dividing and non-dividing cell types. In addition, adenoviral vectors are capable of high levels of transgene expression. However, because of the episomal nature of the adenoviral and AAV vectors after cell entry, these viral vectors are most suited for therapeutic applications requiring only transient expression of the transgene (Russell, J. Gen. Virol. 81:2573-2604, 2000; Goncalves, Virol J. 2(1):43, 2005) as indicated above. Preferred adenoviral vectors are modified to reduce the host response as reviewed by Russell (2000, supra). Safety and efficacy of AAV gene transfer has been extensively studied in humans with encouraging results in the liver, muscle, CNS, and retina (Manno et al, Nat. Medicine 2006; Stroes et al., A'T'YB 2008; Kaplitt, Feigin, Lancet 2009; Maguire, Simonelli et al. NEJM 2008; Bainbridge et al., NEJM 2008).

AAV2 is the best characterized serotype for gene transfer studies both in humans and experimental models. AAV2 presents natural tropism towards skeletal muscles, neurons, vascular smooth muscle cells and hepatocytes. Other examples of adeno-associated virus-based non-integrative vectors include AAVI, AAV3, AAV4, AAV5, AAV 6, AAV7, AAV8, AAV9, AAV 10, AAVI 1 and pseudotyped AAV. The use of non-human serotypes, like AAV8 and AAV9, might be useful to overcome these immunological responses in subjects, and clinical trials have just commenced (ClinicalTrials dot gov Identifier: NCT00979238). For gene transfer into a liver cell, an adenovirus serotype 5 or an AAV serotype 2, 7 or 8 have been shown to be effective vectors and therefore a preferred Ad or AAV serotype (Gao, Molecular Therapy 13:77-87, 2006).

An exemplary retroviral vector for application in the present invention is a lentiviral based expression construct. Lentiviral vectors have the unique ability to infect non-dividing cells (Amado and Chen, Science 285:674-676, 1999). Methods for the construction and use of lentiviral based expression constructs are described in U.S. Pat. Nos. 6,165,782, 6,207,455, 6,218,181, 6,277,633, and 6,323,031, and in Federico (Curr. Opin. Biotechnol. 10:448-53, 1999) and Vigna et al. (J. Gene Med. 2:308-16, 2000). Generally, gene therapy vectors will be as the expression vectors described above in the sense that they comprise a nucleotide sequence encoding a gene product (e.g., a polypeptide) of the invention to be expressed, whereby a nucleotide sequence is operably linked to the appropriate regulatory sequences as indicated above. Such regulatory sequence will at least comprise a promoter sequence. Suitable promoters for expression of a nucleotide sequence encoding a polypeptide from gene therapy vectors include, e.g., cytomegalovirus (CMV) intermediate early promoter, viral long terminal repeat promoters (LTRs), such as those from murine Moloney leukaemia virus (MMLV) rous sarcoma virus, or HTLV-1, the simian virus 40 (SV 40) early promoter and the herpes simplex virus thymidine kinase promoter. Additional suitable promoters are described below.

Several inducible promoter systems have been described that may be induced by the administration of small organic or inorganic compounds. Such inducible promoters include those controlled by heavy metals, such as the metallothionine promoter (Brinster et al, Nature 296:39-42, 1982; Mayo et al, Cell 29:99-108, 1982), RU-486 (a progesterone antagonist) (Wang et al, Proc. Natl. Acad. Sci. USA 91:8180-8184, 1994), steroids (Mader and White, Proc. Natl. Acad. Sci. USA 90:5603-5607, 1993), tetracycline (Gossen and Bujard, Proc. Natl. Acad. Sci. USA 89:5547-5551, 1992; U.S. Pat. No. 5,464,758; Furth et al, Proc. Natl. Acad. Sci. USA 91:9302-9306, 1994; Howe et al, J. Biol. Chem. 270:14168-14174, 1995; Resnitzky et al, Mol. Cell. Biol. 14:1669-1679, 1994; Shockett et al, Proc. Natl. Acad. Sci. USA 92:6522-6526, 1995) and the tTAER system that is based on the multi-chimeric transactivator composed of a tetR polypeptide, as activation domain of VP 16, and a ligand binding domain of an estrogen receptor (Yee et al, 2002, U.S. Pat. No. 6,432,705).

Suitable promoters for nucleotide sequences encoding small RNAs for knock down of specific genes by RNA interference (see below) include, in addition to the above-mentioned polymerase II promoters, polymerase III promoters. The RNA polymerase III (pol III) is responsible for the synthesis of a large variety of small nuclear and cytoplasmic non-coding RNAs including 5S, U6, adenovirus VA1, Vault, telomerase RNA, and tRNAs. The promoter structures of a large number of genes encoding these RNAs have been determined and it has been found that RNA pol III promoters fall into three types of structures (for a review see Geiduschek and Tocchini-Valentini, Annu. Rev. Biochem. 57: 873-914, 1988; Willis, Eur. J. Biochem. 212: 1-11, 1993; Hernandez, J. Biol. Chem. 276:26733-36, 2001). Particularly suitable for expression of siRNAs are the type 3 of the RNA pol III promoters, whereby transcription is driven by cis-acting elements found only in the 5'-flanking region, i.e., upstream of the transcription start site. Upstream sequence elements include a traditional TATA box (Mattaj et al., Cell 55:435-442, 1988), proximal sequence element and a distal sequence element (DSE; Gupta and Reddy, Nucleic Acids Res. 19:2073-2075, 1991).

Examples of genes under the control of the type 3 pol III promoter are U6 small nuclear RNA (U6 snRNA), 7SK, Y, MRP, HI and telomerase RNA genes (see, e.g., Myslinski et al, Nucl. Acids Res. 21:2502-09, 2001).

A gene therapy vector may optionally comprise a second or one or more further nucleotide sequence coding for a second or further polypeptide. A second or further polypeptide may be a (selectable) marker polypeptide that allows for the identification, selection and/or screening for cells containing the expression construct. Suitable marker proteins for this purpose are, e.g., the fluorescent protein GFP, and the selectable marker genes HSV thymidine kinase (for selection on HAT medium), bacterial hygromycin B phosphotransferase (for selection on hygromycin B), Tn5 aminoglycoside phosphotransferase (for selection on G418), and dihydrofolate reductase (DHFR) (for selection on methotrexate), CD20, the low affinity nerve growth factor gene. Sources for obtaining these marker genes and methods for their use are provided in Sambrook and Russell, Molecular Cloning: A Laboratory Manual (3rd edition), Cold Spring Harbor Laboratory, Cold Spring Harbor Laboratory Press, New York, 2001.

Alternatively, a second or further nucleotide sequence may encode a polypeptide that provides for fail-safe mechanism that allows a subject from the transgenic cells to be cured, if deemed necessary. Such a nucleotide sequence, often referred to as a suicide gene, encodes a polypeptide that is capable of converting a prodrug into a toxic substance that is capable of killing the transgenic cells in which the polypeptide is expressed. Suitable examples of such suicide genes include, e.g., the E. coli cytosine deaminase gene or one of the thymidine kinase genes from Herpes Simplex Virus, Cytomegalovirus and Varicella-Zoster virus, in which case ganciclovir may be used as prodrug to kill the IL-10 transgenic cells in the subject (see, e.g., Clair et al., Antimicrob. Agents Chemother. 31:844-849, 1987).

For knock down of expression of a specific polypeptide, a gene therapy vector or other expression construct is used for the expression of a desired nucleotide sequence that preferably encodes an RNAi agent, i.e., an RNA molecule that is capable of RNA interference or that is part of an RNA molecule that is capable of RNA interference. Such RNA molecules are referred to as siRNA (short interfering RNA, including, e.g., a short hairpin RNA). A desired nucleotide sequence comprises an antisense code DNA coding for the antisense RNA directed against a region of the target gene mRNA, and/or a sense code DNA coding for the sense RNA directed against the same region of the target gene mRNA. In a DNA construct of the invention, an antisense and sense code DNAs are operably linked to one or more promoters as herein defined above that are capable of expressing an antisense and sense RNAs, respectively. "siRNA" includes a small interfering RNA that is a short-length double-stranded RNA that is not toxic in mammalian cells (Elbashir et al, Nature 411:494-98, 2001; Caplen et al, Proc. Natl. Acad. Sci. USA 98:9742-47, 2001). The length is not necessarily limited to 21 to 23 nucleotides. There is no particular limitation in the length of siRNA as long as it does not show toxicity. "siRNAs" can be, e.g., at least about 15, 18 or 21 nucleotides and up to 25, 30, 35 or 49 nucleotides long. Alternatively, the double-stranded RNA portion of a final transcription product of siRNA to be expressed can be, e.g., at least about 15, 18 or 21 nucleotides, and up to 25, 30, 35 or 49 nucleotides long.

"Antisense RNA" is preferably an RNA strand having a sequence complementary to a target gene mRNA, and thought to induce RNAi by binding to the target gene mRNA.

"Sense RNA" has a sequence complementary to the antisense RNA, and annealed to its complementary antisense RNA to form siRNA.

The term "target gene" in this context includes a gene whose expression is to be silenced due to siRNA to be expressed by the present system, and can be arbitrarily selected. As this target gene, for example, genes whose sequences are known but whose functions remain to be elucidated, and genes whose expressions are thought to be causative of diseases are preferably selected. A target gene may be one whose genome sequence has not been fully elucidated, as long as a partial sequence of mRNA of the gene having at least 15 nucleotides or more, which is a length capable of binding to one of the strands (antisense RNA strand) of siRNA, has been determined. Therefore, genes, expressed sequence tags (ESTs) and portions of mRNA, of which some sequence (preferably at least 15 nucleotides) has been elucidated, may be selected as the "target gene" even if their full length sequences have not been determined.

The double-stranded RNA portions of siRNAs in which two RNA strands pair up are not limited to the completely paired ones, and may contain nonpairing portions due to mismatch (the corresponding nucleotides are not complementary), bulge (lacking in the corresponding complementary nucleotide on one strand), and the like. A non-pairing portions can be contained to the extent that they do not interfere with siRNA formation. The "bulge" used herein may comprise 1 to 2 non-pairing nucleotides, and the double-stranded RNA region of siRNAs in which two RNA strands pair up contains preferably 1 to 7, more preferably 1 to 5 bulges.

The term "mismatch" as used herein may be contained in the double-stranded RNA region of siRNAs in which two RNA strands pair up, preferably 1 to 7, more preferably 1 to 5, in number. In certain mismatch, one of the nucleotides is guanine, and the other is uracil. Such a mismatch is due to a mutation from C to T, G to A, or mixtures thereof in DNA coding for sense RNA, but not particularly limited to them. Furthermore, in the present invention, a double-stranded RNA region of siRNAs in which two RNA strands pair up may contain both bulge and mismatched, which sum up to, preferably 1 to 7, more preferably 1 to 5 in number. Such non-pairing portions (mismatches or bulges, etc.) can suppress the below-described recombination between antisense and sense code DNAs and make the siRNA expression system as described below stable. Furthermore, although it is difficult to sequence stem loop DNA containing no non-pairing portion in the double-stranded RNA region of siRNAs in which two RNA strands pair up, the sequencing is enabled by introducing mismatches or bulges as described above. Moreover, siRNAs containing mismatches or bulges in the pairing double-stranded RNA region have the advantage of being stable in E. coli or animal cells.

The terminal structure of siRNA may be either blunt or cohesive (overhanging) as long as siRNA enables to silence the target gene expression due to its RNAi effect. The cohesive (overhanging) end structure is not limited only to the 3' overhang, and the 5' overhanging structure may be included as long as it is capable of inducing the RNAi effect. In addition, the number of overhanging nucleotide is not limited to the already reported 2 or 3, but can be any numbers as long as the overhang is capable of inducing the RNAi effect. For example, the overhang consists of 1 to 8, preferably 2 to 4 nucleotides. Herein, the total length of siRNA having cohesive end structure is expressed as the sum of the length of the paired double-stranded portion and that of a pair comprising overhanging single-strands at both ends. For example, in the case of 19 bp double-stranded RNA portion with 4 nucleotide overhangs at both ends, the total length is expressed as 23 bp. Furthermore, since this overhanging sequence has low specificity to a target gene, it is not necessarily complementary (antisense) or identical (sense) to the target gene sequence. Furthermore, as long as siRNA is able to maintain its gene silencing effect on the target gene, siRNA may contain a low molecular weight RNA (which may be a natural RNA molecule such as tRNA, rRNA or viral RNA, or an artificial RNA molecule), for example, in the overhanging portion at its one end.

In addition, the terminal structure of the "siRNA" is necessarily the cut off structure at both ends as described above, and may have a stem-loop structure in which ends of one side of double-stranded RNA are connected by a linker RNA (a "shRNA"). The length of the double-stranded RNA region (stem-loop portion) can be, e.g., at least 15, 18 or 21 nucleotides and up to 25, 30, 35 or 49 nucleotides long. Alternatively, the length of the double-stranded RNA region that is a final transcription product of siRNAs to be expressed is, e.g., at least 15, 18 or 21 nucleotides and up to 25, 30, 35 or 49 nucleotides long.

Furthermore, there is no particular limitation in the length of the linker as long as it has a length so as not to hinder the pairing of the stem portion. For example, for stable pairing of the stem portion and suppression of the recombination between DNAs coding for the portion, the linker portion may have a clover-leaf tRNA structure. Even though the linker has a length that hinders pairing of the stem portion, it is possible, for example, to construct the linker portion to include introns so that the introns are excised during processing of precursor RNA into mature RNA, thereby allowing pairing of the stem portion. In the case of a stem-loop siRNA, either end (head or tail) of RNA with no loop structure may have a low molecular weight RNA. As described above, this low molecular weight RNA may be a natural RNA molecule such as tRNA, rRNA, snRNA or viral RNA, or an artificial RNA molecule.

To express antisense and sense RNAs from the antisense and sense code DNAs respectively, a DNA construct of the present invention comprise a promoter as defined above. The number and the location of the promoter in the construct can in principle be arbitrarily selected as long as it is capable of expressing antisense and sense code DNAs. As a simple example of a DNA construct of the invention, a tandem expression system can be formed, in which a promoter is located upstream of both antisense and sense code DNAs. This tandem expression system is capable of producing siRNAs having the aforementioned cut off structure on both ends. In the stem-loop siRNA expression system (stem expression system), antisense and sense code DNAs are arranged in the opposite direction, and these DNAs are connected via a linker DNA to construct a unit. A promoter is linked to one side of this unit to construct a stem-loop siRNA expression system. Herein, there is no particular limitation in the length and sequence of the linker DNA, which may have any length and sequence as long as its sequence is not the termination sequence, and its length and sequence do not hinder the stem portion pairing during the mature RNA production as described above. As an example, DNA coding for the above-mentioned tRNA and such can be used as a linker DNA.

In both cases of tandem and stem-loop expression systems, the 5' end may be have a sequence capable of promoting the transcription from the promoter. More specifically, in the case of tandem siRNA, the efficiency of siRNA production may be improved by adding a sequence capable of promoting the transcription from the promoters at the 5' ends of antisense and sense code DNAs. In the case of stem-loop siRNA, such a sequence can be added at the 5' end of the above-described unit. A transcript from such a sequence may be used in a state of being attached to siRNA as long as the target gene silencing by siRNA is not hindered. If this state hinders the gene silencing, it is preferable to perform trimming of the transcript using a trimming means (for example, ribozyme as are known in the art). It will be clear to the skilled person that an antisense and sense RNAs may be expressed in the same vector or in different vectors. To avoid the addition of excess sequences downstream of the sense and antisense RNAs, it is preferred to place a terminator of transcription at the 3' ends of the respective strands (strands coding for antisense and sense RNAs). The terminator may be a sequence of four or more consecutive adenine (A) nucleotides.

Genome Editing

Genome editing may be used to change the genomic sequence of the subject cloned stem cells, including cloned cancer (or other disease) stem cells, by introducing heterologous transgene or by inhibiting expression of a target endogenous gene. Such genetically engineered stem cells can be used, for regenerative medicine (see below) or wound healing. Thus, in certain embodiments, the subject methods of regenerative medicine (see below) comprise using a subject stem cell the genome sequence of which has been modified by genomic editing.

Genome editing may be performed using any art-recognized technology, such as ZFN/TALEN or CRISPR technologies (see review by Gaj et al, Trends in Biotech. 31(7): 397-405, 2013, the entire text and all cited references therein are incorporated herein by reference). Such technologies enable one to manipulate virtually any gene in a diverse range of cell types and organisms, thus enabling a broad range of genetic modifications by inducing DNA double-strand (DSB) breaks that stimulate error-prone nonhomologous end joining (NHEJ) or homology-directed repair (HDR) at specific genomic locations.

Zinc-finger nucleases (ZFNs) and Transcription activator-like effector nucleases (TALENs) are chimeric nucleases composed of programmable, sequence-specific DNA-binding modules linked to a nonspecific DNA cleavage domain. They are artificial restriction enzymes (REs) generated by fusing a zinc-finger or TAL effector DNA binding domain to a DNA cleavage domain. A zinc-finger (ZF) or transcription activator-like effector (TALE) can be engineered to bind any desired target DNA sequence, and be fused to a DNA cleavage domain of an RE, thus creating an engineer restriction enzyme (ZFN or TALEN) that is specific for the desired target DNA sequence. When ZFN/TALEN is introduced into cells, it can be used for genome editing in situ. Indeed, the versatility of the ZFNs and TALENs can be expanded to effector domains other than nucleases, such as transcription activators and repressors, recombinases, transposases, DNA and histone methyl transferases, and histone acetyltransferases, to affect genomic structure and function.

The Cys2-His2 zinc-finger domain is among the most common types of DNA-binding motifs found in eukaryotes and represents the second most frequently encoded protein domain in the human genome. An individual zinc-finger has about 30 amino acids in a conserved ββα configuration. Key to the application of zinc-finger proteins for specific DNA recognition was the development of unnatural arrays that contain more than three zinc-finger domains. This advance was facilitated by the structure-based discovery of a highly conserved linker sequence that enabled construction of synthetic zinc-finger proteins that recognized DNA sequences 9-18 bp in length. This design has proven to be the optimal strategy for constructing zinc-finger proteins that recognize contiguous DNA sequences that are specific in complex genomes. Suitable zinc-fingers may be obtained by modular assembly approach (e.g., using a preselected library of zinc-finger modules generated by selection of large combinatorial libraries or by rational design). Zinc-finger domains have been developed that recognize nearly all of the 64 possible nucleotide triplets, preselected zinc-finger modules can be linked together in tandem to target DNA sequences that contain a series of these DNA triplets. Alternatively, selection-based approaches, such as oligomerized pool engineering (OPEN) can be used to select for new zinc-finger arrays from randomized libraries that take into consideration context-dependent interactions between neighboring fingers. A combination of the two approaches is also used.

Engineered zinc fingers are commercially available. Sangamo Biosciences (Richmond, Calif., USA) has developed a propriety platform (CompoZr) for zinc-finger construction in partnership with Sigma-Aldrich (St. Louis, Mo., USA), which platform allows investigators to bypass zinc-finger construction and validation altogether, and many thousands of proteins are already available. Broadly, zinc-finger protein technology enables targeting of virtually any sequence.

TAL effectors are proteins secreted by the plant pathogenic Xanthomonas bacteria, with DNA binding domain containing a repeated highly conserved 33-34 amino acid sequence, with the exception of the 12th and 13th amino acids. These two locations are highly variable (Repeat Variable Diresidue, or RVD) and show a strong correlation with specific nucleotide recognition. This simple relationship between amino acid sequence and DNA recognition has allowed for the engineering of specific DNA binding domains by selecting a combination of repeat segments containing the appropriate RVDs. Like zinc fingers, modular TALE repeats are linked together to recognize contiguous DNA sequences. Numerous effector domains have been made available to fuse to TALE repeats for targeted genetic modifications, including nucleases, transcriptional activators, and site-specific recombinases. Rapid assembly of custom TALE arrays can be achieved by using strategies include "Golden Gate" molecular cloning, high-throughput solid-phase assembly, and ligation-independent cloning techniques, all can be used in the instant invention for genome editing of the cloned stem cells.

TALE repeats can be easily assembled using numerous tools available in the art, such as a library of TALENs targeting 18,740 human protein-coding genes (Kim et al., Nat. Biotechnol. 31, 251-258, 2013). Custom-designed TALE arrays are also commercially available through, for example, Cellectis Bioresearch (Paris, France), Transposagen Biopharmaceuticals (Lexington, Ky., USA), and Life Technologies (Grand Island, N.Y., USA).

The non-specific DNA cleavage domain from the end of a RE, such as the FokI endonuclease (or FokI cleavage domain variants, such as Sharkey, with mutations designed to improve cleavage specificity and/or cleavage activity), can be used to construct hybrid nucleases that are active in a yeast assay (also active in plant cells and in animal cells). To improve ZFN activity, transient hypothermic culture conditions can be used to increase nuclease expression levels; co-delivery of site-specific nucleases with DNA end-processing enzymes, and the use of fluorescent surrogate reporter vectors that allow for the enrichment of ZFN- and TALEN-modified cells, may also be used. The specificity of ZFN-mediated genome editing can also be refined by using zinc-finger nickases (ZFNickases), which take advantage of the finding that induction of nicked DNA stimulates HDR without activating the error-prone NHEJ repair pathway.

The simple relationship between amino acid sequence and DNA recognition of the TALE binding domain allows for designable proteins. A publicly available software program (DNAWorks) can be used to calculate oligonucleotides suitable for assembly in a two-step PCR. A number of modular assembly schemes for generating engineered TALE constructs have also been reported and known in the art. Both methods offer a systematic approach to engineering DNA binding domains that is conceptually similar to the modular assembly method for generating zinc finger DNA recognition domains.

Once the TALEN genes have been assembled, they are introduced into the target cell on a vector using any art recognized methods (such as electroporation or transfection using cationic lipid-based reagents, using plasmid vectors, various viral vectors such as adenoviral, AAV, and Integrase-deficient lentiviral vectors (IDLVs)). Alternatively, TALENs can be delivered to the cell as mRNA, which removes the possibility of genomic integration of the TALEN-expressing protein. It can also dramatically increase the level of homology directed repair (HDR) and the success of introgression during gene editing. Finally, direct delivery of purified ZFN/TALEN proteins into cells may also be used. This approach does not carry the risk of insertional mutagenesis, and leads to fewer off-target effects than delivery systems that rely on expression from nucleic acids, and thus may be optimally used for studies that require precise genome engineering in cells, such as the instant stem cells.

TALENs can be used to edit genomes by inducing double-strand breaks (DSB), which cells respond to with repair mechanisms. Non-homologous end joining (NHEJ) reconnects DNA from either side of a double-strand break where there is very little or no sequence overlap for annealing. A simple heteroduplex cleavage assay can be run which detects any difference between two alleles amplified by PCR. Cleavage products can be visualized on simple agarose gels or slab gel systems. Alternatively, DNA can be introduced into a genome through NHEJ in the presence of exogenous double-stranded DNA fragments.

Homology directed repair can also introduce foreign DNA at the DSB as the transfected double-stranded sequences are used as templates for the repair enzymes. TALENs have been used to generate stably modified human embryonic stem cell and induced pluripotent stem cell (iPSCs) clones to generate knockout *C. elegans*, rats, and zebrafish.

For stem cell based therapy, ZFNs and TALENs are capable of correcting the underlying cause of the disease, therefore permanently eliminating the symptoms with precise genome modifications. For example, ZFN-induced HDR has been used to directly correct the disease-causing mutations associated with X-linked severe combined immune deficiency (SCJD), hemophilia B, sickle-cell disease, al-antitrypsin deficiency and numerous other genetic diseases, either by repair defective target genes, or by knocking out a target gene. In addition, these site-specific nucleases can also be used to safely insert therapeutic transgenes into the subject stem cell, at a specific "safe harbor" locations in the human genome. Such techniques, in combination with the stem cells of the invention, can be used in gene therapy, including treatments based on autologous stem cell transplantation, where one or more genes of the cloned (diseased or normal) stem cells are manipulated to increase or decrease/eliminate a target gene expression.

Alternatively, CRISPR/Cas system can also be used to efficiently induce targeted genetic alterations into the subject stem cells. CRISPR/Cas (CRISPR associated) systems or "Clustered Regulatory Interspaced Short Palindromic Repeats" are loci that contain multiple short direct repeats, and provide acquired immunity to bacteria and archaea. CRISPR systems rely on crRNA and tracrRNA for sequence-specific silencing of invading foreign DNA. The term "tracrRNA" stands for trans-activating chimeric RNA, which is noncoding RNA that promotes crRNA processing, and is required for activating RNA-guided cleavage by Cas9. CRISPR RNA or crRNA base pairs with tracrRNA to form a two-RNA structure that guides the Cas9 endonuclease to complementary DNA sites for cleavage.

Three types of CRISPR/Cas systems exist: in type II systems, Cas9 serves as an RNA-guided DNA endonuclease that cleaves DNA upon crRNA-tracrRNA target recognition. In bacteria, the CRISPR system provides acquired immunity against invading foreign DNA via RNA-guided DNA cleavage. The CRISPR/Cas system can be retargeted to cleave virtually any DNA sequence by redesigning the crRNA. Indeed, the CRISPR/Cas system has been shown to be directly portable to human cells by co-delivery of plasmids expressing the Cas9 endonuclease and the necessary crRNA components. These programmable RNA-guided DNA endonucleases have demonstrated multiplexed gene disruption capabilities and targeted integration in iPS cells, and can thus be used similarly in the subject stem cells.

Cancer Stem Cells

The methods and reagents of the invention also enable culturing and isolating cancer-derived cancer stem cells (CSCs) from epithelial tissue samples/biopsies or from other columnar regenerative tissues, which in turn may be used in numerous applications previously impossible or impractical to carry out, partly due to the inability to obtaining such CSCs in large quantity and as single cell clones.

For example, the libraries of CSCs established from a single patient using the methods of the invention enable comparison between patient-matched sensitive and resistant clones for directed drug discovery efforts. Certain genes may be up-regulated or down-regulated in the resistant clones compared to the sensitive clones. Inhibitors for the up-regulated genes may be further validated as a drug target gene, by testing, for example, the ability of down-regulation of the target gene in the resistant clones, and determining its effect on drug resistance. Conversely, restoring or overexpressing the down-regulated genes in the resistant clones may also overcome drug resistance.

Thus in one aspect, the invention provides a drug discovery method using CSCs isolated using the subject methods and media, for identifying genes up- or down-regulated in drug resistant CSC clones, the method comprising: (1) using the method of the invention, obtaining a plurality of cell clones from a cancerous tissue (such as one from a cancer patient); (2) contacting the plurality of cell clones with one or more chemical compound (e.g., cancer drug), under conditions in which a small percentage (e.g., no more than 1%, 0.5%, 0.2%, 0.1%, 0.05%, 0.01% or fewer) of drug-resistant clones survive; (3) comparing gene expression profiles of the drug-resistant clones with that of the sensitive clones (e.g., one or more randomly picked plurality of cell clones before step (2), which are presumably sensitive to drug treatment), thus identifying genes up- or down-regulated in the surviving drug-resistant clones.

In certain embodiments, the method further comprises inhibiting the expression of an up-regulated gene in the surviving drug-resistant clone. For example, the up-regulated gene may be commonly up-regulated in two or more surviving drug-resistant clones, either from the same type of tumors or different types of tumors, either from the same patient, or from different patients. In certain embodiments, the up-regulated gene may be specific for the patient from whom the CSCs are isolated. This can be helpful in designing personalized medicine or treatment regimens for the patient.

In certain embodiments, the method further comprises restoring or increasing the expression of a down-regulated gene in the surviving drug-resistant clone. For example, the down-regulated gene may be commonly down-regulated in two or more surviving drug-resistant clones, either from the same type of tumors or different types of tumors, either from the same patient, or from different patients. In certain embodiments, the down-regulated gene may be specific for the patient from whom the CSCs are isolated. This can also be helpful in designing personalized medicine or treatment regimens for the patient.

In a related aspect, the invention provides a drug discovery method using CSCs isolated using the subject methods and media, for identifying a candidate compound that inhibit the growth or promote the killing of a drug-resistant CSC, the method comprising: (1) using the method of the invention, obtaining a plurality of cell clones from a cancerous tissue (such as one from a cancer patient); (2) contacting the plurality of cell clones with one or more chemical compound (e.g., cancer drug), under conditions in which a small percentage (e.g., no more than 1%, 0.5%, 0.2%, 0.1%, 0.05%, 0.01% or fewer) of drug-resistant clones survive; (3) contacting the surviving drug-resistant clones with a plurality of candidate compounds, and (4) identifying one or more candidate compounds that inhibit the growth or promote the killing of the surviving drug-resistant clones. In certain embodiments, the method is performed using high-throughput screens format, for candidate drugs that target resistant cells.

In certain embodiments, the method further comprises testing general toxicity of the identified candidate compounds on the matching sensitive clones (e.g., one or more randomly picked plurality of cell clones before step (2), which are presumably sensitive to drug treatment), and/or the matching healthy cells from the same patient from whom the CSCs are isolated. Preferably, any identified candidate compounds specifically or preferentially inhibit the growth or promote the killing of the drug-resistant CSC, compared to the matching sensitive clones and/or the matching healthy cells.

In certain embodiments, the healthy cells are patient-matched normal stem cells similarly isolated using the methods and reagents of the invention.

The above embodiment is partly based on the discovery that, in many cases, drug-resistant CSCs grow more slowly compared to drug-sensitive clones. While not wishing to be bound by any particular theory, Applicant believes that the slow growth is likely a consequence of gene expression alterations in the drug-resistant CSCs for evading chemotherapy. Thus, it is expected that certain agents may inhibit the growth or kill drug resistant cells preferentially while being less toxic than standard chemotherapy drugs (such as cisplatin or paclitaxel) used to treat the cancer in the first place.

In another aspect, the invention provides a method for identifying a suitable or effective treatment for a patient in need of treating a disease, the method comprising: (1) using the method of the invention, obtaining a plurality of stem cell clones from a disease tissue (such as a cancerous tissue) from the patient; (2) subjecting the plurality of cell clones to one or more candidate treatments; (3) determining the effectiveness of each of said one or more candidate treatments; thereby identifying a suitable or effective treatment for the patient in need of treating the disease. This can be useful, for example, when the patient has several possible treatment options, each may or may not be suitable or effective for the patient.

In a related aspect, the invention provides a method for screening for the most suitable or effective treatment among a plurality of candidate treatments, for treating a patient in need of treating a disease, the method comprising: (1) using the method of the invention, obtaining a plurality of stem cell clones from a disease tissue (such as a cancerous tissue) from the patient; (2) subjecting the plurality of cell clones to said candidate treatments; (3) comparing the relative effectiveness of said one or more candidate treatments; thereby identifying the most suitable or effective treatment for the patient. This can be useful, for example, when the patient has several alternative treatment options that may each be effective against a specific patient population but not necessarily effective for others.

In certain embodiments, the disease is a cancer, such as any of the cancers from which a cancer stem cell can be isolated.

In certain embodiments, the treatment is a chemotherapy regimen, such as one utilizing one or more chemo therapeutic agents. In certain embodiments, the treatment is radiotherapy. In certain embodiments, the treatment is immunotherapy, such as one using a cell-binding agent (e.g., antibody) that specifically binds to a surface ligand (e.g., surface antigen) of a cancer cell. In certain embodiments, the treatment is a combination therapy of surgery, chemotherapy, radiotherapy, and/or immunotherapy.

In certain embodiments, the disease is an inflammatory disease, a disease from which a disease-associated stem cell can be isolated, or any disease referenced herein.

In certain embodiments, the method further comprises treating the patient using one or more identified suitable or effective treatment for the disease.

In certain embodiments, the method further comprises producing a report that provides the effectiveness of each of said candidate treatments, such as the effectiveness of each of the candidate chemotherapeutic agents tested, either individually or in combination (including sequentially or simultaneously).

In certain embodiments, the method further comprises providing a recommendation for the most effective treatment.

In a related aspect, the invention provides kits and reagents for carrying out the methods of the invention.

In certain embodiments, the general screening method of the invention (not necessarily limited to cancer stem cells) is carried out in high-throughput/automatic fashion. For high-throughput purposes, the expanded stem cell population can be cultured in multiwell plates such as, for example, 96-well plates or 384-well plates. Libraries of molecules are used to identify a molecule that affects the plated stem cells. Preferred libraries include (without limitation) antibody fragment libraries, peptide phage display libraries, peptide libraries (e.g., LOPAP™, Sigma Aldrich), lipid libraries (BioMol), synthetic compound libraries (e.g., LOP AC™, Sigma Aldrich) or natural compound libraries (Specs, TimTec). Furthermore, genetic libraries can be used that induce or repress the expression of one of more genes in the progeny of the stem cells. These genetic libraries comprise cDNA libraries, antisense libraries, and siRNA or other non-coding RNA libraries.

The stem cells are preferably exposed to multiple concentrations of a test/candidate agent for a certain period of time. At the end of the exposure period, the cultures are evaluated for a pre-determined effect, such as any changes in a cell, including, but not limited to, a reduction in, or loss of, proliferation, a morphological change, and cell death.

The expanded stem cell population can also be used to identify drugs that specifically target epithelial carcinoma cells or stem cells isolated therefrom, but not the expanded stem cell population itself.

The ready cloning of cancer stem cells also enables immunological approaches to tumor destruction. The technology described herein enables the high-efficiency cloning of CSCs and therefore potentially provides information that would aid approaches to eradicating these cells via immune activation.

For example, upon isolating the CSCs (either drug-sensitive or drug-resistant), one or more epitopes of such CSCs, preferably CSC-specific epitopes compared to healthy control (e.g., epitopes on the cell surface or secretome of CSCs), may be used to vaccinate antigen-presenting cells (APCs) to direct lymphocytes to target these CSCs. The immunological approaches might include, as was done to melanoma, the identification and targeting of molecules on the cell surface or secretome of CSCs that suppress immune surveillance.

Regenerative Medicine

The subject stem cells may also be useful in regenerative medicine, for example in post-trauma, post-radiation, and/or post-surgery repair of the various damaged reproductive tissues or organs.

In yet another embodiment, a small biopsy or tissue sample can be taken from adult donors, and stem cells therein can be isolated and expanded, and optionally differentiated, to generate transplantable epithelium for regenerative purposes. The fact that the subject stem cells can be frozen and thawed and put back into culture without losing the stem cell character and without significant cell death further adds to the applicability of the subject stem cells for transplantation purposes.

Thus, the invention provides a stem cell or expanded clone thereof or differentiation product thereof (or collectively "stem cell" in the context of regenerative medicinal use) for use in transplantation into a mammal, preferably into a human. Also provided is a method of treating a patient in need of a transplant comprising transplanting a population of the stem cell of the invention into the patient, wherein the patient is a mammal, preferably a human.

Thus, another aspect of the invention provides a method of treating a human or non-human animal patient through cellular therapy. Such cellular therapy encompasses the application or administration of the stem cells of the invention (such as tissue matched stem cells of the invention) to the patient through any appropriate means. Specifically, such methods of treatment involve the regeneration of damaged tissue or wound healing. In accordance with the invention, a patient can be treated with allogeneic or autologous stem cells or clonal expansion thereof. "Autologous" cells are cells which originated from the same organism into which they are being re-introduced for cellular therapy, for example in order to permit tissue regeneration. However, the cells have not necessarily been isolated from the same tissue as the tissue they are being introduced into. An autologous cell does not require matching to the patient in order to overcome the problems of rejection. "Allogeneic" cells are cells which originated from an individual which is different from the individual into which the cells are being introduced for cellular therapy, for example in order to permit tissue regeneration, although of the same species. Some degree of patient matching may still be required to prevent the problems of rejection.

Generally, the stem cells of the invention are introduced into the body of the patient by injection or implantation. Generally, the cells will be directly injected into the tissue in which they are intended to act. Alternatively, the cells will be injected through the portal vein. A syringe containing cells of the invention and a pharmaceutically acceptable carrier is included within the scope of the invention. A catheter attached to a syringe containing cells of the invention and a pharmaceutically acceptable carrier is also included within the scope of the invention.

Stem cells of the invention can also be used in the regeneration of tissue. In order to achieve this function, cells may be injected or implanted directly into the damaged tissue, where they may multiply and eventually differentiate into the required cell type, in accordance with their location in the body, and/or after homing to their tissue of origin.

Alternatively, the subject stem cells can be injected or implanted directly into the damaged tissue. Tissues that are susceptible to treatment include all damaged tissues, particularly including those which may have been damaged by disease, injury, trauma, an autoimmune reaction, or by a viral or bacterial infection. In some embodiments of the invention, the stem cells of the invention are used to regenerate the lung, esophagus, stomach, small intestine, colon, intestinal metaplasia, fallopian tube, kidney, pancreas, bladder, liver, or gastric system, or a portion/section thereof.

In certain embodiments, the patient is a human, but may alternatively be a non-human mammal, such as a cat, dog, horse, cow, pig, sheep, rabbit or mouse.

In certain embodiments, the stem cells of the invention are injected into a patient using a syringe, such as a Hamilton syringe. The skilled person will be aware what the appropriate dosage of stem cells of the invention will be for a particular condition to be treated.

In certain embodiments, the stem cells of the invention, either in solution, in microspheres, or in microparticles of a variety of compositions, are administered into the artery irrigating the tissue or the part of the damaged organ in need of regeneration.

Generally, such administration will be performed using a catheter. The catheter may be one of the large variety of balloon catheters used for angioplasty and/or cell delivery or a catheter designed for the specific purpose of delivering the cells to a particular local of the body.

For certain uses, the stem cells may be encapsulated into microspheres made of a number of different biodegradable compounds, and with a diameter of about 15 µm.

This method may allow intravascularly administered stem cells to remain at the site of damage, and not to go through the capillary network and into the systemic circulation in the first passage. The retention at the arterial side of the capillary network may also facilitate their translocation into the extravascular space.

In certain embodiments, the stem cells may be retrograde injected into the vascular tree, either through a vein to deliver them to the whole body or locally into the particular vein that drains into the tissue or body part to which the stem cells are directed.

In another embodiment, the stem cells of the invention may be implanted into the damaged tissue adhered to a biocompatible implant. Within this embodiment, the cells may be adhered to the biocompatible implant in vitro, prior to implantation into the patient. As will be clear to a person skilled in the art, any one of a number of adherents may be used to adhere the cells to the implant, prior to implantation. By way of example only, such adherents may include fibrin, one or more members of the integrin family, one or more members of the cadherin family, one or more members of the selectin family, one or more cell adhesion molecules (CAMs), one or more of the immunoglobulin family and one or more artificial adherents. This list is provided by way of illustration only, and is not intended to be limiting. It will be clear to a person skilled in the art, that any combination of one or more adherents may be used.

In another embodiment, the stem cells of the invention may be embedded in a matrix, prior to implantation of the matrix into the patient. Generally, the matrix will be implanted into the damaged tissue of the patient. Examples of matrices include collagen based matrices, fibrin based matrices, laminin based matrices, fibronectin based matrices and artificial matrices. This list is provided by way of illustration only, and is not intended to be limiting. In a further embodiment, the stem cells of the invention may be implanted or injected into the patient together with a matrix forming component. This may allow the cells to form a matrix following injection or implantation, ensuring that the stem cells remain at the appropriate location within the patient. Examples of matrix forming components include fibrin glue liquid alkyl, cyanoacrylate monomers, plasticizers, polysaccharides such as dextran, ethylene oxide-containing oligomers, block co-polymers such as poloxamer and Pluronics, non-ionic surfactants such as Tween and Triton 8, and artificial matrix forming components. This list is provided by way of illustration only, and is not intended to be limiting. It will be clear to a person skilled in the art, that any combination of one or more matrix forming components may be used.

In a further embodiment, the stem cells of the invention may be contained within a microsphere. Within this embodiment, the cells may be encapsulated within the center of the microsphere. Also within this embodiment, the cells may be embedded into the matrix material of the microsphere. The matrix material may include any suitable biodegradable polymer, including but not limited to alginates, Poly ethylene glycol (PLGA), and polyurethanes. This list is provided by way of example only, and is not intended to be limiting.

In a further embodiment, the stem cells of the invention may be adhered to a medical device intended for implantation. Examples of such medical devices include stents, pins, stitches, splits, pacemakers, prosthetic joints, artificial skin, and rods. This list is provided by way of illustration only, and is not intended to be limiting. It will be clear to a person skilled in the art, that the cells may be adhered to the medical device by a variety of methods. For example, the stem cells may be adhered to the medical device using fibrin, one or more members of the integrin family, one or more members of the cadherin family, one or more members of the selectin family, one or more cell adhesion molecules (CAMs), one or more of the immunoglobulin family and one or more artificial adherents. This list is provided by way of illustration only, and is not intended to be limiting. It will be clear to a person skilled in the art, that any combination of one or more adherents may be used.

Accordingly, included within the scope of the invention are methods of treatment of a human or animal patient through cellular therapy. The term "animal" here denotes all mammalian animals, preferably human patients. It also includes an individual animal in all stages of development, including embryonic and fetal stages. For example, the patient may be an adult, or the therapy may be for pediatric use (e.g., newborn, child or adolescent). Such cellular therapy encompasses the administration of stem cells generated according to the invention to a patient through any appropriate means. Specifically, such methods of treatment involve the regeneration of damaged tissue or wound healing. The term "administration" as used herein refers to well recognized forms of administration, such as intravenous or injection, as well as to administration by transplantation, for example transplantation by surgery, grafting or transplantation of tissue engineered liver derived from the stem cells according to the present invention. In the case of cells, systemic administration to an individual may be possible, for example, by infusion into the superior mesenteric artery, the celiac artery, the subclavian vein via the thoracic duct, infusion into the heart via the superior vena cava, or infusion into the peritoneal cavity with subsequent migration of cells via subdiaphragmatic lymphatics, or directly into liver sites via infusion into the hepatic arterial blood supply or into the portal vein.

Between $10^4$ and $10^{13}$ cells per 100 kg person may be administered per infusion. Preferably, between about $1-5 \times 10^4$ and $1-5 \times 10^7$ cells may be infused intravenously per 100 kg person. More preferably, between about $1 \times 10^4$ and $1 \times 10^6$ cells may be infused intravenously per 100 kg person. In some embodiments, a single administration of the subject stem cells is provided. In other embodiments, multiple administrations are used. Multiple administrations can be provided over an initial treatment regime, for example, of 3-7 consecutive days, and then repeated at other times.

It will be clear to a skilled person that gene therapy can additionally be used in a method directed at repairing damaged or diseased tissue. Use can, for example, be made of an adenoviral or retroviral gene delivery vehicle to deliver genetic information, like DNA and/or RNA to stem cells. A skilled person can replace or repair particular genes targeted in gene therapy. For example, a normal gene may be inserted into a nonspecific location within the genome to replace a nonfunctional gene. In another example, an abnormal gene sequence can be replaced for a normal gene sequence through homologous recombination. Alternatively, selective reverse mutation can return a gene to its normal function. A further example is altering the regulation (the degree to which a gene is turned on or off) of a particular gene. Preferably, the stem cells are ex vivo treated by a gene therapy approach and are subsequently transferred to the mammal, preferably a human being in need of treatment. For example, stem cell-derived cells may be genetically modified in culture before transplantation into patients.

Toxicity Assay

The expanded stem cell population can further replace the use of cell lines such as Caco-2 cells in toxicity assays of potential novel drugs or of known or novel food supplements. Such toxicity assay may be conducted using patient matched or tissue/organ matched stem cells, which may be useful in personalized medicine.

A cell-based toxicity test is used for determining organ specific cytotoxicity.

Compounds that may be tested comprise cancer chemopreventive agents, environmental chemicals, food supplements, and potential toxicants. The cells are exposed to multiple concentrations of a test agent for certain period of time. The concentration ranges for test agents in the assay are determined in a preliminary assay using an exposure of five days and log dilutions from the highest soluble concentration. At the end of the exposure period, the cultures are evaluated for inhibition of growth. Data are analyzed to determine the concentration that inhibited end point by 50 percent (TC50).

For high-throughput purposes, epithelial stem cells are cultured in multiwell plates such as, for example, 96-well plates or 384-well plates. Libraries of molecules are used to identify a molecule that affects the stem cells. Preferred libraries comprise antibody fragment libraries, peptide phage display libraries, peptide libraries (e.g., LOPAP™ Sigma Aldrich), lipid libraries (BioMol), synthetic compound libraries (e.g., LOPAC™, Sigma Aldrich) or natural compound libraries (Specs, TimTec). Furthermore, genetic libraries can be used that induce or repress the expression of one of more genes in the progeny of the adenoma cells. These genetic libraries comprise cDNA libraries, antisense libraries, and siRNA or other non-coding RNA libraries. The cells are preferably exposed to multiple concentrations of a test agent for certain period of time. At the end of the exposure period, the cultures are evaluated. The term "affecting" is used to cover any change in a cell, including, but not limited to, a reduction in, or loss of, proliferation, a morphological change, and cell death.

Animal Model

Another aspect of the invention provides an animal model comprising a subject stem cell, such as a subject cancer stem cell.

In certain embodiments, the animal is an immunodeficient non-human animal (such as a rodent, e.g., a mouse or a rat), since such animal is less likely to cause rejection reaction. As an immunodeficient animal, it is preferred to use a non-human animal deficient in functional T cells, such as a nude mouse and rat, and a non-human animal deficient in functional T and B cells, such as a SCID mouse and a NOD-SCID mouse. Particularly, a mouse deficient in T, B, and NK cells (for example, a severely immunodeficient mouse obtained by crossing a SCID, RAG2KO, or RAG1KO mouse with an IL-2Rgnu11 mouse, which includes NOD/SCID/gammacnu11 mouse, NOD-scid, IL-2Rgnu11 mouse, and BALB/c-Rag2nu11, IL-2Rgnu11 mouse), which shows excellent transplantability, is preferably used.

Regarding the age of non-human animals, when athymic nude mice, SCID mice, NOD/SCID mice, or NOG mice are used, those of 4-100 weeks old are preferably used.

NOG mice can be produced, for example, by the method described in WO 2002/043477 (incorporated by reference), or can be obtained from the Central Institute for Experimental Animals or the Jackson Laboratory (NSG mice).

Cells to be transplanted may be any types of cells, including a stem cell mass/clone, a tissue section differentiated from the subject stem cell, singly dispersed stem cells, stem cells cultured after isolation or freeze/thaw, and stem cells transplanted to another animal and again isolated from the animal. The number of cells to be transplanted may be $10^6$ or less, but a greater number of cells may be transplanted. In certain embodiments, subcutaneous transplantation is preferable because of its simple transplantation techniques. However, the site of transplantation is not particularly limited and preferably appropriately selected depending on the animal used. The procedure for transplanting NOG established cancer cell lines is not particularly limited, and any conventional transplantation procedures can be used.

Such animal models can be used to, for example, search for drug target molecules and to assess drugs. Assessment methods for drugs include screening for drugs and screening for anticancer agents. Methods of searching for target molecules include, but are not limited to, methods for identifying genes such as DNAs and RNAs highly expressed in cancer stem cells (e.g., cancer stem cell markers) using Gene-chip analysis, and methods for identifying proteins, peptides, or metabolites highly expressed in cancer stem cells using proteomics.

Screening methods for searching for target molecules include methods in which substances that inhibit the growth of cancer stem cells are screened from a small molecule library, antibody library, micro RNA library, or RNAi library, etc., using cell growth inhibition assay. After an inhibitor is obtained, its target can be revealed.

Thus the invention also provides a method of identifying a target molecule of a drug, the method comprising: (1) producing a non-human animal model by transplanting a cancer stem cell of the invention to a non-human animal (e.g., an immuno-compromised mouse or rat); (2) before and after administering the drug, collecting a tissue section showing a tissue structure characteristic of a cancer development process of said cancer stem cell population or showing a biological property thereof; (3) examining/comparing the tissue sections (before vs. after) collected in (2) for the expression of a DNA, RNA, protein, peptide, or metabolite; and (4) identifying a DNA, RNA, protein, peptide or metabolite that varies depending on a structure formed from the cancer stem cells, a cancer development process originating from the cancer stem cells, or a biological property of the cancer stem cells, in the tissue section.

The invention also provides a method of assessing a drug, the method comprising: (1) producing a non-human animal model by transplanting a cancer stem cell of the invention to a non-human animal (e.g., an immuno-compromised mouse or rat); (2) administering a test substance to the non-human animal model of (1); (3) collecting a tissue section showing a tissue structure characteristic of a cancer development process originating from cancer stem cells or showing a biological property thereof; (4) observing a change in the cancer stem cells over time, cancer development process, or a biological property thereof, in the tissue section; and (5) identifying formation of a structure formed from the cancer stem cells, a cancer development process originating from the cancer stem cells, or a biological property of the cancer stem cells, that is inhibited by the test substance.

The invention also provides a method of screening for a drug, the method comprising: (1) producing a non-human animal model by transplanting a cancer stem cell of the invention to a non-human animal (e.g., an immuno-compromised mouse or rat); (2) administering a test substance to the non-human animal model of (1); (3) collecting a tissue section that shows a tissue structure characteristic of a cancer development process originating from cancer stem cells, or shows a biological property thereof; (4) observing a change in the cancer stem cells over time, cancer development process, or a biological property thereof, in the tissue section; and (5) identifying a test substance that inhibits formation of a structure formed from specific cancer stem cells, a cancer development process originating from cancer stem cells, or a biological property of cancer stem cells.

8. Illustrative Example

The medium described herein has been tested and proven to support robust growth of epithelial stem cells derived from columnar epithelial tissues from human and other mammals. For example, colon stem cells have been cloned (see FIGS. 1, 2, 3A and 3B).

A. MGM Medium

An illustrative system is a medium referred to as MGM. The MGM medium has been tested and proven to support robust growth of epithelial stem cells derived from human tissues or other mammals. For example, columnar lung stem cells, esophagus stem cell, gastrointestinal stem cells, cancer stem cells, liver stem cells, pancreas stem cells can all grow robustly in this culture system that comprises MGM medium, along with irradiated 3T3-J2 feeders in the illustrated example.

The MGM media begins with a basal medium as follows:
Per 1 L of Media

| | |
|---|---|
| DMEM | 645 ml |
| F12 | 215 ml |
| FBS | 100 ml |
| L-glutamine | 10 ml |
| Adenine | 10 ml |
| Pen/Strep | 10 ml |
| Insulin | 1 ml |
| T3 | 1 ml |
| Hydrocortisone | 2 ml |
| Cholera Enterotoxin | 1 ml |
| EGF | 1 ml |
| Gentamicin | 5 ml |
| Fungizone | 1 ml |

Additional Components:

1: R-Spondin 1

(Cat. 4645-RS, R&D; Final concentration: 125 ng/ml, stock: 25 ug/vial)

2: AV-951

(Cat. S1207, Selleckchem Inc; Final concentration: 500 nM, stock: 10 mM)

3: GDC-0879

(Cat. S1104, Selleckchem Inc; Final concentration: 500 nM, stock: 10 mM)

3: Human Noggin (Cat. 120-10c, Peprotech; Final concentration: 100 ng/ml, stock: 100 ug/ml) (Dissolve 500 ug in 5 ml H2O as stock)

4: ROCK-inhibitor
(Cat. 688000, Calbiochem; Final concentration: 2.5 uM, stock: 2.5 mM) (Dissolve 5 mg in 5.912 ml H2O as stock)

5: SB431542
(Cat. 13031, Cayman chemical company; Final concentration: 2 uM, stock 2 mM)
(Dissolve 5 mg in 6.5 ml DMSO as stock)

6: Nicotinamide
(Sigma, Cat. N0636-100G; Final concentration: 10 mM, stock: 5M)
(Dissolve 6 g in 10 ml H2O as stock)

7: GSK429286A
(Cat. S1474, Selleckchem Inc; Final concentration: 500 nM, stock: 10 mM)
Filter and store at 4° C.

Epithelial stem cells from a variety of different tissues, including lung and cervix, have been passaged in SAM medium for more than twenty-five passages and maintain self-renewal ability and multi-potent differentiation ability both in vitro and in xenograft model using NSG mice.

Filter and store at 4° C.

B. SGM-88+Feeder-Free System

An illustrative feeder-free system is a medium referred to as SGM-88+. The SGM-88+medium has been tested and proven to support robust growth of epithelial stem cells derived from human tissues or other mammals without the need for co-cultured feeder cells. It is generated as above, with the addition of components 8-11 below:

SGM-88+Medium (1 Liter)
DMEM: 645 ml
F12: 215 ml
FBS: 100 ml
L-glutamine: 10 ml
Adenine: 10 ml
Pen/Strep: 10 ml
Insulin: 1 ml
T3: 1 ml
Hydrocortisone: 2 ml
Cholera Enterotoxin: 1 ml
EGF: 1 ml
Gentamicin: 5 ml
Fungizone: 1 ml
Additional Components:

1: R-Spondin 1
(Cat. 4645-RS, R&D; Final concentration: 125 ng/ml, stock: 25 ug/vial)

2: AV-951
(Cat. S1207, Selleckchem Inc; Final concentration: 500 nM, stock: 10 mM)

3: GDC-0879
(Cat. S1104, Selleckchem Inc; Final concentration: 500 nM, stock: 10 mM)

3: Human Noggin
(Cat. 120-10c, Peprotech; Final concentration: 100 ng/ml, stock: 100 ug/ml)
(Dissolve 500 ug in 5 ml H2O as stock)

4: Y-27632
(Cat. 688000, Calbiochem; Final concentration: 2.5 uM, stock: 2.5 mM)
(Dissolve 5 mg in 5.912 ml H2O as stock)

5: SB431542
(Cat. 13031, Cayman chemical company; Final concentration: 2 uM, stock 2 mM)
(Dissolve 5 mg in 6.5 ml DMSO as stock)

6: Nicotinamide
(Sigma, Cat. N0636-100G; Final concentration: 10 mM, stock: 5M)
(Dissolve 6 g in 10 ml H2O as stock)

7: GSK429286A
(Cat. S1474, Selleckchem Inc; Final concentration: 250 nM, stock: 10 mM)

8: CP673451 (Cat. S1536, Selleckchem Inc; Final concentration: 1 microM, stock: 10 mM)

9. OAC1 (Cat. S7217, Selleckchem Inc; Final concentration: 1 microM, stock: 10 mM)

10. JNK-IN-8 (Selleckchem Inc; Final concentration: 1 microM. Stock: 10 mM)

11. Jagged-1 (Cat. 61298, AnaSpec Inc; Final concentration: 1 uM, stock: 1 mg/vial)

Filter and store at 4° C.

Components Preparation

DMEM (Invitrogen 11960)
High glucose (4.5 g/L), no L-glutamine, no sodium pyruvate
F-12 NUTRIENT MIXTURE (HAM) (Invitrogen 11765)
Contains L-glutamine
ADENINE (Calbiochem 1152 10 g)
Add 243 mg of adenine to 100 ml of 0.05M HCl (dilute 0.4 ml of concentrated HCl in 100 ml of distilled H$_2$O)
Stir for about one hour at RT to dissolve
Filter sterilize
Divide into 10.0 ml aliquots
Final Concentration: $1.8 \times 10^{-4}$M
Store at −20° C.
FBS (Hyclone SH30910.03 500 mL)
DO NOT heat inactivate serum
Thaw and aliquot serum into 50 ml/tube and store at −20° C.
L-GLUTAMINE (GIBCO 25030-081 100 ml)
Thaw and divide into 10.0 ml aliquots
Store at −20° C.
PENICILLIN/STREPTOMYCIN (GIBCO 15140-122 100 mL)
Fungizone (Gibco, 15290-018)
Gentamicine (Gibco, 15710-064),
INSULIN (Sigma I-5500 50 mg)
Dissolve 50 mg in 10 ml of 0.005N HCl (stock 5 mg/ml)
Distribute in 1 ml aliquots and store at −20° C.
Final concentration 5 ug/ml
T3 (3,3',5-Triiodo-L-Thyronine) (Sigma T-2752 100 mg)
Dissolve 13.6 mg in 15 ml of 0.02N NaOH
Make volume up to 100 ml with PBS (concentrated stock $2 \times 10^{-4}$M)
Distribute in 10 ml aliquots and store at −20° C.
Take 0.1 ml concentrated stock, make volume up to 10 ml with PBS
Distribute in 1 ml aliquots and store at −20° C. (stock $2 \times 10^{-6}$M)
Final concentration $2 \times 10^{-9}$M
HYDROCORTISONE (Sigma H-0888 1 g or Calbiochem/EMD 386698)
Dissolve 25 mg in 5 ml 95% ETOH (concentrated stock 5 mg/ml)
Store at −20° C.
Take 0.4 ml of concentrated stock, make up to 10 ml with serum-free SBM medium
Distribute in 1 ml aliquots and store at −20° C. (stock 200 μg/ml)
Final concentration 0.4 ug/ml
CHOLERA ENTEROTOXIN
(MP Biomedicals 190329 1 mg or Calbiochem/EMD 227036)
Dissolve 1 mg (1 vial) in 1.18 ml distilled H$_2$O (concentrated stock $10^{-5}$M)
Store at 4° C.-DO NOT FREEZE!
Add 0.1 ml of concentrated stock to 10 ml SBM medium containing 10% FBS
Distribute in 1 ml aliquots and store at −20° C. (stock $10^{-7}$M)
Final concentration $10^{-10}$M
EGF (Upstate Biotechnology 01-107)
PREPARATION OF 0.1% BSA:
100 mg BSA (Sigma A-2058; IgG-free, cell culture tested 5 g)
Dissolve in 100 ml distilled H$_2$O
Sterile filter through 0.22μ Nalgene
Store at either 4° C. or −20° C., depending on frequency of use PREPARATION OF EGF:
Dissolve 1 mg EGF in 1 ml 0.1% BSA
Distribute in 100 µl aliquots and store at −80° C.
(concentrated stock 100 µg/100 µl)
Bring 100 µg concentrated stock to 10 ml with 0.1% BSA
Sterile filter using 0.22µ Millipore Millex-GV
Distribute in 1 ml aliquots and store at −20° C. (stock 10 µg/ml)
Final concentration 10 ng/ml C. The Stemness and Genomic Stability of Ground-State Intestinal Stem Cells are Age Independent Adult stem cells in intestinal epithelium proliferate frequently. Mutations could accumulate in normal stem cells with age. The recent technical advance in ground-state intestinal stem cell cloning and culturing provides us an opportunity of accurate assessment of age-related impact on the function and genome of these highly proliferative intestinal stem cells. Our ability of expanding single-stem-cell derived pedigrees indefinitely and robustly in vitro provides sufficient DNA to accurately carry out reliable analysis and complete genomic coverage of intestinal stem cells at the clonal level. Using exome sequencing analysis, we find that chromosome deletions, amplification, and gene mutations occur in intestinal stem cell clones derived from the older and diseased individuals. Interestingly, intestinal stem cell clones with wild-type genome were identified in all donors despite the age. These wild-type stem cells can be passaged in vitro as clones and expanded to 1 billion cells in approximately six weeks without changes in stemness demonstrated by clonogenicity and mutlipotency while maintaining stable genome. Our study suggests that wild-type stem cell clones exist in aged and diseased patient and they can be cloned and expanded in vitro with the same efficiency and stability as those derived from much younger individuals. Our result highlights the importance of screening for wild-type stem cell clones in aged or diseased patients for autologous transplantation and support the promise of adult-stem-cell based personalized medicine.

Autologous transplantation using wild-type or transgenic epidermal stem cells have been proven to be extremely successful in patients with severe burns, chronic wounds and junctional epidermolysis bullosa. Conceivably, adult stem cells derived from other regenerative tissues such as intestine can be used to restore the intestinal epithelial functions following autologous transplantation in patients with severe forms of short bowel syndrome (SBS), or those with congenital disorders or those with inflammatory bowel disease (IBD).

However, caution needs to be taken when these patient-derived adult stem cells being used for autologous transplantation. Although there is an intriguing amount of evidence suggesting that the stem cells residing in the intestinal tissues of aged people are still quite capable, it is unclear whether their stem cell behavior is similar to those taken from a younger individual. Whether old stem cells are inherently dysfunctional is a question of considerable relevance to the practical development of stem cell therapies based on autologous transplantation for people at all ages. Furthermore, accumulated cellular damage in intestinal stem cells of older patient can lead to genomic changes that can make these stem cells become premalignant or transformed (Hsieh et al., 2013, Aging Cell (2013) 12, pp269-279). Furthermore, some of the intestinal disorders such as Ulcerative Colitis (UC) have been linked with the development of colorectal cancer (O'Conor Pm et al., Bowel Dis. 16, 1411-1420). Therefore, it is concerning to utilize the aged patient or diseased patient derived intestinal stem cells for autologous transplantation without prior screening and selection of wild-type intestinal stem cells.

Cloning, screening and expanding wild-type intestinal stem cells is challenging due to a significant barrier of adult stem cell research which is our inability of cloning stem cells from columnar epithelial tissue and maintaining their immaturity during in vitro expansion. Consequently, intestinal stem cells have to be carried forward as regenerative, differentiating "organoids" with very low percentage of clonogenic cells, which limits the kinetics of their propagation as well as their utility for exploring the elemental stem cell. Recently, a new technology was developed to support cloning the ground-state intestinal stem cell (ISCGS) in their highly immature, clonogenic state. These cultured ISCGS demonstrated remarkable stability in their genome and epigenetic commitment programs, maintained clonogenicity and unlimited replicative expansion, suggesting their tremendous potential in selective culturing wild-type ISCGS for personalized regenerative medicine.

In this study, we used the ground-state stem cell cloning technology to study intestinal stem cells derived from a wide range of patients. We found that although there is an increased chance of deriving ISCGS with genetic mutations in older patient and UC patient, we are still able to clone wild-type ISCGS from them. In addition, after removed from the old cellular environments, their behavior becomes identical to those taken from a younger individual. Therefore, our study suggest that wild-type ISCGS exist in patients at all ages even under the condition of UC and they can be passaged robustly and stably in vitro, suggesting the intrinsic immortality of intestinal stem cells is age independent.

Results

ISCGS Derived from Patients with Wide-Range Age

Figure 4A:
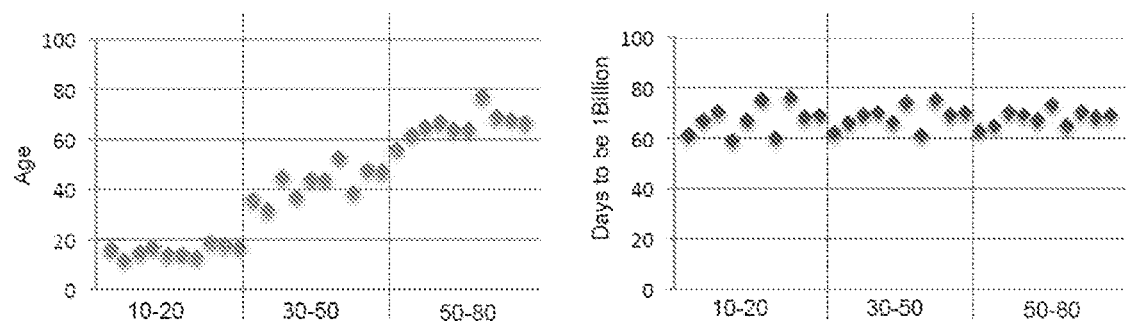
FIG. 4A: Starting from one ISCGS colony, a billion ISCGS cells can be generated from all thirty patients independent of age in approximately six days.
Figure 4B:
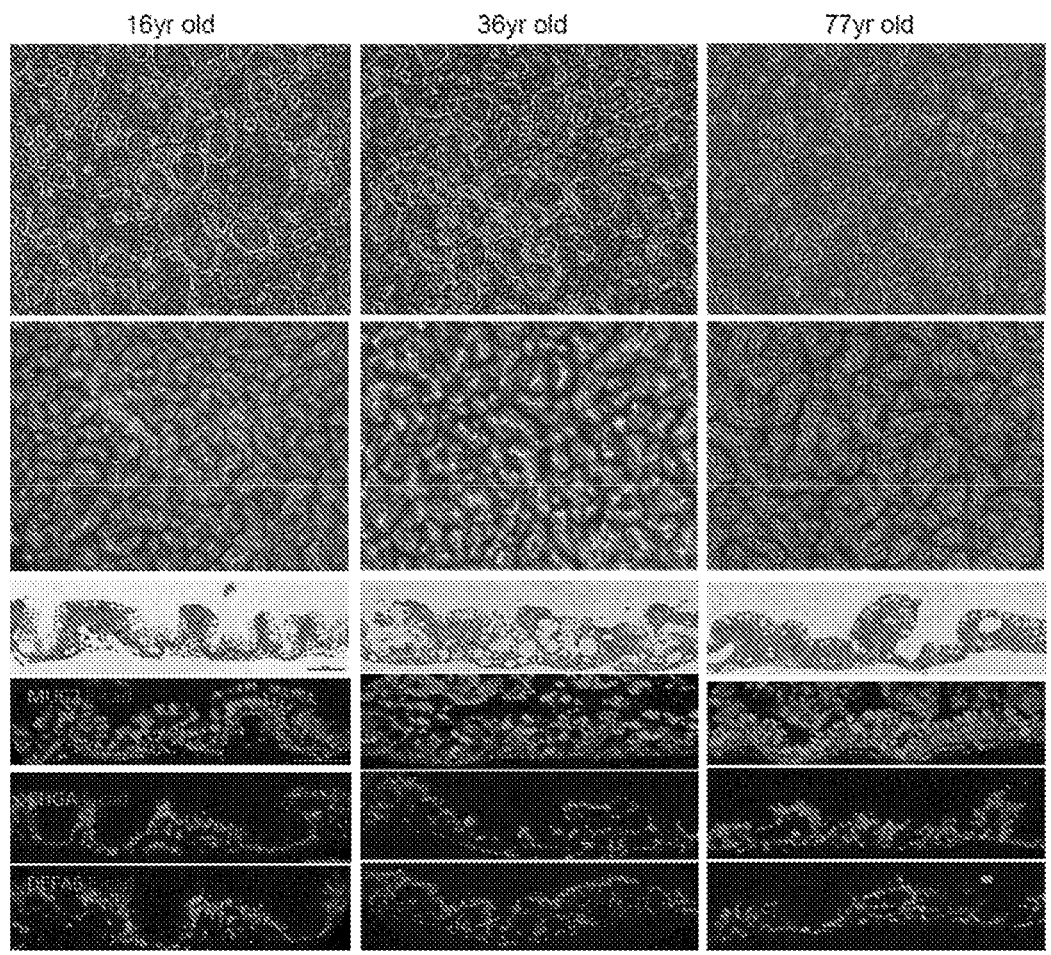
FIG. 4B: The ISCGS derived from all ages displayed indistinguishable morphology and same multipotent differentiation ability. Pedigree lines of ISCGS of 16, 56 and 77 years old patients were differentiated in air-liquid interface (ALI) cultures for 10 days.

In order to understand whether ground-state intestinal stem cells (ISCGS) can be successfully cloned and cultured from patients at all ages, we chose ten patients between age 10 to 20, ten patients between age 30 to 50 and ten patients between age 50 to 80. The 1 mm biopsies from the intestinal epithelium of these patients were enzymatic digested and seeded in a system including 3T3J2 feeder and specialized medium. We detected approximately 50 colonies can be derived from each of all thirty patients. Starting from one ISCGS colony, a billion ISCGS cells can be generated from all thirty patients independent of age in approximately six days (FIG. 4A). The ISCGS derived from all ages displayed indistinguishable morphology and same multipotent differentiation ability. Pedigree lines of ISCGS of 16, 56 and 77 years old patients were differentiated in air-liquid interface (ALI) cultures for 10 days (FIG. 4B). All the ISCGS formed a highly uniform, 3D serpentine pattern. Histological sections of these differentiated ISCGS revealed a columnar epithelium of villus-like structures marked by goblet (Mucin 2+), endocrine (chromogranin A+), and Paneth cells (defensin alpha 6+), indicating that the progeny of a single ISCGS from a wide range of patients (10-80) can give rise to all epithelial lineages typically found in the intestine.

Genomic Diversity of Cloned ISCGS

Figure 5A:
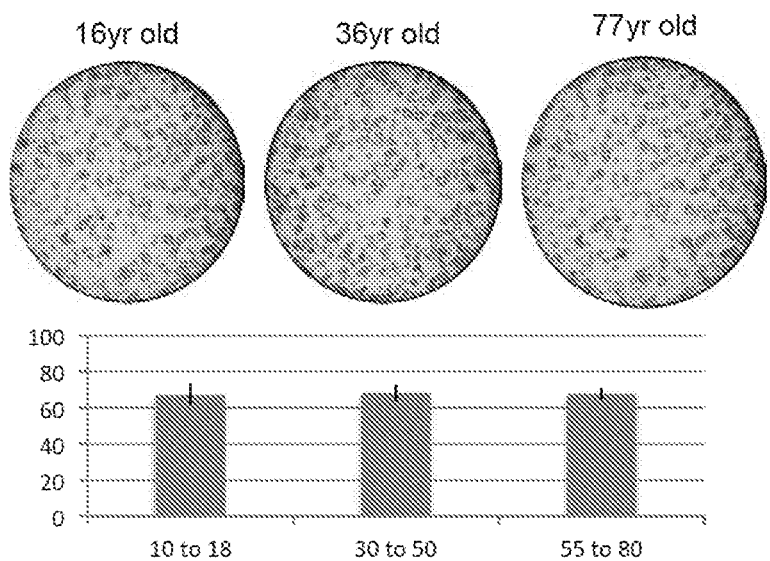
FIG. 5A: Illustrates the polyclonality in intestinal epithelium by sampling ISCGS clones from aged patients (40-70) in a copy number variation study. We first showed that ISCGS from all thirty patients are highly clonogenic. 50-70% clonogenicity was observed across the patients. Single cell derived colony can be expanded to single-cell derived pedigree including thousands of cells, which provides sufficient DNA for routine genomic analysis. We sampled between 1-23 clones from eleven adult patients with or without UC using high-density SNP arrays. We found that most of the clones showed little chromosomal changes in comparison with patient-matched blood. However, one clone out of 23 clones derived from a 44 yr old non-IBD patient showed amplifications of two putative oncogenes, SOS1 and XPO1 while the rest of the clones are all wild-type. In addition, one clone of seven clones derived from a 56 yr old UC patient showed much more significant chromosomal changes. Consequently, 16 genes are amplified including putative oncogenes such as ERBB4, ALK and MYCN.
Figure 5B:
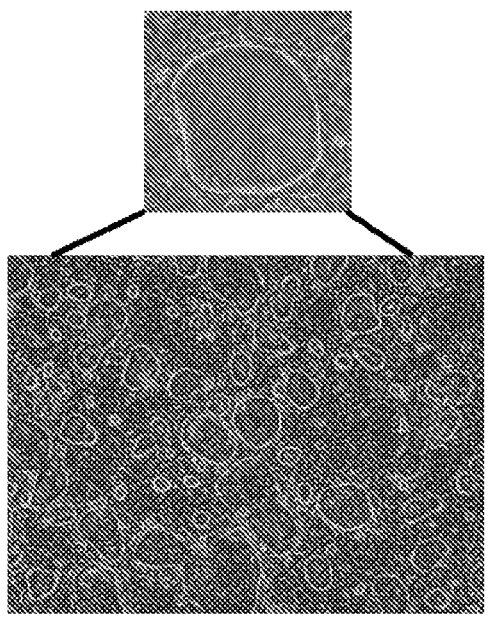
FIG. 5B: Illustrates the polyclonality in intestinal epithelium by sampling ISCGS clones from aged patients (40-70) in a copy number variation study. We first showed that ISCGS from all thirty patients are highly clonogenic. 50-70% clonogenicity was observed across the patients. Single cell derived colony can be expanded to single-cell derived pedigree including thousands of cells, which provides sufficient DNA for routine genomic analysis. We sampled between 1-23 clones from eleven adult patients with or without UC using high-density SNP arrays. We found that most of the clones showed little chromosomal changes in comparison with patient-matched blood. However, one clone out of 23 clones derived from a 44 yr old non-IBD patient showed amplifications of two putative oncogenes, SOS1 and XPO1 while the rest of the clones are all wild-type. In addition, one clone of seven clones derived from a 56 yr old UC patient showed much more significant chromosomal changes. Consequently, 16 genes are amplified including putative oncogenes such as ERBB4, ALK and MYCN.

We next want to address the polyclonality in intestinal epithelium by sampling ISCGS clones from aged patients (40-70) for copy number variation study. We first showed that ISCGS from all thirty patients are highly clonogenic. 50-70% clonogenicity was observed across the patients (FIGS. 5A and 5B). Thus, single cell derived colony can be expanded to single-cell derived pedigree including thousands of cells, which provides sufficient DNA for routine genomic analysis. We sampled between 1-23 clones from eleven adult patients with or without UC using high-density SNP arrays. We found that most of the clones showed little chromosomal changes in comparison with patient-matched blood. However, one clone out of 23 clones derived from a 44 yr old non-IBD patient showed amplifications of two putative oncogenes, SOS1 and XPO1 while the rest of the clones are all wild-type. In addition, one clone of seven clones derived from a 56 yr old UC patient showed much more significant chromosomal changes. Consequently, 16 genes are amplified including putative oncogenes such as ERBB4, ALK and MYCN. Interestingly, several other clones of the same patient displayed wild-type genome. See FIG. 5C. Our data suggest that both wild-type and mutant ISCGS can be cloned and expanded in vitro, thus preemptive elimination of mutant ISCGS is an essential step prior to their usage for autologous transplantation.

Long-Term Culturing Wild-Type ISCGS

Figure 6A:
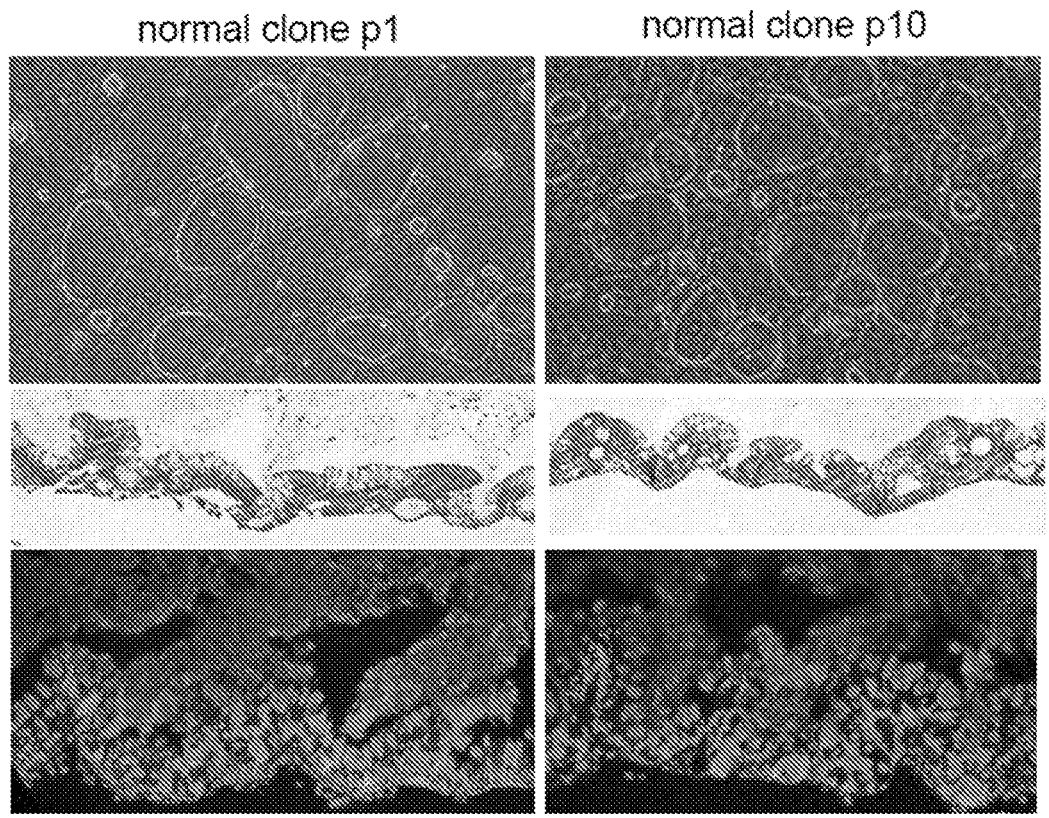
FIG. 6A: In order to investigate the genomic changes in wild-type and mutant clones derived from UC patients, we performed exome sequencing on the pool and pedigrees of ISCGS. Our genomic analysis of these cells consisted of assessing copy number variation (CNV) and point mutations using exome sequencing. We determined CNVs and point mutations using patient-matched DNA samples from mutant and wild-type pedigrees as well as pooled cells and venous blood28. Significantly, pooled ISCGS showed very low CNV in the form of interstitial deletions and amplifications. This degree of CNV in pooled stem cells was in the range of that observed in the wild-type stem cell pedigrees of the same patients.
Figure 6B:
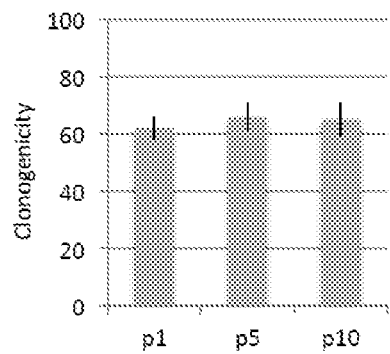
FIG. 6B: In order to investigate the genomic changes in wild-type and mutant clones derived from UC patients, we performed exome sequencing on the pool and pedigrees of ISCGS. Our genomic analysis of these cells consisted of assessing copy number variation (CNV) and point mutations using exome sequencing. We determined CNVs and point mutations using patient-matched DNA samples from mutant and wild-type pedigrees as well as pooled cells and venous blood28. Significantly, pooled ISCGS showed very low CNV in the form of interstitial deletions and amplifications. This degree of CNV in pooled stem cells was in the range of that observed in the wild-type stem cell pedigrees of the same patients.
Figure 6C:
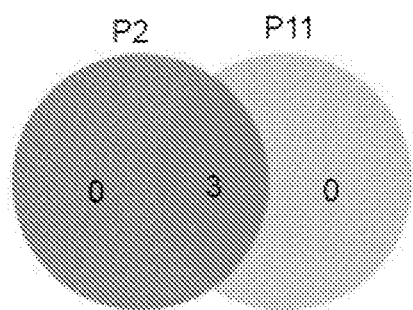
FIG. 6C: In order to investigate the genomic changes in wild-type and mutant clones derived from UC patients, we performed exome sequencing on the pool and pedigrees of ISCGS. Our genomic analysis of these cells consisted of assessing copy number variation (CNV) and point mutations using exome sequencing. We determined CNVs and point mutations using patient-matched DNA samples from mutant and wild-type pedigrees as well as pooled cells and venous blood28. Significantly, pooled ISCGS showed very low CNV in the form of interstitial deletions and amplifications. This degree of CNV in pooled stem cells was in the range of that observed in the wild-type stem cell pedigrees of the same patients.

In order to further investigate the genomic changes in wild-type and mutant clones derived from this UC patient, we performed exome sequencing on the pool and pedigrees of ISCGS. Our genomic analysis of these cells consisted of assessing copy number variation (CNV) and point mutations using exome sequencing. We determined CNVs and point mutations using patient-matched DNA samples from mutant and wild-type pedigrees as well as pooled cells and venous blood28. Significantly, pooled ISCGS showed very low CNV in the form of interstitial deletions and amplifications. This degree of CNV in pooled stem cells was in the range of that observed in the wild-type stem cell pedigrees of the same patients (FIGS. 6A, 6B and 6C). In marked contrast, the CNV in mutant stem cell pedigree showed many more interstitial deletions and amplification affecting a range of cancer-related genes such as FHIT, PTPRD, p15/p16 and ERBB4 etc. Exomes of these stem cell pedigrees had allele frequencies for point mutations clustered around 0.4-0.5 as expected for clonal populations while allele frequencies of the same point mutation is either undetectable or around 0.05 in pooled stem cells. These allele frequencies underscore the robustness of genomic analysis on stem cell pedigrees. Consistent with the CNV data, wild-type pedigrees showed no nonsynonymous mutations in comparison with the blood. Mutant pedigree showed significantly more nonsynonymous mutations at the allele frequency of 0.5 suggesting no LOH has occurred. These SNVs include Notch mutation and Ras mutation that have been implicated as drivers in carcinogenesis. Taken together, the significant higher number of events of CNV and nonsynonymous mutations in mutant clones in this Ulcerative Colitis patient suggest that the stem cells in this mutant clone are not suitable for autologous transplantation approach for this patient. Therefore, it is critical to clone wild-type stem cell clone in a polyclonal intestinal epithelium and expand them for transplantation. We next examined the genomic and functional stability of these wild-type stem cells in culture. We compared the stem cells of normal stem cell clone at early passage (p1) and late passage (p10). Each passage includes culturing in vitro for ten days with approximately 17 cell divisions. Despite passaging number, the stem cells can be differentiated properly into goblet (Muc2+), endocrine (chromogranin A+), and Paneth cells (DEFA6) and remained high clonogenic ability (above 60%). To assess the genomic stability of normal clone of ISCGS in vitro, we examined copy number variation (CNV) and single nucleotide variation (SNV) by whole exome sequencing (150× in average) in ISCGS after 100 days of continuous proliferation (FIG. 6A). At P10, when single ISCGS pedigree can be amplified to an estimated 1 billion cells, no copy number abnormality was detected. Thus, this low level of structural variation was maintained through passage 10. By comparing to blood, ISCGS pedigree demonstrated few (3) point mutations through passage 10, in which two SNPs are common variants and one SNP is synonymous mutation (FIG. 6B). No new indel and LOH event was found during passaging. These results suggest that these pedigrees sustain few genomic changes within the first 100 days of proliferative expansion. This result is consistent with what we observed in human fetal ISCGS in vitro expansion (Wang and Yamamoto et al., 2015). Thus, the stable and robust culturing of wild-type is age independent and these cells provide the safe and reliable stem cell source for personalized regenerative medicine.

Discussion

Stem cell based autologous transplantation may improve outcomes of patients with a wide range of disorders of the gastrointestinal tract, characterized by an impaired mucosal barrier function, including IBD, necrotizing enterocolitis, fistulas, NSAID-induced damage, or gastroduodenal bleeding (Hong et al., "concise review: the potential use of intestinal stem cells to treat patients with intestinal failure". Stem Cells Translational Medicine, 2017; Fredrik E O Holmberg et al., 2017; "Culturing human intestinal stem cells for regenerative applications in the treatment of inflammatory bowel disease; Mar. 10, 2017, EMBO). There are critical and unanswered questions relevant to the older or diseased patients such as whether the ISCGS derived from these individuals capable of being expanded to sufficient numbers to functionally regenerate the intestinal epithelium and whether aging or disease related genomic changes can lead to safety concerns when ISCGS are being used for therapeutic purpose.

The current direction in therapies is to use a patient's own stem cells for autologous transplantation. If aged stem cells are inherently dysfunctional, that would greatly limit the ability to use this type of therapies for older people. However, if old stem cells are still maintaining intact stemness, in other words if the intrinsic immortality of ISCGS is age independent, then this approach to regenerative medicine for age-related disease could be very promising. We showed here that ISCGS can be cloned from a wide range of patients aged between 10 to 80. We did not detect any age-related loss of self-renewal or differentiation ability. In approximately 60 days, a single ISCGS can be expanded to about 1 billion cells for all 30 patients included in this study with remarkable stable wild-type genome, suggesting they may serve as ideal stem cell source for autologous transplantation targeting patients with intestinal disorders.

In 1980s, Howard Green and colleagues demonstrated the first example of cell therapy using cultured stem cells. They showed that human epidermis could be grown in the laboratory and transplanted onto burnt patients to reconstitute a functional epidermis. Since then, this procedure has been shown repeatedly life-saving for patients with severe burns. Furthermore, long-term effectiveness and safety of genetically modified epidermal stem cells to correct the severe skin blistering disease epidermolysis bullosa has been shown clinically. The successful clinical usage of epidermal stem cells has demonstrated a close correlation with the number of long-lived stem cells used in the procedure that can extensively self-renew in vitro and in vivo.

It remains unclear whether autologous transplantation of cultured intestinal cells can achieve the same success in clinical settings. Although it has been claimed that successful transplantation of organoids including a small fraction of intestinal stem cells can be achieved in murine models of experimental colitis, showing that these organoids adhere to and become an integrated part of the epithelium, it is likely that extremely limited number of stem cells in the organoid structures cannot support the long term intestinal epithelium regeneration in human.

In comparison to approximately 1% presence of intestinal stem cells in the organoids structures, the ground-state ISC culture comprises over 70% of ISCGS. Based on the previous lessons that we learned through clinical usage of cultured epidermal stem cells, it is conceivable that usage of ISCGS will significantly improve the efficacy and success of the transplantation. Another important advantage of ISCGS technology is our ability of establishing single-cell derived pedigree and expanding them quickly to 1 billion cells in about 60 days. We can anticipate aging or intestinal disorders may lead to the genomic changes in some intestinal stem cell clones and make these mutant cells not suitable for transplantation. In our study, using an example of a 56 yr old patient with UC, we demonstrated the polyclonal complexity of the cultured ISCGS and showed the co-existence of wild-type and mutant clones in one single patient. By screening single-cell derived pedigrees, we established a pedigree with wild-type genome and showed that this pedigree can self-renew, differentiate and can be expanded without any alarming genomic changes for an extensive period of time in vivo.

Taken together, our data supports the importance of screening cultured intestinal stem cells prior to transplantation for safety concerns and provides the solution for efficient and reliable stem cell source for personalized regenerative medicine. See FIG. 7.

D. An Efficient Method for Cloning Gastrointestinal Stem Cells from Patients Via Endoscopic Biopsies Inflammatory bowel disease, including Crohn's and ulcerative colitis, are considered and treated as diseases of the immune system. However, recent studies hint at the possibility that the intestinal epithelia may be key and perhaps primary players in the pathogenesis of Crohn's disease and ulcerative colitis. To assess the precise roles of intestinal epithelia in inflammatory bowel disease, systems are needed to isolate, clone, and examine the mucosal stem cells away from confounding influences of immune, stromal, and microbial cells. Studies of intestinal stem cells have been moving at a rapid pace led by the discovery of markers of stem cells, such as Lgr5, Bmi1, and others, used as stable lineage tracers in mouse models. Moreover, methods to isolate and analyze epithelial cells of the gastrointestinal tract have become paramount, either by entraining induced pluripotent stem cells to intestinal lineages or developing so-called organoids or miniguts. Despite the remarkable properties of intestinal stem cells revealed by these tracing and in vitro organoid studies, the field as a whole suffers from an inability to maintain patient-specific human intestinal stem cells in an immature state that would permit an analysis of potential pathogenic heterogeneity as well as the large-scale expansion of such clones for the range of studies addressing functional defects, drug discovery, and regenerative medicine.

Figure 8A:
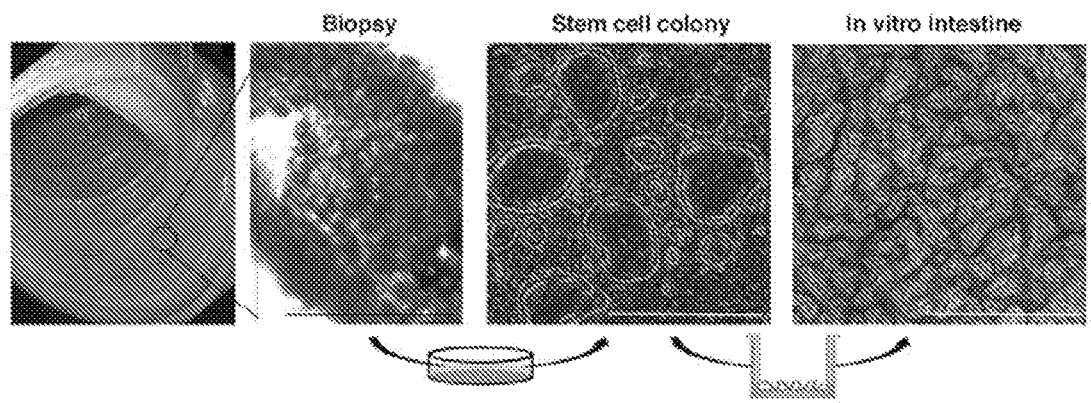
FIG. 8A: Clonal analysis of colonic stem cells from endoscopic biopsies. Workflow of generating "libraries" of single cell derived colonies and subsequently 3-dimensional intestinal epithelium from 1-mm endoscopic biopsies. White light imaging of a typical endoscopic biopsy, representative images of 100-300 colonies derived from a typical biopsy, top view of in vitro intestinal epithelium generated from these stem cells differentiated in an air-liquid interface setting. Scale bar, 1000 rm.
Figure 8B:
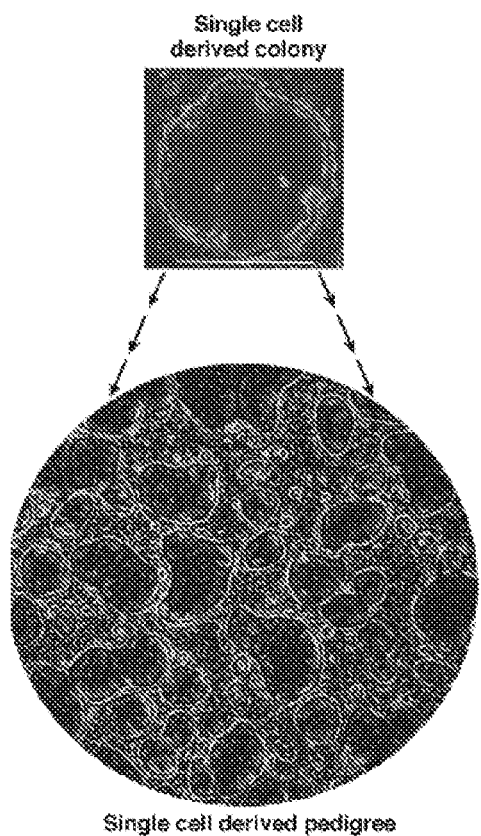
FIG. 8B: Clonal analysis of colonic stem cells from endoscopic biopsies. Individual colonies are sampled from the pool and grown in isolation as separate lines.
Figure 8C:
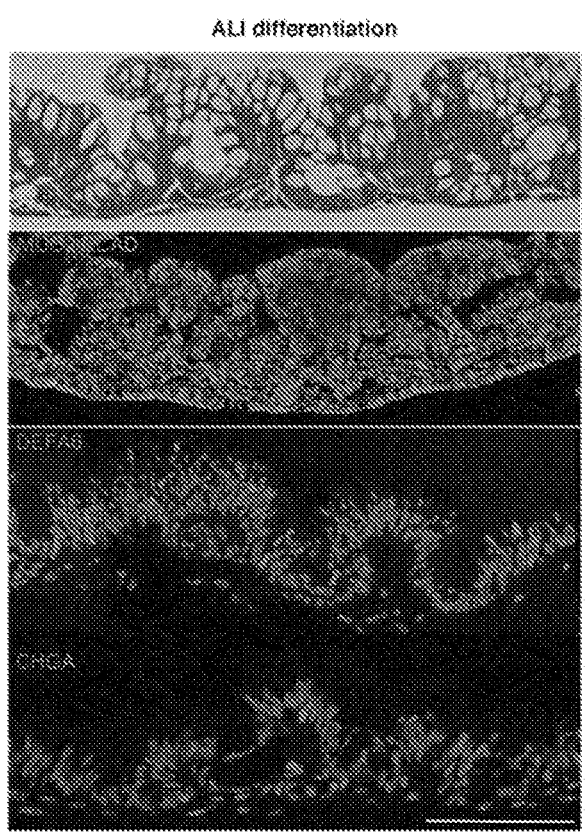
FIG. 8C: Clonal analysis of colonic stem cells from endoscopic biopsies. Histologic analysis of in vitro differentiated colonic epithelium via hematoxylin eosin staining, and immunofluorescence of antibodies to secretory cell markers Mucin 2, Chromogranin A, and Defensin alpha 6. Scale bar, 50 [m.
Figure 9A:
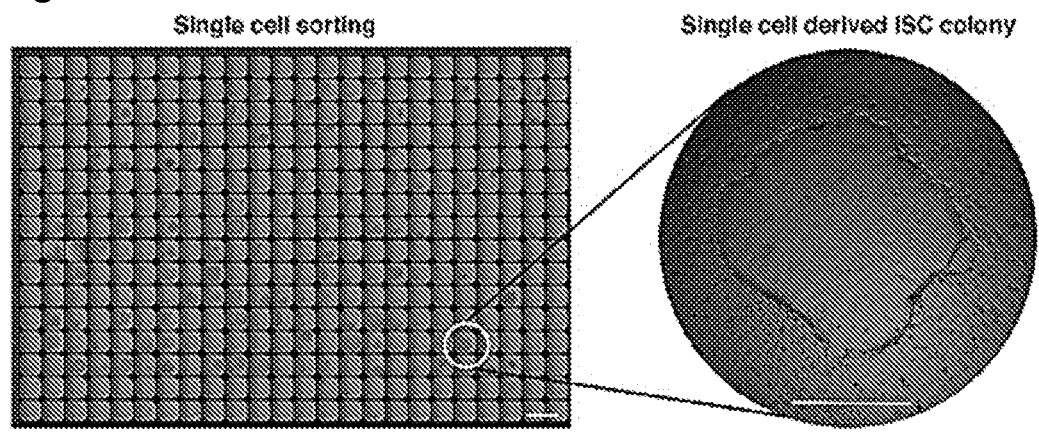
FIG. 9A: Immortality and rapid expansion of colonic stem cells in vitro. Clonogenicity of single GFPlabeled colonic stem cell sorted to individual wells.
Figure 9B:
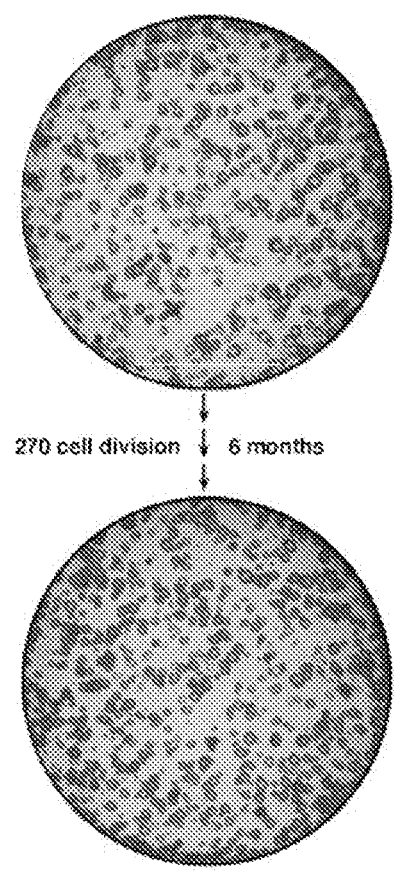
FIG. 9B: Immortality and rapid expansion of colonic stem cells in vitro. Clonogenicity assay revealing nearly unchanged number of Rhodamine red-stained colonies grown 10 days after seeding of 2000 passaged colonic stem cells.
Figure 9C:
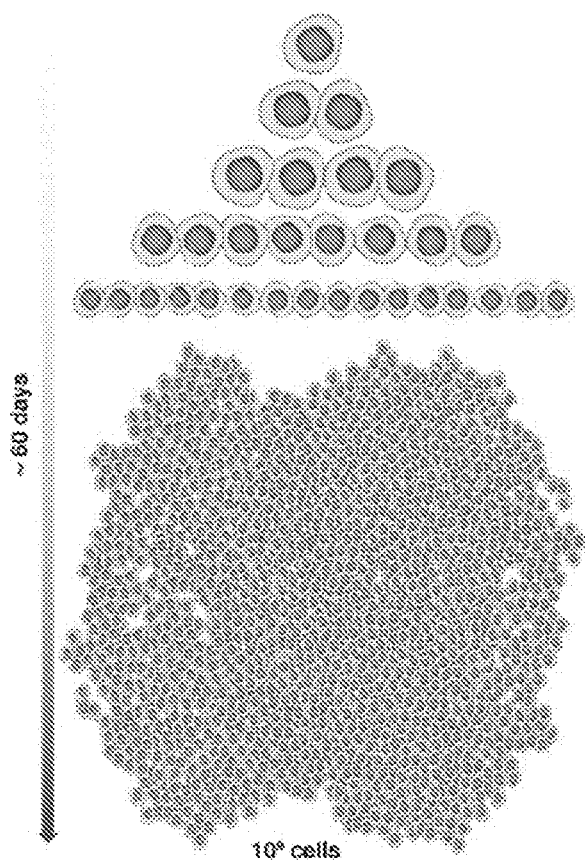
FIG. 9C: Immortality and rapid expansion of colonic stem cells in vitro. Rapid expansion of a single cell to 1 billion cells in approximately 60 days.

As described in this application, we have now developed robust methods to generate libraries of 100-300 independent stem cell clones from clinically standard 1-mm biopsies of human intestinal mucosa (FIG. 8). Briefly, the biopsy was enzymatically digested and seeded on irradiated 3T3-J2 feeder cells in the presence of the MGM media described above (and without feeders using the SGM-88 media). To induce differentiation, the stem cells were seeded on Transwell inserts (Corning, Corning, N.Y.). At confluency, the apical media was removed, and the cultures were continued for an additional 6-12 days (MGM media). Our method allows us to expand these clones as immature cells to practically unlimited numbers in vitro and achieve approximately 1 billion cells in <60 days (FIG. 9). Importantly, we are able to maintain each of these stem cell clones in a highly immature, clonogenic state that confers a host of advantages over either the induced pluripotent stem cells or the minigut approach, both of which yield relatively few stem cells among many differentiated cells. Moreover, these stem cells can be induced to differentiate into intestine-like structures including all cell lineages such as enterocytes, goblet cells, enteroendocrine cells and Paneth cells regardless of the number of stem cell passages sustained. In summary, the advantages of this system include (1) a highly uniform, homogeneous population of immature cells, (2) rapid and uniform propagation, (3) the ability to generate topologically precise, region-specific and regioncommitted stem cells using endoscopy-aided biopsy retrieval, (4) the ability to easily generate single-cell "pedigrees" for uniform somatic genotypes and cross-study analysis, and (5) the ability to assess both stem cell pedigrees and corresponding tissue for disease signatures. We anticipate that our studies will, in the long run, provide disease-linked stem cell pedigrees for a wide range of analyses in multiple laboratories to solve the basis of intestinal diseases and, ultimately, identify means of treating them.

Take Home Message

Single intestinal stem cells derived from 1 mm biopsies form colonies that can be sampled and independently propagated as pure "pedigrees." These single cell-derived pedigrees meet all the key criteria for stem cells, including long-term self-renewal (intrinsic immortality) and multipotency. These cells display remarkable clonogenicity rates of >70% upon subsequent passaging, and thus are near homogeneous populations of so-called ground state stem cells, in contrast with "organoids," where clonogenicity rates are <1%. The high clonogenicity of ground state stem cells is more than academic as it confers a high rate of "expandability" relative to organoids with a 250-fold advantage. Thus, 1 ground-state stem cell can proliferate to 1 billion cells in <60 days, sufficient to establish 10,000 3-dimensional intestinal cultures in the air-liquid interface system. Another significant property of these highly immature stem cells is that they possess all the information necessary to autonomously form complex 3-dimensional epithelia of the native mucosa from which they were derived. Taken together, this is a remarkably simple process for generating unlimited numbers of genetically stable and regionally committed stem cells from any patient for analysis via multiple technologies and by multiple laboratories.

E. Maintaining Immaturity of Human Gastrointestinal Stem Cells in a Feeder-Free System Stem cells of the gastrointestinal tract drive an exceedingly rapid process of tissue regeneration and have been at the conceptual center of adult stem cells based on engineered murine models. The ability of cloning and maintaining human intestine stem cells at their ground state in a feeder dependent system complement in vitro studies. Here we present efforts to establish a feeder free system to achieve the cloning of human gastrointestinal stem cells, establish pedigrees from single cells, and demonstrate the long-term self-renewal of these pedigrees while maintaining their committed multipotency to reconstitute intestinal villi in vitro including the formation of enterocytes, goblet cells, neuroendocrine cells, and paneth cells or gastric pits including the formation of mucous cells, parietal cells, chief cells and neuroendocrine cells. Despite the stable commitment of these gastrointestinal stem cells to intestinal lineages or stomach lineages respectively, whole genome expression analysis reveals their striking resemblance to each other consistent with their similar strategy of stem cell maintenance. The independence of feeder to maintain immaturity of adult stem cells in vitro for long periods without any genomic abnormalities provide certain advantage of using them for regenerative medicine and disease modeling.

Tissue-specific epithelial stem cells are promising tools for regenerative medicine. Cultured epidermal stem cells, corneal epithelial stem cells and lung stem cells have been successfully used in engraftment in clinics or mouse models. Stem cells of columnar epithelial tissue such as human intestine and colon have recently been cloned in their highly immature form in a feeder-based method. In comparison with the technologies of entraining induced pluripotent stem cells (iPSCs) to intestinal lineages or the development of regenerative, differentiated organoids (e.g., "miniguts"), the "ground-state" stem cells cloned in feeder system are intrinsically immortal demonstrated by maintaining self-renewal, multi-potency and genomic stability despite long-term culturing. Furthermore, the ability of deriving intestinal epithelial stem cells from a standard 1 mm endoscopic biopsy makes this technology compatible with standard-of-care patient monitoring protocols. However, preparation of murine-derived feeder cells in this system requires significant time and effort. In addition, the involvement of feeders can be incompatible with high-throughput drug screening, genomic analysis and usage of these cells for regenerative medicine. Thus, moving towards feeder-free culture system for adult stem cells would represent an essential and important improvement. The present study reports the development and validation of a feeder-free system to propagate "ground-state" human gastrointestinal stem cells (GSCGS and ISCGS). This technology provides an easy-to-use, robust and reproducible system for using adult stem cells derived from columnar epithelium in research and clinical applications.

Result

Human Gastrointestinal Stem Cells Self-Renew in Feeder Free System

A specialized media (designated above as SGM-88) was developed to support the maintenance of ground state and highly clonogenic form of human gastrointestinal stem cells in the absence of mouse fibroblast feeder cells. It contains novel combination of growth factors, regulators of FLT ((Vascular endothelial growth factor receptor), TGF-b/BMP (transforming growth factor-b/bone morphogenetic protein), EGF (epidermal growth factor), IGF(insulin-like growth factor), Wnt/b-catenin and Notch pathways. Therefore, ISCGS and GSCGS, which were previously established on feeder cells can be maintained in this media as highly immature cells without expressing differentiation markers.

The clonogenicity of cells is greater than 50% as determined by single cell transfer. The pedigrees could be propagated for months without change of clonogenicity. This high clonogenicity allow us to rapidly generate single-cell "pedigree" lines for expansion.

Multi-Potent Differentiation of Intestine and Stomach Stem Cells

Pedigree lines of ISCGS and GSCGS were differentiated in air-liquid interface (ALI) cultures for 10-30 days. ISCGS formed a highly uniform, 3D serpentine pattern. Histological analysis of sections of differentiated ISCGS showed a columnar epithelium of villus-like structures comprised with goblet (Muc2+), endocrine (chromogranin A+), Paneth (DEFA6+) cells and polarized villin expression. In contrast, GSCGS produced a 3D glandular pattern with pepsinogen producing zymogenic (chief) cells, hydrochloric acid secreting Parietal cells, mucous neck cells, gastric producing cells (G cells) and glucagon expressing (A cells). These results indicated that the progeny a single ISCGS or GSCGS can give rise to all epithelial lineages typically found in the small intestine or stomach. Significantly, the ground state stem cells differentiated upon polarity formation following exposure to an ALI instead of relying on a removal of factors such as Wnt or an addition of factors such γ-Secretase inhibitor (reference).

Although transcriptome analysis of ground state stem cells and ALI-differentiated tissue demonstrated gene expression divergence as expected for intestinal and gastric epithelia, the gene expression profiles of undifferentiated ISCGS and GSCGS differed by less than 1% (>2.0 fold, $P<0.5$). ISCGS showed high expression of intestinal stem-cell markers such as CD133, Lgr5 and Lrig1, where those from the stomach had the typical stem cells markers of gastric epithelium.

Feeder-Independent Genomic and Lineage Stability

To assess the genomic stability of ISCGS and GSCGS in this feeder-free system, we examined copy number variation (CNV) and single nucleotide variation (SNV) by whole exome sequencing (150× in average) in ISCGS and GSCGS pedigrees after 20 (passage 2; P2), 40 (P3), 60 (P6), 80 (P8) and 100 days (P11) of continuous proliferation. At P10, when single ISCGS or GSCGS pedigree can be amplified to an estimated 1 billion to 10 billion cells, no copy number abnormality was detected. Thus, this low level of structural variation was maintained through passage 10. By comparing to P2, ISCGS and GSCGS pedigrees demonstrated few (0-3) point mutations through passage 10, in which two SNPs are common variants and one SNP is synonymous mutation. No new indel and LOH event was found during passaging. These results suggest that these pedigrees sustain few genomic changes within the first 100 days of proliferative expansion.

We next compared early and late passages of ISCGS and GSCGS pedigrees in ALI differentiation. Based on histological criteria including gastric and intestinal marker staining, we could not distinguish the ALI-differentiated epithelia derived from P2 and P10. Furthermore, we find that ISCGS and GSCGS pedigrees don't lose (or gain) clonogenicity when tested at P2 and P10, which remain stably above 50%. Finally, we found no evidence of tumorigenicity by these ground state intestine and stomach stem cells following their subcutaneous implantation to immunodeficient (NOD.Cg-Prkdcscid Il2rgtm1Wjl/SzJ) mice. In contrast, ISCGS and GSCGS pedigrees generated well-differentiated epithelia that resemble the respective epithelia (intestine and stomach) from which they were derived.

The invention claimed is:

1. A defined culture medium for isolating and stably maintaining the epigenetics of columnar epithelial stem cells through a plurality of passaging in culture, the medium comprising: a basal medium; and each of a ROCK (Rho Kinase) inhibitor, a Wnt agonist, a mitogenic growth factor, insulin or IGF, a BRAF inhibitor, a VEGF inhibitor, an Oct4-activating agent, a PDGFRα/β inhibitor, and a JNK Inhibitor, substantially free of co-cultured feeder cells.

2. The defined culture medium of claim 1, further comprising a TGFβ signaling pathway inhibitor.

3. The defined culture medium of claim 1, characterized in that, when stem cells of columnar epithelial tissue origin are cultured therein, and in the absence of co-cultured feeder cells, clonogenicity is maintained.

4. The defined culture medium of claim 3, wherein clonogenicity is maintained above 50% for at least 10 passages.

5. The defined culture medium of claim 1, further comprising a Notched agonist, a Bone Morphogenetic Protein (BMP) antagonist, and nicotinamide.

6. The defined culture medium of claim 1, wherein the Wnt agonist is R-spondin-1, the mitogenic growth factor is EGF, the BRAF inhibitor is GDC-0879, the VEGF inhibitor is Tivozanib), the Oct4-activating agent is OAC1, the PDGFRα/β inhibitor is CP673451, and the JNK inhibitor is JNK-IN-8.

7. The defined culture medium of claim 2, wherein the TGFβ signaling pathway inhibitor is SB431542.

8. The defined culture medium of claim 5, wherein the Notched agonist is Jagged-1, the BMP antagonist is Noggin.

9. The defined culture medium of claim 1, further comprising an additional ROCK inhibitor.

10. The defined culture medium of claim 9, comprising ROCK inhibitors GSK429286A and Y-27632.

* * * * *

UNITED STATES PATENT AND TRADEMARK OFFICE
CERTIFICATE OF CORRECTION

| | | |
|---|---|---|
| PATENT NO. | : 11,725,185 B2 | |
| APPLICATION NO. | : 16/958074 | |
| DATED | : August 15, 2023 | |
| INVENTOR(S) | : Wa Xian et al. | |

It is certified that error appears in the above-identified patent and that said Letters Patent is hereby corrected as shown below:

In the Specification

Column 1, Line 16, please insert the following:
--STATEMENT REGARDING FEDERALLY FUNDED RESEARCH
This invention was made with government support under Grant No. 1449402-20-0003 awarded by the National Institutes of Health. The government has certain rights in the invention.--

Signed and Sealed this
Twentieth Day of February, 2024

Katherine Kelly Vidal
*Director of the United States Patent and Trademark Office*